US012583820B2

(12) United States Patent
Chang et al.

(10) Patent No.: US 12,583,820 B2
(45) Date of Patent: Mar. 24, 2026

(54) BROAD SPECTRUM ANTIVIRALS AGAINST CORONAVIRUS

(71) Applicants: Kansas State University Research Foundation, Manhattan, KS (US); Wichita State University, Wichita, KS (US); University of Iowa Research Foundation, Iowa City, IA (US)

(72) Inventors: Kyeong-Ok Chang, Manhattan, KS (US); Yunjeong Kim, Manhattan, KS (US); William C. Groutas, Wichita, KS (US); Stanley Perlman, Iowa City, IA (US)

(73) Assignees: Kansas State University Research Foundation, Manhattan, KS (US); Wichita State University, Wichita, KS (US); University of Iowa Research Foundation, Iowa City, IA (US)

( * ) Notice: Subject to any disclaimer, the term of this patent is extended or adjusted under 35 U.S.C. 154(b) by 719 days.

(21) Appl. No.: 17/907,745

(22) PCT Filed: Mar. 30, 2021

(86) PCT No.: PCT/US2021/024790
§ 371 (c)(1),
(2) Date: Mar. 24, 2023

(87) PCT Pub. No.: WO2021/202460
PCT Pub. Date: Oct. 7, 2021

(65) Prior Publication Data

US 2023/0150933 A1 May 18, 2023

Related U.S. Application Data

(60) Provisional application No. 63/036,542, filed on Jun. 9, 2020, provisional application No. 63/001,781, filed on Mar. 30, 2020.

(51) Int. Cl.
*C07D 207/26* (2006.01)
*C07D 405/12* (2006.01)

(52) U.S. Cl.
CPC ......... *C07D 207/26* (2013.01); *C07D 405/12* (2013.01)

(58) Field of Classification Search
CPC .................................................... C07D 207/26
See application file for complete search history.

(56) References Cited

U.S. PATENT DOCUMENTS

| | | | |
|---|---|---|---|
| 9,309,284 | B2 | 4/2016 | Chang et al. |
| 9,474,759 | B2 | 10/2016 | Chang et al. |
| 11,013,779 | B2 | 5/2021 | Chang et al. |
| 11,033,600 | B2 | 6/2021 | Chang et al. |
| 2014/0243341 | A1 | 8/2014 | Chang et al. |

FOREIGN PATENT DOCUMENTS

| | | |
|---|---|---|
| WO | 2013/049382 | 4/2013 |
| WO | 2013/166319 | 11/2013 |
| WO | 2017/222935 | 12/2017 |
| WO | 2018/023054 | 2/2018 |
| WO | 2021206876 | 10/2021 |

OTHER PUBLICATIONS

Search Report in corresponding European U.S. Appl. No. 21/781,006, dated Mar. 18, 2024.
Rathnayake, et al., "Structure-Guided Optimization of Dipeptidyl Inhibitors of Norovirus 3CL Protease", J. Med. Chem. 2020, 63, 11945-11963.
Extended European Search Report in co-pending European Patent Application Serial No. 21781006.8, dated Jul. 1, 2024.
Supplementary European Search Report in co-pending European Patent Application Serial No. 21781006.8, dated Jul. 18, 2024.
International Search Report and Written Opinion in corresponding PCT/US2021/24790, dated Aug. 31, 2021.
Ba, et al., "Boceprevir, GC-376, and calpain inhibitors II, XU inhibit SARS-CoV-2 viral replication by targeting the viral main protease", Cell Research, 2020, 30, pp. 678-692.
Kim, et al., "Broad-Spectrum Antivirals against 3C or 3C-Like Proteases of Picornaviruses, Noroviruses, and Coronaviruses", J Virol, 2012, 86(21), pp. 11754-11762.
Kankanamalage, et al., "Structure-guided design of potent and permeable inhibitors of MERS coronavirus 3CL protease that utilize a piperidine moiety as a novel design element", Eur J Med Chem, 2018, 150, pp. 334-346.
Park, et al., "Metabolism of fluorine-containing drugs", Annu Rev Pharmacol Toxicol, 2001, 41, pp. 443-447.
Office Action in co-pending Chinese Patent Application Serial No. 2021800268507, dated Oct. 31, 2024 (English translation attached).
Office Action in co-pending European Patent Application Serial No. 21781006.8, dated Oct. 29, 2025.

*Primary Examiner* — Golam M Shameem
(74) *Attorney, Agent, or Firm* — Hovey Williams LLP; Crissa A. Cook

(57) ABSTRACT

Compounds exhibiting antiviral activity and/or inhibition of viral replication against viruses, particularly those belonging to the picornavirus-like supercluster, including coronavirus having a formula: (I) where X comprises a cyclic moiety, $R_2$ is a branched or unbranched alkyl, cycloalkyl, aryl, arylalkyl, alkenyl, alkynyl, amino acid side chain, bicyclic or tricyclic side chain, combinations, and substituted forms thereof, and Z is selected from the group consisting of $C_1$-$C_6$ hydroxyalkyl, aldehydes, alpha-ketoamides, and bisulfite salts, and in particular —$CH_2OH$, —CHO, —$CH(0H)S0_3^-$ $Na^+$, and -$[0(C{=}0)R_w]S0_3^-Na^+$.

12 Claims, 20 Drawing Sheets

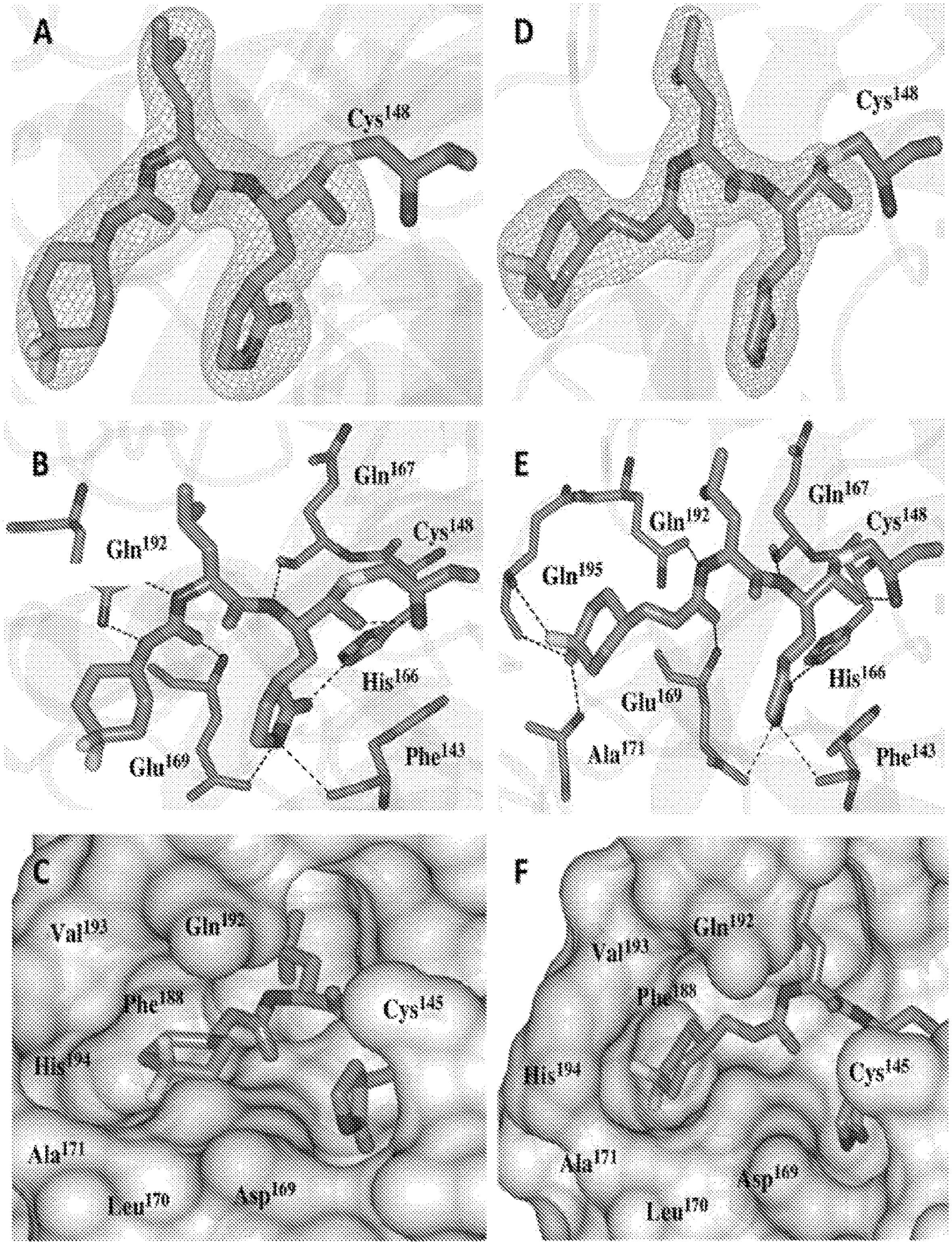
Fig. 2A-F

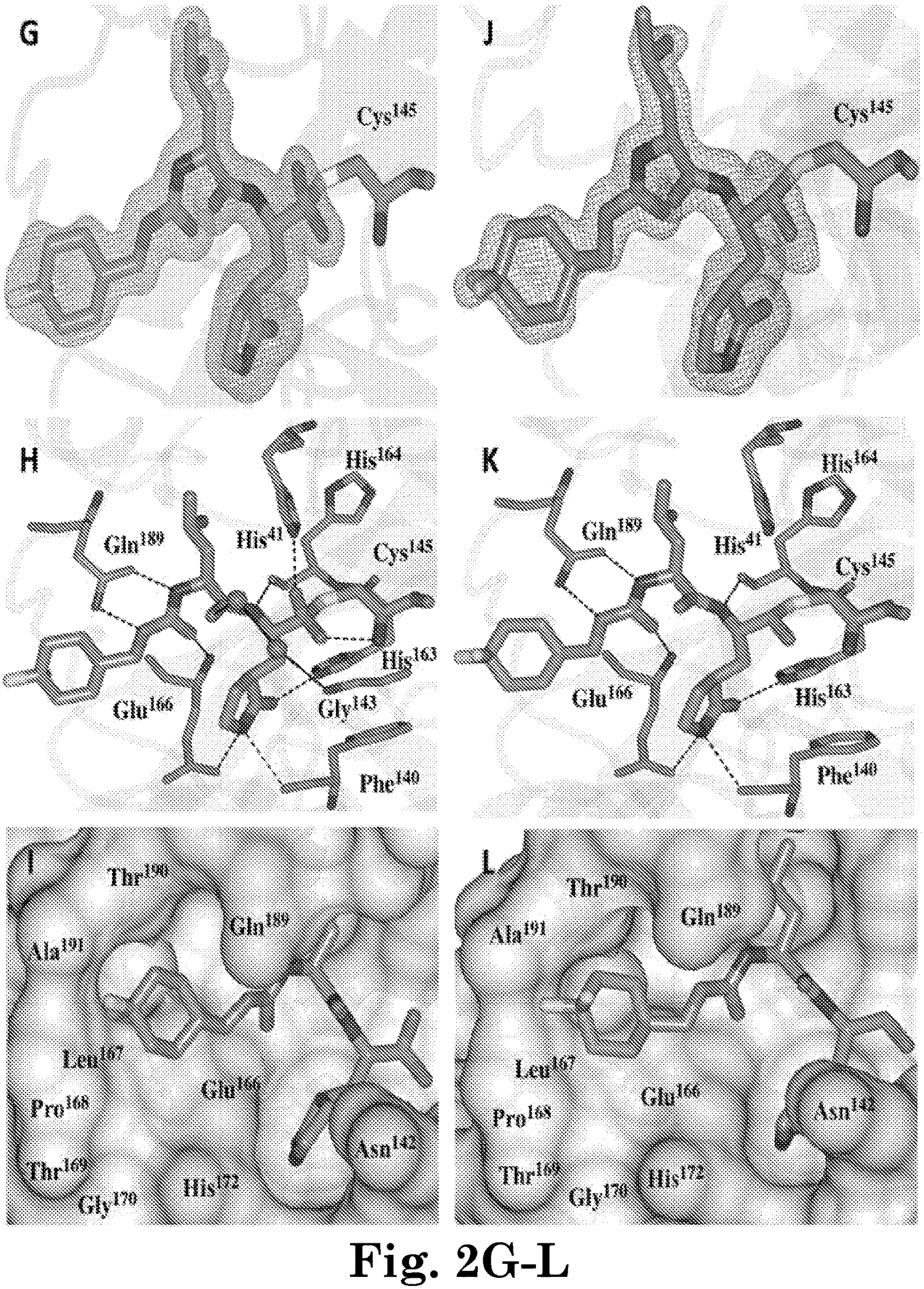
Fig. 2G-L

Scheme 2

Scheme

A Synthesis of precursor alcohols 12-16

B Synthesis of inhibitors 1-24b-c

C Synthesis of amino alcohol A

BROAD SPECTRUM ANTIVIRALS AGAINST CORONAVIRUS

CROSS-REFERENCE TO RELATED APPLICATIONS

The present application is the U.S. National Stage of International Patent Application No. PCT/US2021/024790, filed Mar. 31, 2021, which claims the priority benefit of U.S. Provisional Patent Application Ser. Nos. 63/001,781, filed Mar. 30, 2020, and 63/036,542, filed Jun. 9, 2020, each entitled BROAD SPECTRUM ANTIVIRALS AGAINST CORONAVIRUS, and each of which is incorporated by reference in its entirety herein.

STATEMENT REGARDING FEDERALLY-FUNDED RESEARCH

This invention was made with U.S. Government support under grant number R01 AI130092 awarded by the National Institutes of Health. The government has certain rights in the invention.

BACKGROUND OF THE INVENTION

Field of the Invention

The present disclosure relates to broad-spectrum antiviral compounds targeting the 3C-like proteases of coronavirus.

Description of Related Art

Many viruses encode polyproteins with proteases which catalyze their subsequent cleavage to the mature functional proteins and are essential for viral replication. Previous attempts have been made to inhibit viral activity by targeting such proteases. However, most protease inhibitors have a short range of specificity that is genus-, species-, or even strain-specific due to structural variations in the viral proteases. Thus, broad spectrum antivirals are rare and have proven elusive to researchers.

Highly pathogenic coronaviruses are a significant threat to public health, as exemplified by Severe Acute Respiratory Syndrome coronavirus (SARS-CoV), Middle East respiratory syndrome coronavirus (MERS-CoV), and the newly emerged SARS-CoV-2, a causative agent of coronavirus disease 2019 (COVID19). Other members of the picornavirus-like supercluster, such as caliciviruses (including norovirus and sapovirus genera) and picornaviruses share a common feature with coronaviruses in that they also possess a viral 3C or 3CL protease which is responsible for most cleavages of the corresponding viral polyprotein. These 3C and 3CL proteases share some common characteristics, including a typical chymotrypsin-like fold and a catalytic triad (or dyad) with Cys-His-Glu (or Asp) on the protease, and a preference for a Glu or Gln residue at the P1 position on the substrate. Caliciviruses include noroviruses (Norwalk virus [NV]), feline calicivirus, MD145, murine norovirus [MNV], vesicular exanthema of swine virus, and rabbit hemorrhagic disease virus. Picornaviruses include enteroviruses (such as enterovirus 71), poliovirus, coxsackievirus, foot-and-mouth disease virus (FMDV), hepatitis A virus (HAV), porcine teschovirus, and rhinovirus (cause of common cold).

Coronaviruses, in particular, are a large group of viruses that can cause a wide variety of diseases in humans and animals. Coronaviruses include human coronavirus (cause of the common cold such as 229E strain), transmissible gastroenteritis virus (TGEV), murine hepatitis virus (MHV), bovine coronavirus (BCV), feline infectious peritonitis virus (FIPV), and SARS-Co. Most human coronaviruses generally cause the common cold, a mild upper respiratory illness. However, global outbreaks of new human coronavirus infections with severe respiratory disease have periodically emerged from animals, which includes SARS-CoV, MERS-CoV, and most recently, SARS-CoV-2, which emerged in China in December 2019 and subsequently spread throughout the world. The genetic analysis of SARS-CoV-2 showed it to be closely related to SARS-like beta-coronaviruses of bat origin, bat-SL-CoVZC45 and bat-SL-CoVZXC21. Despite the periodic emergence of novel coronaviruses infecting humans, there are no broadly effective FDA-approved vaccines or antiviral drugs against these viruses, underscoring an urgent need for the development of preventive and therapeutic measures against coronaviruses.

The SARS-CoV-2 genome is large (~30 kb) and similar to the genomes of SARS-CoV and MERS-CoV (~80% and ~50% sequence identity, respectively). It contains two open reading frames (ORF1a and ORF1b) and encodes multiple structural and nonstructural proteins. Translation of the genomic mRNA of ORF1a yields a polyprotein (pp1a), while a second polyprotein (pp1b) is the product of a ribosomal frameshift that joins ORF1a together with ORF1b. The two polyproteins are processed by a 3C-like protease (3CLpro, also referred to as Main protease, Mpro) (11 cleavage sites) and a papain-like cysteine protease (PLpro), resulting in 16 mature nonstructural proteins including an RNA-dependent RNA polymerase (RdRp) which are involved in the replication-transcription complex. Both 3CLpro and PLpro are essential for viral replication, making them attractive targets for drug development. Coronavirus 3CLpro is a chymotrypsin-like cysteine protease that has two N-terminal domains containing two β-barrel chymotrypsin-like folds. The active site of 3CLpro is located in the cleft between the two domains and is characterized by a catalytic Cys148-His41 dyad.

Our foray in this area has resulted in the discovery of broad-spectrum inhibitors of an array of viruses, including coronaviruses and noroviruses that encode 3CLpro as well as the first demonstration of clinical efficacy of a coronavirus 3CLpro inhibitor (GC376, currently in clinical development, see U.S. Pat. No. 9,474,759, issued Oct. 25, 2016, incorporated by reference herein in its entirety). Specifically, administration of a 3CLpro inhibitor to cats with feline infectious peritonitis (FIP), a coronavirus-induced systemic disease that is 100% fatal, reversed the progression of FIP and resulted in clinical remission. We have furthermore reported recently the results of exploratory in-vitro studies using a dipeptidyl series of MERS-CoV 3CLpro inhibitors that embody a piperidine moiety as a novel design element, as well as pertinent structural and biochemical studies.

SUMMARY OF THE INVENTION

The COVID-19 pandemic remains a major concern for public health worldwide and there is an urgent need for the creation of effective therapeutics, including vaccines, biologics, and small molecule therapeutics, to combat SARS-CoV-2, and emerging variants. Inspection of the virus life cycle reveals multiple viral and host-based choke points that can be exploited to combat the virus. SARS-CoV-2 3CL protease, an enzyme essential for viral replication, is an attractive viral choke point and the design of inhibitors of the protease may lead to the emergence of effective SARS-CoV-2-specific antivirals.

Here, we report 3CLpro inhibitors highly potent against multiple coronaviruses including MERS-CoV, SARS-CoV, and SARS-CoV-2 in enzyme and/or cell-based assays. In the mouse model of MERS-CoV infection, administration of a lead compound one day after virus infection significantly increased survival and reduced lung virus titers and histopathology, demonstrating the proof-of-concept treatment efficacy. The results suggest the series has the potential to be developed as broad spectrum antivirals against these important human coronaviruses as well as against other viruses that belong to the picornavirus-like supercluster, including caliciviruses and picornaviruses.

In one aspect, an antiviral compound comprising formula I, or a pharmaceutically-acceptable salt or prodrug thereof is provided:

(I)

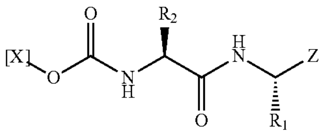

wherein, each X comprises at least one cyclic moiety, and in particular a substituted or unsubstituted $C_3$-$C_{10}$ cycloalkyl, a substituted or unsubstituted 3-7 membered heterocycle having 1-3 ring heteroatoms selected from N, O, and S, or a substituted $C_{6-10}$ aryl group, which may be directly attached to the oxygen, or may be connected via a branched or unbranched and substituted or unsubstituted $C_1$-$C_6$ alkyl linkage, or a branched or unbranched $C_1$-$C_6$ alkylene; $R_1$ is glutamine or imidazole surrogate; $R_2$ is a branched or unbranched alkyl, cycloalkyl, aryl, arylalkyl, alkenyl, alkynyl, natural (Leu) or unnatural (Cha) amino acid side chain, bicyclic or tricyclic side chain, or a combination thereof, and in particular a branched or unbranched $C_1$-$C_6$ alkyl, $C_3$-$C_{10}$ cycloalkyl, $C_{6-10}$ aryl, $C_1$-$C_6$ alkylene-$C_{6-10}$ aryl, $C_2$-$C_6$ alkenyl, $C_2$-$C_6$ alkynyl, or a combination thereof, wherein $C_1$-$C_6$ alkyl is optionally substituted with one or more halogen, —OH, —SH, —$SCH_3$, —$NH_2$, —COOH, —C(O)$NH_2$, —NH(C═NH)$NH_2$, $C_3$-$C_{10}$ cycloalkyl, $C_{6-10}$ aryl optionally substituted with —OH, or 5-9 membered heteroaryl having 1-3 ring heteroatoms selected from N, O, and S; Z is selected from the group consisting of $C_1$-$C_6$ hydroxyalkyl, aldehydes, alpha-ketoamides, and bisulfite salts, and in particular —$CH_2OH$, —CHO, —$SO_3Na$, —CH(OH)$SO_3^-Na^+$, and —[O(C═O)$R_w$]$SO_3^-Na^+$, where $R_w$ is an alkyl or arylalkyl with —$CH_3$ and —$CH_2CH_3$ being particularly preferred. Deuterated forms of the foregoing compounds are also contemplated herein.

A method of treating or preventing viral infection in a subject from one or more coronaviruses as well as against other viruses that belong to the picornavirus-like supercluster, including caliciviruses and picornaviruses is also provided. The method comprises administering to said subject a therapeutically-effective amount of a first antiviral compound according to the various embodiments described herein.

A broad spectrum antiviral composition is also disclosed. The composition comprises a first antiviral compound according to the various embodiments described herein dispersed in a pharmaceutically-acceptable carrier.

A kit is also provided herein. The kit comprises: an antiviral compound according to the various embodiments described herein; and instructions for administering the compound to a subject in need thereof.

A method of preventing or inhibiting replication of a virus in a cell is also disclosed. The method comprises contacting a coronavirus, picornavirus, or calicivirus cell with a compound according to the various embodiments described herein.

Also disclosed is the use of a compound according to the various embodiments described herein to prepare a therapeutic or prophylactic medicament for the treatment or prevention of a viral infection from coronaviruses, picornavirus, or calicivirus in a subject.

BRIEF DESCRIPTION OF THE DRAWINGS

FIG. 2A-F show X-ray crystal structures of MERS-CoV 3CLpro with 6h (A, B, C) and 7j (D, E, F).

FIG. 2G-L shows X-ray crystal structures of SARS-CoV 3CLpro with 7j (G, H, I), and SARS-CoV-2 3CLpro with compound 7j (J, K, L). In FIGS. 2A-F and 2G-L, panels (A), (D), (G), and (J) show $F_o$-$F_c$ omit maps (green mesh) contoured at 3σ; panels (B), (E), (H), and (K) show hydrogen bond interactions (dashed lines) between the inhibitor and the 3CL protease; and panels (C), (F), (I), and (L) show electrostatic surface representation of the binding pocket occupied by the inhibitor. Neighboring residues are colored yellow (nonpolar), cyan (polar), and white (weakly polar).

DETAILED DESCRIPTION

Figure 1:
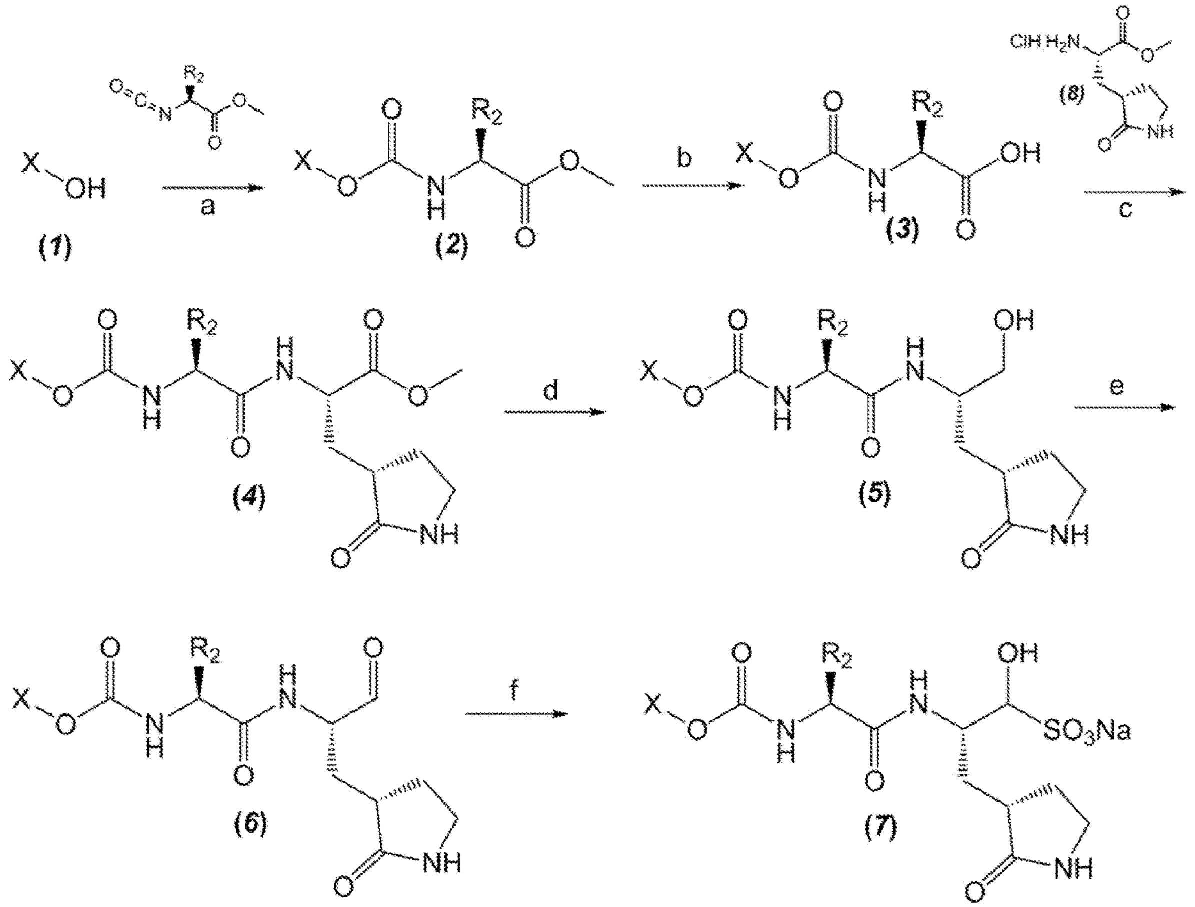
FIG. 1 shows reaction Scheme 1 for the stepwise compound synthesis with intermediate compounds for 3C-like protease (3CLpro) inhibitors of the 6a to 6k and 7a to 7k series. The alcohol inputs were reacted with (L) leucine isocyanate methyl ester or (L) cyclohexylalanine isocyanate methyl ester to yield products, which were then hydrolyzed to the corresponding acids with lithium hydroxide in aqueous tetrahydrofuran. Subsequent coupling of the acids to glutamine surrogate methyl ester "8" furnished compounds "4". Lithium borohydride reduction yielded alcohols "5", which were then oxidized to the corresponding aldehydes "6" with Dess-Martin periodinane reagent. The bisulfite adducts "7" were generated by treatment with sodium bisulfite in aqueous ethanol and ethyl acetate. Step a) Amino acid methyl ester isocyanate/TEA/CH3CN/reflux/2 hours; Step b) 1M LiOH/THF/RT/3 hours; Step c) EDCI/HOBT/glutamine surrogate/DIPEA/DMF/RT/24 hours; step d) 2M LiBH4/THF/methanol/RT/12 hours; Step e) Dess-Martin periodinane/DCM/15° to 18° C./3 hours; and step f) $NaHSO_3$/ethyl acetated/ethanol/$H_2O$/44° to 55° C.
Figure 3:
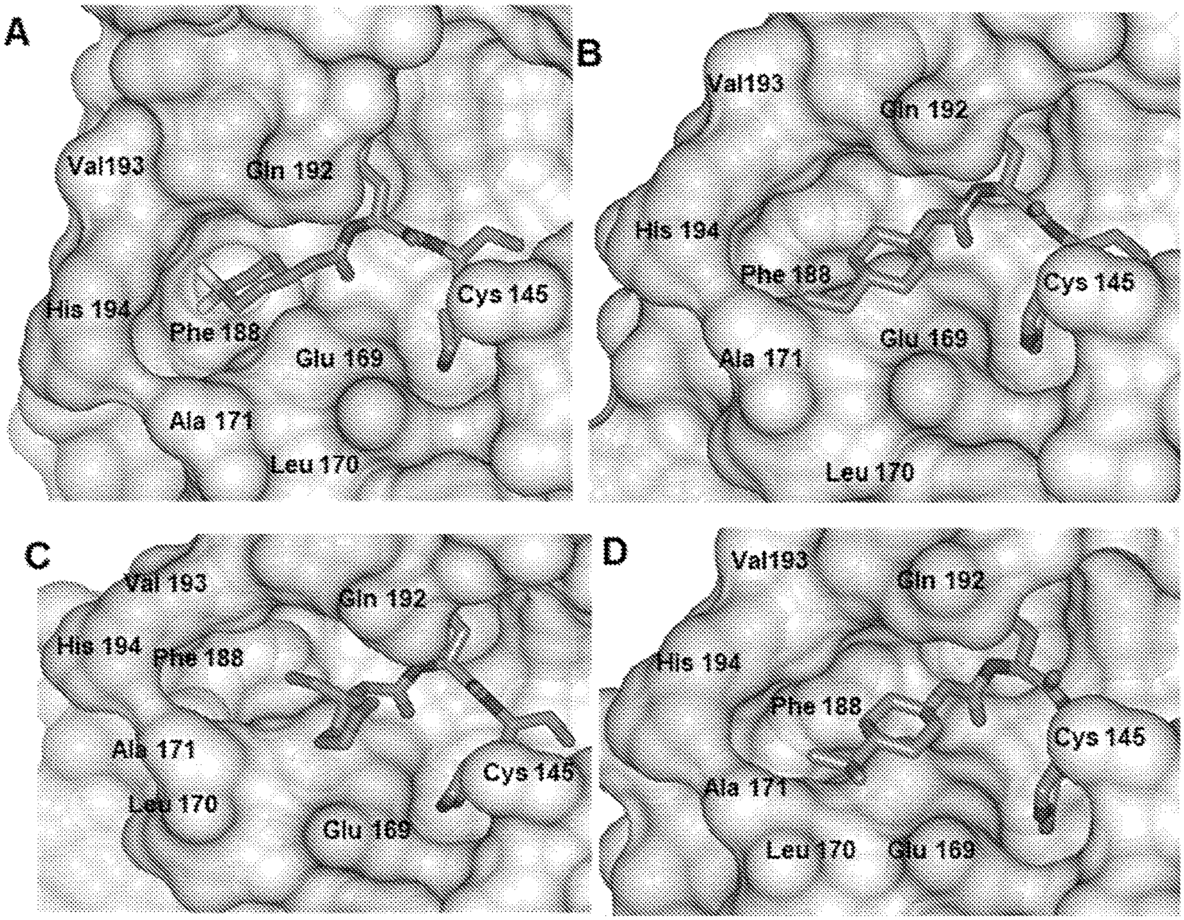
FIG. 3 shows the electrostatic surface representation of the MERS-CoV 3CLpro pocket occupied by A) 7i, B) 6b, C) 6g, and D) 6d. Neighboring residues are colored yellow (nonpolar), cyan (polar) and white (weakly polar).
Figure 4:
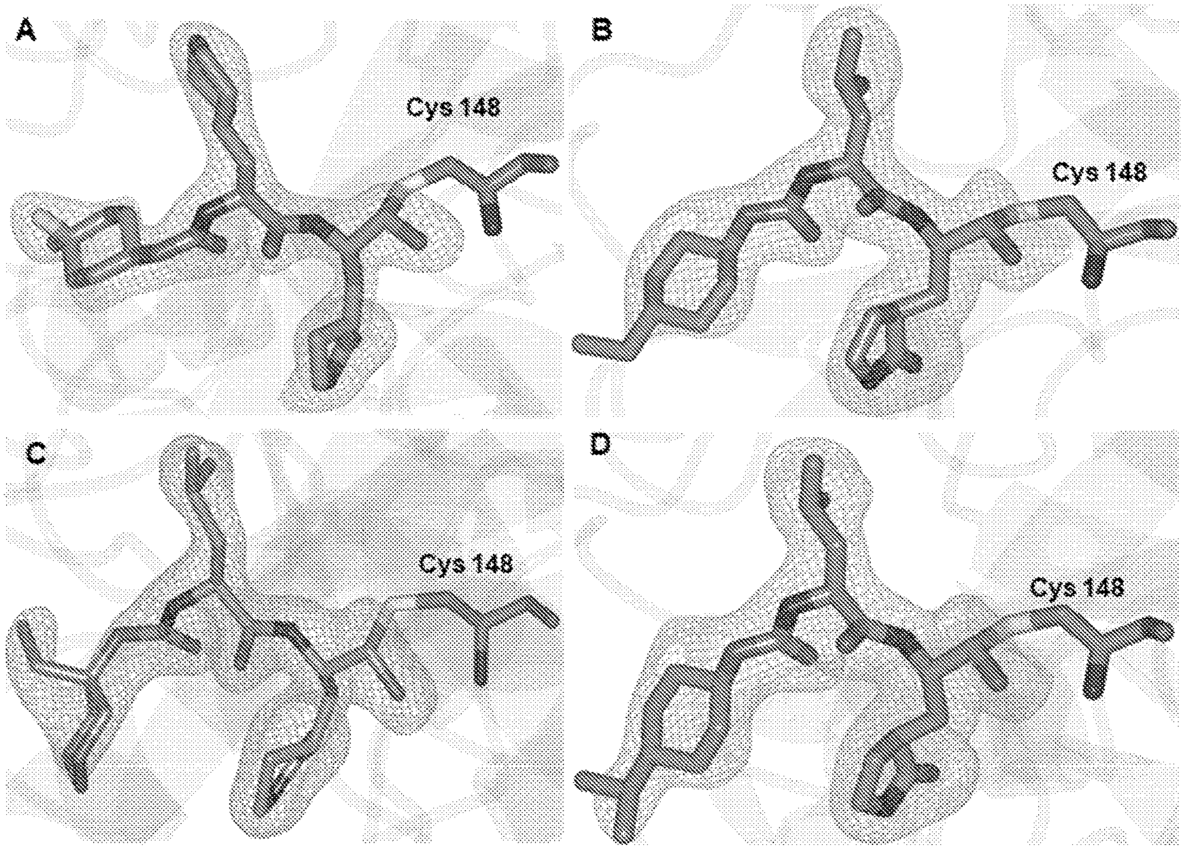
FIG. 4 shows the $F_o$-$F_c$ omit maps (green mesh) contoured at 3σ for the inhibitor bound structures of MERS-CoV 3CLpro with A) 7i, B) 6b, C) 6g, and D) 6d.

A series of non-deuterated and deuterated 3CLpro protease inhibitors and prodrug forms have been synthesized and demonstrated to possess broad-spectrum activity against multiple coronaviruses including MERS-CoV, SARS-CoV, and SARS-CoV-2, as well as against other viruses that belong to the picornavirus-like supercluster, including caliciviruses and picornaviruses, in enzymatic and cell-based assays. The efficacy of the compounds in an animal model of MERS-CoV infection is also demonstrated. Members of this series of compounds are highly effective as antiviral therapeutics targeting a specific virus or, more importantly, they are broad-spectrum antivirals targeting multiple viruses. The wide applicability of the latter constitutes a significant advance in antiviral research and public health.

Embodiments described herein include antiviral compounds having broad-spectrum (multivalent) activity against coronaviruses as well as against other viruses that belong to the picornavirus-like supercluster, including caliciviruses and picornaviruses. Without wishing to be bound by theory, the compounds are small-molecule based antivirals that effectively target and inhibit viral 3CL protease activity across multiple virus species, strains, and subtypes, thereby preventing formation of the mature virus and inhibiting virus replication in the host cell. In some embodiments, the compounds are prodrugs that are converted into active compounds that target and inhibit viral 3CL protease activity.

In some embodiments, antiviral compounds comprising (consisting essentially or even consisting of) formula (I), or the pharmaceutically-acceptable salt thereof, are provided:

(I)

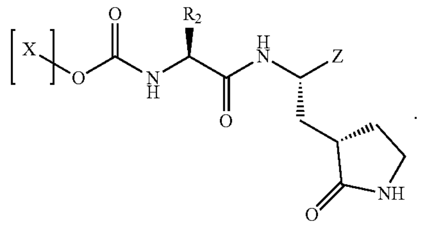

In the foregoing structure, X comprises at least one cyclic moiety, and in particular a substituted or unsubstituted $C_3$-$C_{10}$ cycloalkyl, a substituted or unsubstituted 3-7 membered heterocycle having 1-3 ring heteroatoms selected from N, O, and S, or a substituted $C_{6-10}$ aryl group, which may be directly attached to the oxygen, or may be connected via a branched or unbranched and/or substituted or unsubstituted $C_1$-$C_6$ alkyl linkage, or a branched or unbranched $C_1$-$C_6$ alkylene. Substituted or unsubstituted $C_3$-$C_6$ cycloalkanes or saturated heterocycles are particularly preferred cyclic moieties, with cyclohexane and 6-membered heterocycles being most preferred (most preferably oxygen heterocyclic compounds). The cycloalkanes and heterocycles may be mono- or di-substituted. In the case of disubstituted rings, the two substituents are on the same ring atom. When X comprises a substituted aryl group, para-substitutions are particularly preferred. Preferred substituents include halogens (—F, —Cl, —Br, with —F particularly preferred), as well as $C_1$-$C_6$ branched or unbranched alkyls. Substituted aryl groups are preferably phenyl groups, preferably monosubstituted with a halogen substituent (—F, —Cl, —Br, with —F particularly preferred). Meta-substitutions are particularly preferred in such embodiments. As noted, the cyclic moiety can be attached to the oxygen directly or via a branched or unbranched $C_1$-$C_6$ alkyl linkage. In some embodiments, the linkage may further comprise one or more side chain groups including substituted or unsubstituted alkyls ($C_1$-$C_6$ alkyl), substituted or unsubstituted aryls (e.g., phenyl, substituted phenyl), arylalkyl (e.g. benzyl or group where the aryl is naphthyl), and the like.

In the foregoing structure, each $R_2$ is a branched or unbranched alkyl, cycloalkyl, aryl, arylalkyl, alkenyl, alkynyl, natural (e.g., Leu) or unnatural (e.g., Cha) amino acid side chain, bicyclic or tricyclic side chain, or a combination thereof, and in particular is a branched or unbranched $C_1$-$C_6$ alkyl, $C_3$-$C_{10}$ cycloalkyl, $C_{6-10}$ aryl, $C_1$-$C_6$ alkylene-$C_{6-10}$ aryl, $C_2$-$C_6$ alkenyl, $C_2$-$C_6$ alkynyl, or a combination thereof, wherein $C_1$-$C_6$ alkyl is optionally substituted with one or more halogen, —OH, —SH, —$SCH_3$, —$NH_2$, —COOH, —C(O)$NH_2$, —NH(C═NH)$NH_2$, $C_3$-$C_{10}$ cycloalkyl, $C_{6-10}$ aryl optionally substituted with —OH, or 5-9 membered heteroaryl having 1-3 ring heteroatoms selected from N, O, and S, and for example where $R_2$ can be in particular a bicyclic or tricyclic side chain, leucine (Leu), cyclohexylalanine (Cha), or a fluorinated side chain.

In the foregoing structure, each Z is selected from the group consisting of $C_1$-$C_6$ hydroxyalkyl, aldehydes, alpha-ketoamides, and bisulfite salts, and in particular —$CH_2OH$, —CHO, —CH(OH)$SO_3^-Na^+$, and —[O(C═O)$R_w$]$SO_3^-$ $Na^+$, where $R_w$ is an alkyl or arylalkyl with —$CH_3$ and —$CH_2CH_3$ being preferred.

The present disclosure encompassed deuterated forms of the foregoing compounds.

As used herein, the term "alkyl" refers to straight chained and branched saturated hydrocarbon groups containing one to thirty carbon atoms, for example, one to twenty carbon atoms, or one to ten carbon atoms. The term $C_n$ means the alkyl group has "n" carbon atoms. For example, $C_4$ alkyl refers to an alkyl group that has 4 carbon atoms. $C_1$-$C_6$ alkyl refers to an alkyl group having a number of carbon atoms encompassing the entire range (e.g., 1 to 6 carbon atoms), as well as all subgroups (e.g., 1-6, 2-7, 1-5, 3-6, 1, 2, 3, 4, 5, and 6 carbon atoms). Nonlimiting examples of alkyl groups include, methyl, ethyl, n-propyl, isopropyl, n-butyl, sec-butyl (2-methylpropyl), and t-butyl. Unless otherwise indicated, an alkyl group can be an unsubstituted alkyl group or a substituted alkyl group. The term "hydroxyalkyl" refers to an alkyl group substituted with 1-3 —OH moieties, e.g., 1, 2, or 3 —OH moieties. For example, $C_1$-$C_6$ hydroxyalkyl refers to a $C_1$-$C_6$ alkyl group substituted with 1, 2, or 3 —OH groups, such as a $C_1$-$C_6$ alkyl group substituted with 1 —OH group.

The term "alkylene" used herein refers to an alkyl group having a substituent. For example, an alkylene group can be —$CH_2CH_2$— or —$CH_2$—. The term $C_n$ means the alkylene group has "n" carbon atoms. For example, $C_{1-6}$ alkylene refers to an alkylene group having a number of carbon atoms encompassing the entire range, as well as all subgroups, as previously described for "alkyl" groups. Unless otherwise indicated, an alkylene group can be an unsubstituted alkylene group or a substituted alkylene group.

As used herein, the term "alkenyl" refers to straight chain or branched chain unsaturated hydrocarbon groups containing from 2 to 6 carbon atoms having at least one carbon to carbon double bond.

As used herein, the term "alkynyl" refers to a straight chain or branched chain unsaturated hydrocarbon groups having the indicated number of carbon atoms and at least one triple bond. Examples of a $C_2$-$C_6$ alkynyl group include, but are not limited to, acetylene, propyne, 1-butyne, 2-butyne, 1-pentyne, 2-pentyne, 1-hexyne, 2-hexyne, and 3-hexyne.

As used herein, the terms "cycloalkane" and "cycloalkyl" refer to an aliphatic cyclic hydrocarbon group containing three to ten carbon atoms (e.g., 3, 4, 5, 6, 7, 8, 9, or 10 carbon atoms). The term $C_n$ means the cycloalkyl group has "n" carbon atoms. For example, $C_6$ cycloalkyl refers to a cycloalkyl group that has 6 carbon atoms in the ring. $C_3$-$C_{10}$ cycloalkyl refers to cycloalkyl groups having a number of carbon atoms encompassing the entire range (e.g., 3 to 10 carbon atoms), as well as all subgroups (e.g., 3-4, 3-5, 3-6, 3-7, 3-8, 3-9, 3-10, 4-5, 4-6, 4-7, 4-8, 49-, 4-10, 5-6, 5-7, 5-8, 5-9, 5-10, 6-7, 6-8, 7-8, 6-9, 7-9, 8-9, 6-10, 7-10, 8-10, 9-10, 3, 4, 5, 6, 7, 8, 9, and 10 carbon atoms). Nonlimiting examples of cycloalkyl groups include cyclopropyl, cyclobutyl, cyclopentyl, cyclohexyl, cycloheptyl, and cyclooctyl. Unless otherwise indicated, a cycloalkyl group can be an unsubstituted cycloalkyl group or a substituted cycloalkyl group. The cycloalkyl groups described herein can be isolated or fused to another cycloalkyl group, a heterocycloalkyl group, an aryl group and/or a heteroaryl group. When a cycloalkyl group is fused to another cycloalkyl group, then each of the cycloalkyl groups can contain three to ten carbon atoms unless specified otherwise. Unless otherwise indicated, a cycloalkyl group can be unsubstituted or substituted.

As used herein, the terms "heterocycle" or "heterocycloalkyl" are defined similarly as cycloalkyl, except the ring contains one to three heteroatoms independently selected from oxygen, nitrogen, and sulfur. In particular, the term "heterocycloalkyl" refers to a ring containing a total of three to seven atoms (e.g., three to seven, or five to seven), of which 1, 2, or three of those atoms are heteroatoms independently selected from the group consisting of oxygen, nitrogen, and sulfur, and the remaining atoms in the ring are carbon atoms. Nonlimiting examples of heterocycloalkyl groups include piperidine, pyrazolidine, tetrahydrofuran, tetrahydropyran, dihydrofuran, morpholine, and the like.

Cycloalkyl and heterocycloalkyl groups can be saturated or partially unsaturated ring systems optionally substituted with, for example, one to three groups, independently selected from halo, OH, C(O)—$C_{1-6}$ alkyl, $C(O)NH_2$, and $C_{5-6}$ cycloalkyl. Heterocycloalkyl groups optionally can be further N-substituted with alkyl, alkylene-OH, alkylenearyl, and alkyleneheteroaryl. The heterocycloalkyl groups described herein can be isolated or fused to another heterocycloalkyl group, a cycloalkyl group, an aryl group, and/or a heteroaryl group. When a heterocycloalkyl group is fused to another heterocycloalkyl group, then each of the heterocycloalkyl groups can contain three to seven total ring atoms, and one to three heteroatoms, e.g., 6 to 14 total ring atoms, such as 12, 13, or 14 ring atoms, and one to three heteroatoms. Unless otherwise indicated, a heterocycloalkyl group can be unsubstituted or substituted.

As used herein, the term "aryl" refers to a monocyclic or bicyclic aromatic ring having 5 to 10 total ring carbon atoms, such as phenyl. Unless otherwise indicated, an aryl group can be unsubstituted or substituted with one or more, and in particular one to four groups independently selected from, for example, halo, OH, C(O)—$C_{1-6}$ alkyl, $C(O)NH_2$, and $C_{5-6}$ cycloalkyl. Aryl groups can be isolated (e.g., phenyl) or fused to another aryl group (e.g., naphthyl, anthracenyl), a cycloalkyl group (e.g. tetraydronaphthyl), a heterocycloalkyl group, and/or a heteroaryl group. Exemplary aryl groups include, but are not limited to, phenyl, chlorophenyl, methylphenyl, methoxyphenyl, trifluoromethylphenyl, nitrophenyl, 2,4-methoxychlorophenyl, and the like.

As used herein, the term "heteroaryl" refers to a monocyclic or bicyclic aromatic ring having 5 to 10 total ring atoms, and containing one to four heteroatoms selected from nitrogen, oxygen, and sulfur atom in the aromatic ring. Unless otherwise indicated, a heteroaryl group can be unsubstituted or substituted with one or more, and in particular one to four, substituents selected from, for example, halo, OH, C(O)—$C_{1-6}$ alkyl, $C(O)NH_2$, and $C_{5-6}$ cycloalkyl. In embodiments, the heteroaryl group is substituted with one or more of alkyl and alkoxy groups. Examples of heteroaryl groups include, but are not limited to, thienyl, furyl, pyridyl, pyrrolyl, oxazolyl, triazinyl, triazolyl, isothiazolyl, isoxazolyl, imidazolyl, pyrazinyl, pyrimidinyl, thiazolyl, and thiadiazolyl.

As used herein, the term "substituted," when used to modify a chemical functional group, refers to the replacement of at least one hydrogen radical on the functional group with a substituent. Substituents can include, but are not limited to, alkyl, cycloalkyl, alkenyl, cycloalkenyl, alkynyl, heterocycloalkyl, aryl, heteroaryl, hydroxyl, oxy, alkoxy, heteroalkoxy, ester, thioester, carboxy, cyano, nitro, amino, amido, acetamide, and halo (e.g., fluoro, chloro, bromo, or iodo). When a chemical functional group includes more than one substituent, the substituents can be bound to the same carbon atom or to two or more different carbon atoms.

As used herein, the phrase "substituted or unsubstituted" means unsubstituted (e.g., substituted with a H) or substituted with a group e.g., as defined herein. It is understood that substitution at a given atom is limited by valency. The use of a substituent (radical) prefix name such as alkyl without the modifier "unsubstituted" or "substituted" is understood to mean that the particular substituent is unsubstituted.

The term "pharmaceutically-acceptable salt" refers to an acid or base salt of a compound of the invention, which salt possesses the desired antiviral activity and is neither biologically nor otherwise undesirable. The present disclosure also includes prodrugs (ester, amide, carbamate, carbonate, ether, imine, phosphate, etc. derivatives) of the disclosed compounds as well as deuterated derivatives of the compounds.

In some embodiments, particularly preferred X moieties include the following structures in the brackets below (where the oxygen from formula (I) is depicted for clarity):

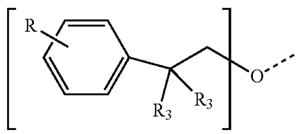

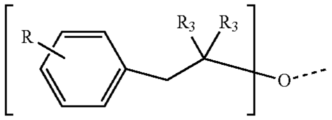

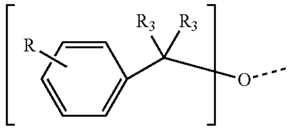

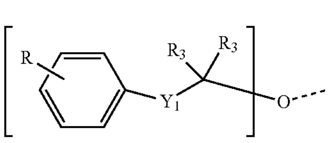

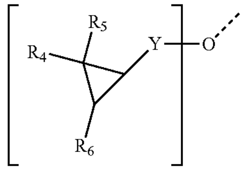

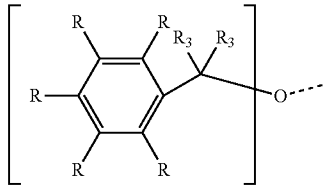

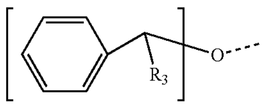

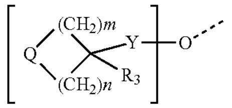

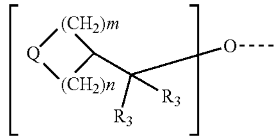

where m and n are 0, 1, 2, or 3, provided that at least one of n or m is 1; p is 0, 1-5; R, when present, is a halogen; $Y_i$ is O or $S(=O)_o$ where o is 0, 1, or 2; Y is $(CR_iR_j)_o$, where o can be 0 (meaning Y is not present and the oxygen is directly bonded to carbon of the ring) or 1 (meaning $Y=CR_iR_j$ where $R_i$ and $R_j$ can both be H, or both methyl, or one H and the other methyl, or deuterated derivatives thereof, o can also be 3 or more, but 0 and 1 are preferred; each Q is selected from the group consisting of branched or unbranched alkyls (e.g., methyl, ethyl, propyl, isopropyl, butyl, isobutyl), $C(CH_3)_2$, CHF, $CF_2$, or $CHCF_3$, but can also be O or $S(=O)_o$ where o is 0, 1, or 2; Q can also be a carbon to which different groups are attached to, for example, Q can be $CR_wR_x$ where each $R_w$ is —H or alkyl, aryl alkyl, phenyl or deuterated phenyl, substituted phenyl, or F, and $R_x$=H or alkyl, or F; each $R_3$ is selected from the group consisting of —OH, —H, branched or unbranched alkyls (e.g., methyl, ethyl, butyl, isobutyl), substituted or unsubstituted aryls (e.g., phenyl, substituted phenyl), arylalkyl (e.g., benzyl or group where the aryl is naphthyl), and the like, and preferably where at least one or both $R_3$ moieties are alkyls (more preferably $C_1$-$C_3$ alkyls), or where one $R_3$ is an alkyl and one $R_3$ an —OH group; each $R_4$, $R_5$, and R6 is independently selected from the group consisting of —H, branched or unbranched alkyls (e.g., methyl, ethyl, butyl, isobutyl), substituted or unsubstituted aryls (e.g., phenyl, substituted phenyl), arylalkyl (e.g. benzyl or group where the aryl is naphthyl), and the like, substituted or unsubstituted aryl (e.g., phenyl, substituted phenyl), arylalkyl, and cyclopropane ring (cis and/or trans), where each $R_4$ could also be a halogen (F, Cl, Br); each $R_s$ is preferably —H, alkyl, or halogen (F, Cl, Br); and each $R_6$ is preferably —H, branched or unbranched alkyl, halogenated alkyl, substituted or unsubstituted aryl (e.g., phenyl, substituted phenyl), arylalkyl, cyclopropane ring (cis and/or trans), or cyclohexane or substituted cyclohexanes or bicyclic or tricyclic rings.

Particular cycloalkane compounds have a structure including:

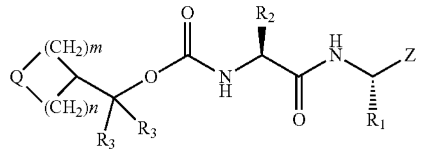

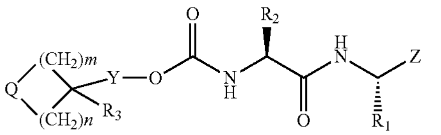

where the substituents are defined as above, and where each $R_1$ is glutamine or imidazole surrogate:

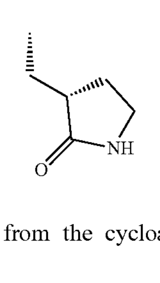

Particular examples from the cycloalkane series have a structure including:

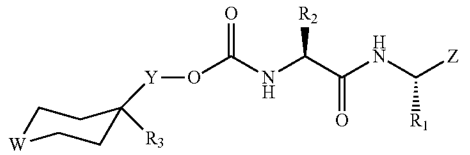

i.e., where m and n each equal 2, and W is $CF_2$, $CHCF_3$, O, S, S(=O), $SO_2$, or $C_1$-$C_6$ alkyl; and the structure:

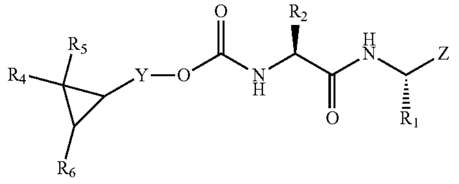

where m is 1 and n is 0.

Macrocyclic derivatives of the cycloalkane compounds are also contemplated:

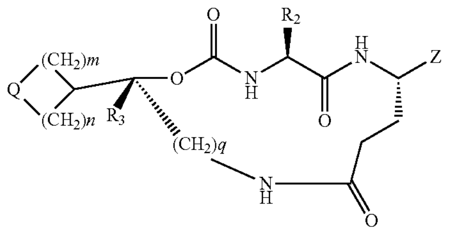

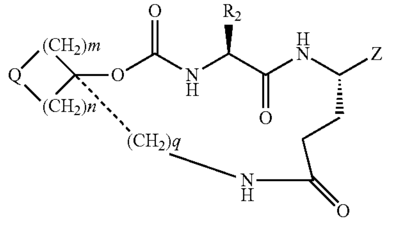

where m and n are each 0, 1, 2, or 3, where at least one of m or n is 1, and each q is 1-6, with the remaining substituents defined above.

In one or more embodiments, particularly preferred [X] groups comprise the following structures shown in bracket with the oxygen linkage from formula (I) depicted for clarity:

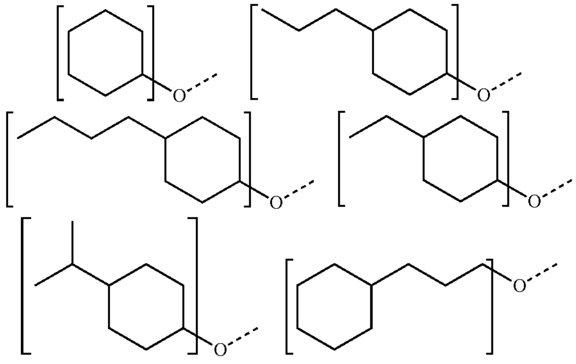

-continued

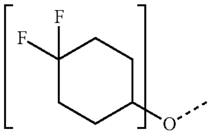

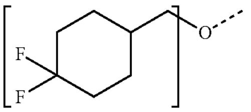

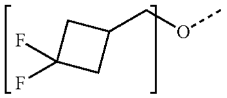

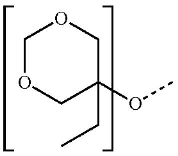

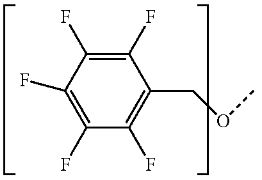

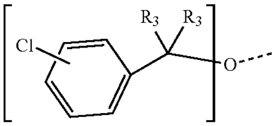

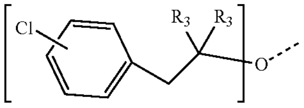

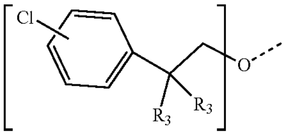

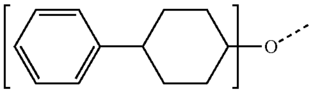

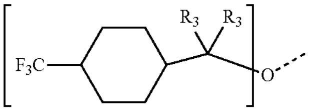

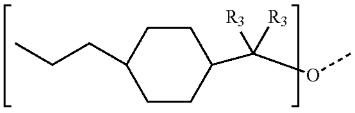

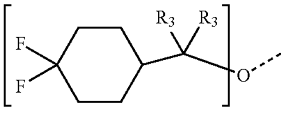

Prophylactic and/or therapeutic compositions with specific or broad-spectrum antiviral activities are also disclosed. Combinations of one or more of the foregoing compounds can also be used in the invention. The compositions comprise an antiviral compound described herein dispersed in a pharmaceutically-acceptable carrier. The term carrier is used herein to refer to diluents, excipients, vehicles, and the like, in which the antiviral may be dispersed for administration. Suitable carriers will be pharmaceutically acceptable. As used herein, the term “pharmaceutically acceptable” means not biologically or otherwise undesirable, in that it can be administered to a subject without excessive toxicity, irritation, or allergic response, and does not cause unacceptable biological effects or interact in a deleterious manner with any of the other components of the composition in which it is contained. A pharmaceutically-acceptable carrier would be selected to minimize any degradation of the compound or other agents and to minimize any adverse side effects in the subject. Pharmaceutically-acceptable ingredients include those acceptable for veterinary use as well as human pharmaceutical use, and will depend on the route of administration. For example, compositions suitable for administration via injection are typically solutions in sterile isotonic aqueous buffer. Exemplary carriers include aqueous solutions such as normal (n.) saline (~0.9% NaCl), phosphate buffered saline (PBS), sterile water/distilled autoclaved water (DAW), various oil-in-water or water-in-oil emulsions, as well as dimethyl sulfoxide (DMSO) or other acceptable vehicles, and the like.

The composition can comprise a therapeutically effective amount of the compound dispersed in the carrier. As used herein, a “therapeutically effective” amount refers to the amount that will elicit the biological or medical response of a tissue, system, or subject that is being sought by a researcher or clinician, and in particular elicit some desired therapeutic or prophylactic effect as against the viral infection by slowing and/or inhibiting 3CL protease activity and/or viral replication. One of skill in the art recognizes that an amount may be considered therapeutically “effective” even if the condition is not totally eradicated or prevented, but it or its symptoms and/or effects are improved or alleviated partially in the subject. In some embodiments, the composition will comprise from about 5% to about 95% by weight of an antiviral compound described herein, and preferably from about 30% to about 90% by weight of the antiviral compound, based upon the total weight of the composition taken as 100% by weight. In some embodiments, combinations of more than one type of the described antiviral compounds can be included in the composition, in which case the total levels of all such compounds will preferably fall within the ranges described above.

Other ingredients may be included in the composition, such as adjuvants, other active agents, preservatives, buffering agents, salts, other pharmaceutically-acceptable ingredients. The term “adjuvant” is used herein to refer to substances that have immunopotentiating effects and are added to or co-formulated in a therapeutic composition in order to enhance, elicit, and/or modulate the innate, humoral, and/or cell-mediated immune response against the active ingredients. Other active agents that could be included in the composition include other antiviral compounds (e.g., cathepsins) or any immunogenic active components (e.g., antigens) such as those that resemble a disease-causing microorganism or infectious agent, and/or are made from weakened or killed forms of the same, its toxins, subunits, particles, and/or one of its surface proteins, such that it provokes an immune response to that microorganism or infectious agent. In addition to live, modified, or attenuated vaccine components, active agents using synthetic peptides, carbohydrates, or antigens can also be used.

Compositions according to the embodiments disclosed herein are useful in treating and/or preventing viral infection from coronaviruses as well as against other viruses that belong to the picornavirus-like supercluster, including caliciviruses and picornaviruses in a subject. Thus, embodiments described herein have broad-spectrum therapeutic and/or prophylactic uses. The terms “therapeutic” or “treat,” as used herein, refer to processes that are intended to produce a beneficial change in an existing condition (e.g., viral infection, disease, disorder) of a subject, such as by reducing the severity of the clinical symptoms and/or effects of the infection, and/or reducing the duration of the infection/symptoms/effects. The terms “prophylactic” or “prevent,” as used herein, refer to processes that are intended to inhibit or ameliorate the effects of a future viral infection or disease to which a subject may be exposed (but is not currently infected with). In some cases, the composition may prevent the development of observable morbidity from viral infection (i.e., near 100% prevention). In other cases, the composition may only partially prevent and/or lessen the extent of morbidity due to the viral infection (i.e., reduce the severity of the symptoms and/or effects of the infection, and/or reduce the duration of the infection/symptoms/effects). In either case, the compounds are still considered to "prevent" the target infection or disease.

In use, a therapeutically-effective amount of an antiviral compound is administered to a subject. In some embodiments, a composition comprising a therapeutically-effective amount of an antiviral compound is administered to a subject. Regardless, the compound or pharmaceutically acceptable salt thereof will preferably be administered to the subject in an amount sufficient to provide antiviral compound levels (independent of salt, if any) of from about 0.1 mg to about 1,000 mg of compound per kg of body weight of the subject, preferably from about 1 mg/kg to about 100 mg/kg of body weight of the subject, and more preferably from about 10 mg/kg to about 50 mg/kg of body weight of the subject. Thus, it will be appreciated that in the case of compound salts, for example, the formulation may be administered in amounts greater than the above ranges to provide sufficient levels of the active compound.

In some embodiments, the subject is afflicted with or suffering from a condition (e.g., infection, disease, or disorder) before the compounds are administered, wherein methods described herein are useful for treating the condition and/or ameliorating the effects of the condition. Preferably, the antiviral compound is administered as soon as possible after infection, preferably within about 7 days from onset of observable symptoms, more preferably within about 5 days from onset of observable symptoms, even more preferably within 3 days from onset of observable symptoms. It will be appreciated that the sooner the compound(s) is administered, the increased chance of successfully reducing effects of the viral infection. In other embodiments, the subject is free of a given condition before administering the compound, wherein the methods described herein are useful for preventing the occurrence or incidence of the condition and/or preventing the effects of the condition, as described above. The disclosed embodiments are suitable for various routes of administration, depending upon the particular carrier and other ingredients used. For example, the prophylactic and/or therapeutic compounds or compositions can be injected intramuscularly, subcutaneously, intradermally, or intravenously. They can also be administered via mucosa such as intranasally or orally. The compounds or compositions can also be administered through the skin via a transdermal patch.

In some embodiments, the compound or compositions can be provided in unit dosage form in a suitable container. The term "unit dosage form" refers to a physically discrete unit suitable as a unitary dosage for human or animal use. Each unit dosage form may contain a predetermined amount of the inventive compound (and/or other active agents) in the carrier calculated to produce a desired effect. In other embodiments, the compound can be provided separate from the carrier (e.g., in its own vial, ampule, sachet, or other suitable container) for on-site mixing before administration to a subject.

A kit comprising the antiviral compound(s) is also disclosed herein. The kit further comprises instructions for administering the compound to a subject. The antiviral compound(s) can be provided as part of a dosage unit, already dispersed in a pharmaceutically-acceptable carrier, or it can be provided separately from the carrier. The kit can further comprise instructions for preparing the antiviral compounds for administration to a subject, including for example, instructions for dispersing the compounds in a suitable carrier.

It will be appreciated that therapeutic and prophylactic methods described herein are applicable to humans as well as any suitable animal, including, without limitation, dogs, cats, and other pets, as well as, rodents, primates, horses, cattle, pigs, etc. The methods can be also applied for clinical research and/or study. Additional advantages of the various embodiments of the disclosure will be apparent to those skilled in the art upon review of the disclosure herein and the working examples below. It will be appreciated that the various embodiments described herein are not necessarily mutually exclusive unless otherwise indicated herein. For example, a feature described or depicted in one embodiment may also be included in other embodiments, but is not necessarily included. Thus, the present invention encompasses a variety of combinations and/or integrations of the specific embodiments described and claimed herein.

As used herein, the phrase "and/or," when used in a list of two or more items, means that any one of the listed items can be employed by itself or any combination of two or more of the listed items can be employed. For example, if a composition is described as containing or excluding components A, B, and/or C, the composition can contain or exclude A alone; B alone; C alone; A and B in combination; A and C in combination; B and C in combination; or A, B, and C in combination.

The present description also uses numerical ranges to quantify certain parameters relating to various embodiments of the invention. It should be understood that when numerical ranges are provided, such ranges are to be construed as providing literal support for claim limitations that only recite the lower value of the range as well as claim limitations that only recite the upper value of the range. For example, a disclosed numerical range of about 10 to about 100 provides literal support for a claim reciting "greater than about 10" (with no upper bounds) and a claim reciting "less than about 100" (with no lower bounds).

Abbreviations: ORF, open reading frame; EDCI, 1-ethyl-3-(3-dimethylaminopropyl) carbodiimide; HOBt, N-hydroxybenzotriazole; DIEA, diisopropylethyl amine; DTT, dithiothreitol; DMSO, dimethyl sulfoxide; DMF, N,N-dimethylformamide; DMP, Dess-Martin periodinane; DSC, N,N'-disuccinimidyl carbonate; TEA, Triethyl amine; CDI, carbonyl diimidazole; MNV, murine norovirus; MOI, multiplicity of infection; CPE, cytopathic effects; $TCID_{50}$, the 50% tissue culture infectious dose; $IC_{50}$, the 50% inhibitory concentration in the enzyme assay; $EC_{50}$, the 50% effective concentration in cell culture; $CC_{50}$, 50% cytotoxic concentration in cell-based assays; GESAMT, general efficient structural alignment of macromolecular targets; RMSD, root mean square deviation; XDS, X-ray detector software; MME, monomethyl ether; PK, pharmacokinetics.

EXAMPLES

The following examples set forth methods in accordance with the invention. It is to be understood, however, that these examples are provided by way of illustration and nothing therein should be taken as a limitation upon the overall scope of the invention. Except where noted, precursor, intermediate, and final compounds described in the synthesis reactions below are independently numbered in each Example. Structures are indicated in the Tables below for avoidance of doubt.

Example 1

SARS-CoV-2 3CLpro is a homodimer with a catalytic Cys-His dyad ($Cys^{145}$-$His^{41}$) and an extended binding cleft. Substrate specificity profiling studies have shown that the protease displays a strong preference for a -haa-N-Leu-Gln-aa sequence, where aa is a small amino acid, haa is a hydrophobic amino acid, and N is solvent-exposed and fairly diverse (V/T/K), corresponding to the subsites -$S_4$-$S_3$-$S_2$-$S_1$-$S_1$'-. Cleavage is at the $P_1$-$P_{1'}$ scissile bond. The 3D structure of SARS-CoV-2 3CLpro is similar to that of SARS-CoV 3CLpro, however, the $S_2$ subsite of SARS-CoV-2 3CLpro displays considerable plasticity and can accommodate natural and unnatural amino acids with smaller side chains. High-resolution crystal structures with bound inhibitors have been determined, enabling the use of structure-guided approaches in the design of inhibitors. In continuing our foray in this area, we report herein the results of preliminary studies related to the inhibition of SARS-CoV-2 protease by a series of inhibitors (I) that incorporate in their structure a conformationally-constrained cyclohexane moiety envisaged to exploit new chemical space and to optimally engage in favorable binding interactions with the active site of the protease.

Materials and Methods.

Synthesis of 3CLpro compounds. Chemistry. Compounds 6a-k and 7a-k were synthesized as illustrated in Scheme 1 (FIG. 1) and are listed in Table 1 and Table 2. Briefly, the alcohol inputs were reacted with (L) leucine isocyanate methyl ester or (L) cyclohexylalanine isocyanate methyl ester to yield dipeptides 2 which were then hydrolyzed to the corresponding acids with lithium hydroxide in aqueous tetrahydrofuran. Subsequent coupling of the acids to glutamine surrogate methyl ester 8 yielded compounds 4. Lithium borohydride reduction yielded alcohols 5 which were then oxidized to the corresponding aldehydes 6 with Dess-Martin periodinane reagent. The bisulfite adducts 7 were generated by treatment with sodium bisulfite in aqueous ethanol and ethyl acetate.

Synthesis of 3CLpro Inhibitors

General. Reagents and dry solvents were purchased from various chemical suppliers (Sigma-Aldrich, Acros Organics, Chem-Impex, TCI America, Oakwood chemical, APExBIO, SynQuest, Fisher and Bachem) and were used as obtained. Silica gel (230-450 mesh) used for flash chromatography was purchased from Sorbent Technologies (Atlanta, GA). Thin layer chromatography was performed using Analtech silica gel plates. Visualization was accomplished using UV light and/or iodine. NMR spectra were recorded in $CDCl_3$ or dimethyl sulfoxide (DMSO)-$d_6$ using Varian XL-400 spectrometer. Melting points were recorded on a Mel-Temp apparatus and are uncorrected. High resolution mass spectrometry (HRMS) was performed at the University of Kansas Mass Spectrometry lab using LCT premier mass spectrometer (Waters, Milford, MA) equipped with a time of flight mass analyzer and an electrospray ion source. The purity of the compounds was determined by high-performance liquid chromatography (HPLC) using a waters Alliance HPLC system with a reverse phase column (Symmetry® C 18 3.5 μm, 4.6×75 mm) at 254 nm and was >95%. Gradient was started with Methanol 60%: Water 40% to Methanol 99%: Water 1% over period of 15 minutes, mobile phase flow rate 1.0 mL/min.

Synthesis of amino acid methyl ester isocyanates. General procedure. Amino acid methyl ester hydrochloride (100 mmol) was placed in an oven dried RB flask (500 mL) and then dried overnight on the vacuum pump. The flask was flushed with nitrogen, and dry dioxane (200 mL) was added followed by trichloromethyl chloroformate (150 mmol), and the stirring reaction mixture was refluxed for 10 h. The solvent was removed on the rotary evaporator, and the residue was vacuum distilled to yield pure isocyanate as a colorless oil.

methyl (S)-2-isocyanato-4-methylpentanoate, (Yield 66%), $^1$H NMR (400 MHz, $cdcl_3$) δ 4.08-4.00 (m, 1H), 3.81 (s, 3H), 1.91-1.76 (m, 1H), 1.73-1.56 (m, 2H), 1.04-0.89 (m, 6H).

methyl (S)-3-cyclohexyl-2-isocyanatopropanoate, (Yield 68%), $^1$H NMR (400 MHz, DMSO-$d_6$) δ 4.38 (ddd, J=9.5, 4.6, 1.2 Hz, 1H), 3.74 (s, 3H), 1.80-1.50 (m, 8H), 1.50-1.35 (m, 1H), 1.30-1.06 (m, 3H), 1.01-0.77 (m, 3H).

Synthesis of amino acid carbamate esters 2. General procedure. A solution of alcohol (20 mmol) in dry acetonitrile (15 mL) was treated with triethylamine (40 mmol), followed by the amino acid methyl ester isocyanate (20 mmol). The resulting reaction mixture was refluxed for 2 h with stirring and then allowed to cool to room temperature. The solution was concentrated, and the residue was taken up in ethyl acetate (100 mL). The organic layer was washed with 5% HCl (2×25 mL) and brine (25 mL). The organic layer was dried over anhydrous sodium sulfate, filtered, and concentrated to yield a crude product as a yellow-colored oil. Purification of the crude oil by flash chromatography yielded ester 2 as a colorless oil.

methyl ((cyclohexyloxy)carbonyl)-L-leucinate (2a). Yield (62.5%). $^1$H NMR (400 MHz, DMSO-$d_6$) δ 7.46 (d, J=7.9 Hz, 1H), 4.46 (dd, J=8.9, 4.9 Hz, 1H), 4.02 (ddd, J=10.2, 7.9, 4.9 Hz, 1H), 3.61 (s, 3H), 1.84-1.75 (m, 2H), 1.68 (s, 2H), 1.62-1.48 (m, 1H), 1.42 (ddd, J=13.6, 8.9, 4.8 Hz, 1H), 1.38-1.25 (m, 4H), 1.29 (s, 1H), 1.19 (d, J=10.4 Hz, 1H), 0.86 (dd, J=12.5, 6.5 Hz, 7H).

methyl (((4-ethylcyclohexyl)oxy)carbonyl)-L-leucinate (2b). Yield (64.0%). $^1$H NMR (400 MHz, DMSO-$d_6$) δ 7.45 (dd, J=16.7, 8.0 Hz, 1H), 4.39 (tt, J=11.0, 4.3 Hz, 1H), 4.02 (ddt, J=10.2, 7.9, 5.3 Hz, 1H), 3.61 (s, 3H), 1.94-1.86 (m, 2H), 1.79-1.36 (m, 6H), 1.34-1.04 (m, 5H), 0.97 (ddd, J=13.2, 3.5, 1.6 Hz, 1H), 0.95-0.75 (m, 9H).

methyl (((4-propylcyclohexyl)oxy)carbonyl)-L-leucinate (2c). Yield (67.0%). $^1$H NMR (400 MHz, DMSO-$d_6$) δ 7.44 (dd, J=18.5, 8.0 Hz, 1H), 4.71 (d, J=14.5 Hz, 1H), 4.38 (tt, J=11.0, 4.2 Hz, 1H), 4.02 (ddd, J=10.2, 7.9, 5.0 Hz, 1H), 3.61 (s, 3H), 3.31 (d, J=0.5 Hz, 1H), 1.93-1.85 (m, 1H), 1.77-1.68 (m, 2H), 1.67-1.50 (m, 1H), 1.53-1.36 (m, 2H), 1.28 (ddt, J=15.4, 11.5, 4.3 Hz, 4H), 1.25-1.08 (m, 3H), 1.01-0.94 (m, 1H), 0.98-0.81 (m, 9H).

methyl (((4-isopropylcyclohexyl)oxy)carbonyl)-L-leucinate (2d). Yield (62.0%). $^1$H NMR (400 MHz, DMSO-$d_6$) δ 7.47 (d, J=7.9 Hz, 1H), 4.37 (tt, J=11.1, 4.3 Hz, 1H), 4.02 (ddd, J=10.2, 7.9, 4.9 Hz, 1H), 3.61 (s, 3H), 1.93 (d, J=11.7 Hz, 2H), 1.83-1.66 (m, 2H), 1.65-1.49 (m, 1H), 1.48-1.34 (m, 2H), 1.26 (dq, J=15.7, 8.5, 6.2 Hz, 2H), 1.13-0.95 (m, 3H), 0.95-0.76 (m, 13H).

methyl (((4-butylcyclohexyl)oxy)carbonyl)-L-leucinate (2e). Yield (69.0%). $^1$H NMR (400 MHz, DMSO-$d_6$) δ 7.44 (dd, J=18.7, 8.0 Hz, 1H), 4.70 (q, J=6.9, 3.8 Hz, 1H), 4.38 (tt, J=11.0, 4.2 Hz, 1H), 4.10-3.91 (m, 1H), 3.61 (d, J=1.6 Hz, 3H), 1.97-1.82 (m, 1H), 1.82-1.66 (m, 2H), 1.66-1.56 (m, 1H), 1.56-1.36 (m, 3H), 1.36-1.08 (m, 9H), 0.95 (td, J=12.8, 11.8, 3.3 Hz, 1H), 0.90-0.75 (m, 9H).

methyl ((3-cyclohexylpropoxy)carbonyl)-L-leucinate (2f). Yield (63.5%). $^1$H NMR (400 MHz, DMSO-$d_6$) δ 7.51 (d, J=8.0 Hz, 1H), 4.03 (ddd, J=10.3, 8.0, 4.8 Hz, 1H), 3.62

(s, 3H), 1.76-1.57 (m, 6H), 1.53 (ddt, J=8.6, 6.6, 3.2 Hz, 2H), 1.48-1.35 (m, 1H), 1.28-1.04 (m, 9H), 0.86 (dd, J=13.6, 6.5 Hz, 8H).

methyl (((5-ethyl-1,3-dioxan-5-yl)oxy)carbonyl)-L-leucinate (2g). Yield (51.0%). $^1$H NMR (400 MHz, DMSO-$d_6$) δ 7.50 (d, J=8.1 Hz, 1H), 4.77 (d, J=5.9 Hz, 1H), 4.61 (d, J=5.9 Hz, 1H), 4.13-4.05 (m, 1H), 4.06-3.98 (m, 1H), 3.69 (dd, J=11.4, 0.8 Hz, 2H), 3.63 (s, 3H), 3.43 (d, J=5.0 Hz, 2H), 1.74-1.63 (m, 1H), 1.63-1.34 (m, 1H), 1.26 (q, J=7.6 Hz, 2H), 0.86 (dd, J=14.0, 6.4 Hz, 6H), 0.76 (t, J=7.6 Hz, 3H).

methyl (((4,4-difluorocyclohexyl)oxy)carbonyl)-L-leucinate (2h). Yield (62.0%). $^1$H NMR (400 MHz, DMSO-$d_6$) δ 7.59 (d, J=8.0 Hz, 1H), 4.89-4.57 (m, 1H), 4.09-3.92 (m, 1H), 3.62 (s, 3H), 2.14-1.87 (m, 4H), 1.82 (tq, J=8.0, 4.2 Hz, 2H), 1.77-1.59 (m, 3H), 1.59-1.49 (m, 1H), 1.48-1.34 (m, 1H), 0.86 (dd, J=12.8, 6.5 Hz, 6H).

methyl (S)-3-cyclohexyl-2-((((4,4-difluorocyclohexyl)oxy)carbonyl)amino)propanoate (2i). Yield (59.0%). $^1$H NMR (400 MHz, DMSO-$d_6$) δ 7.58 (d, J=8.0 Hz, 1H), 4.81-4.64 (m, 1H), 4.06 (td, J=8.9, 5.4 Hz, 1H), 3.62 (s, 3H), 2.11-1.88 (m, 4H), 1.88-1.78 (m, 1H), 1.78-1.55 (m, 7H), 1.49 (tq, J=13.7, 6.9, 5.3 Hz, 2H), 1.39-1.26 (m, 1H), 1.26-1.04 (m, 4H), 0.88 (dt, J=33.1, 11.1 Hz, 2H).

methyl (((4,4-difluorocyclohexyl)methoxy)carbonyl)-L-leucinate (2j). Yield (61.0%). $^1$H NMR (400 MHz, DMSO-$d_6$) δ 7.59 (d, J=8.0 Hz, 1H), 4.83-4.62 (m, 1H), 3.62 (s, 3H), 3.26 (dd, J=6.5, 2.7 Hz, 2H), 2.04-1.90 (m, 5H), 1.90-1.63 (m, 4H), 1.54-1.40 (m, 2H), 1.26-1.07 (m, 1H), 0.87 (dd, J=13.0, 7.0 Hz, 6H).

methyl (((3,3-difluorocyclobutyl)methoxy)carbonyl)-L-leucinate (2k). Yield (63.0%). $^1$H NMR (400 MHz, DMSO-$d_6$) δ 7.56 (d, J=8.2 Hz, 1H), 4.77-4.60 (m, 1H), 3.62 (s, 3H), 3.48-3.40 (m, 2H), 2.60-2.45 (m, 4H), 2.45-2.28 (m, 3H), 2.28-2.14 (m, 1H), 0.87 (dd, J=13.0, 7.0 Hz, 6H).

Synthesis of acids 3. General procedure. A solution of ester 2 (20 mmol) in THE (30 mL) was treated with 1 M LiOH (80 mmol). The reaction mixture was stirred for 3 h at room temperature, and the disappearance of the ester was monitored by TLC. Most of the solvent was removed in vacuo, and the solution was acidified to pH ~2 using 5% hydrochloric acid. The aqueous layer was extracted with ethyl acetate (3×100 mL) and the combined organic layers were dried over anhydrous sodium sulfate, filtered, and concentrated to yield compound 3.

((cyclohexyloxy)carbonyl)-L-leucine (3a). Yield (90.5%). $^1$H NMR (400 MHz, DMSO-$d_6$) δ 12.44 (br s, 1H), 7.28 (d, J=8.2 Hz, 1H), 4.55-4.37 (m, 1H), 3.93 (ddd, J=10.3, 8.2, 4.7 Hz, 1H), 1.80 (dd, J=9.5, 4.9 Hz, 2H), 1.74-1.57 (m, 4H), 1.57-1.38 (m, 2H), 1.36-1.22 (m, 5H), 0.86 (dd, J=12.6, 6.5 Hz, 6H).

(((4-ethylcyclohexyl)oxy)carbonyl)-L-leucine (3b). Yield (87.0%). $^1$H NMR (400 MHz, DMSO-$d_6$) δ 12.44 (br s, 1H), 7.47 (dd, J=16.7, 8.0 Hz, 1H), 4.66-4.52 (m, 1H), 4.08 (ddt, J=10.2, 7.9, 5.3 Hz, 1H), 1.93-1.82 (m, 2H), 1.82-1.30 (m, 6H), 1.30-1.01 (m, 5H), 0.92-0.77 (m, 10H).

(((4-propylcyclohexyl)oxy)carbonyl)-L-leucine (3c). Yield (92.0%). $^1$H NMR (400 MHz, DMSO-$d_6$) δ 12.45 (br s, 1H), 7.26 (dd, J=16.2, 8.2 Hz, 1H), 4.77-4.61 (m, 1H), 4.39 (td, J=11.1, 5.4 Hz, 1H), 3.93 (tt, J=9.5, 5.4 Hz, 1H), 1.89 (d, J=12.0 Hz, 1H), 1.81-1.57 (m, 3H), 1.57-1.37 (m, 4H), 1.37-1.06 (m, 7H), 1.06-0.68 (m, 9H).

(((4-isopropylcyclohexyl)oxy)carbonyl)-L-leucine (3d). Yield (89.5%), mp 83-85° C. $^1$HNMR (400 MHz, DMSO-$d_6$) δ 12.44 (br s, 1H), 7.12 (d, J=8.2 Hz, 1H), 4.36 (tt, J=11.1, 4.2 Hz, 1H), 3.89 (td, J=9.0, 5.2 Hz, 1H), 1.92 (d, J=11.8 Hz, 2H), 1.82-1.55 (m, 4H), 1.55-1.33 (m, 4H), 1.33-1.11 (m, 2H), 1.11-0.93 (m, 4H), 0.93-0.76 (m, 9H).

(((4-butylcyclohexyl)oxy)carbonyl)-L-leucine (3e). Yield (87.0%). $^1$H NMR (400 MHz, DMSO-$d_6$) δ 12.44 (br s, 1H), 7.26 (dd, J=16.4, 8.2 Hz, 1H), 4.71 (d, J=16.3 Hz, 1H), 4.38 (tt, J=11.0, 4.2 Hz, 1H), 3.99-3.84 (m, 1H), 1.89 (dd, J=12.5, 3.4 Hz, 1H), 1.77-1.59 (m, 3H), 1.59-1.36 (m, 4H), 1.36-1.21 (m, 7H), 1.22-1.06 (m, 4H), 0.94 (dd, J=23.6, 11.5 Hz, 1H), 1.06-0.73 (m, 6H).

((3-cyclohexylpropoxy)carbonyl)-L-leucine (3f). Yield (93.0%), mp 48-50° C. $^1$H NMR (400 MHz, DMSO-$d_6$) δ 12.46 (br s, 1H), 7.33 (d, J=8.2 Hz, 1H), 4.02-3.83 (m, 1H), 1.80-1.58 (m, 6H), 1.58-1.49 (m, 2H), 1.49-1.31 (m, 1H), 1.27-1.02 (m, 8H), 0.86 (dd, J=13.8, 6.6 Hz, 9H).

(((5-ethyl-1,3-dioxan-5-yl)oxy)carbonyl)-L-leucine (3g). Yield (51.5%). $^1$H NMR (400 MHz, DMSO-$d_6$) δ 12.52 (br s, 1H), 7.40 (d, J=8.3 Hz, 1H), 4.82 (t, J=5.4 Hz, 1H), 4.63 (d, J=5.9 Hz, 1H), 4.15-4.01 (m, 1H), 4.01-3.92 (m, 1H), 3.80-3.64 (m, 2H), 3.54-3.40 (m, 2H), 1.76-1.60 (m, 1H), 1.60-1.35 (m, 1H), 1.27 (q, J=7.9 Hz, 2H), 0.87 (dd, J=14.1, 6.6 Hz, 6H), 0.77 (t, J=7.6 Hz, 3H).

(((4,4-difluorocyclohexyl)oxy)carbonyl)-L-leucine (3h). Yield (85.0%). $^1$H NMR (400 MHz, DMSO-$d_6$) δ 12.50 (br s, 1H), 7.42 (d, J=8.2 Hz, 1H), 4.87-4.59 (m, 1H), 3.95 (ddd, J=10.2, 8.2, 4.8 Hz, 1H), 2.13-1.87 (m, 4H), 1.87-1.77 (m, 2H), 1.77-1.57 (m, 3H), 1.57-1.36 (m, 2H), 0.87 (dd, J=12.9, 6.5 Hz, 6H).

(S)-3-cyclohexyl-2-((((4,4-difluorocyclohexyl)oxy)carbonyl)amino)propanoic acid (3i). Yield (83.0%). $^1$H NMR (400 MHz, DMSO-$d_6$) δ 12.44 (br s, 1H), 7.41 (d, J=8.2 Hz, 1H), 4.79-4.64 (m, 1H), 4.10-4.00 (m, 1H), 2.09-1.88 (m, 4H), 1.90-1.72 (m, 2H), 1.72-1.54 (m, 6H), 1.54-1.30 (m, 3H), 1.30-1.00 (m, 4H), 1.00-0.66 (m, 2H).

(((4,4-difluorocyclohexyl)methoxy)carbonyl)-L-leucine (3j). Yield (86.5%). $^1$H NMR (400 MHz, DMSO-$d_6$) δ 12.42 (br s, 1H), 7.41 (d, J=8.2 Hz, 1H), 4.80-4.65 (m, 1H), 3.87-3.67 (m, 2H), 2.01-1.88 (m, 5H), 1.86-1.74 (m, 2H), 1.74-1.56 (m, 3H), 1.56-1.29 (m, 2H), 0.86 (dd, J=11.0, 7.0 Hz, 6H).

(((3,3-difluorocyclobutyl)methoxy)carbonyl)-L-leucine (3k). Yield (84.5%). $^1$H NMR (400 MHz, DMSO-$d_6$) δ 12.48 (br s, 1H), 7.39 (d, J=8.2 Hz, 1H), 4.59-4.40 (m, 1H), 3.79-3.62 (m, 2H), 2.64-2.39 (m, 4H), 2.39-2.24 (m, 2H), 2.24-2.10 (m, 2H), 0.87 (dd, J=12.0, 7.2 Hz, 6H).

Synthesis of dipeptidyl esters 4. General procedure. To a solution of compound 3 (10 mmol in dry DMF (20 mL) in an oven dried RB flask (250 mL) was added EDCI (12.5 mmol, 1.25 eq), HOBt (12.5 mmol, 1.25 eq), and the mixture was stirred for 30 min at room temperature. In a separate RB flask, a solution of deprotected glutamine surrogate (10 mmol) in DMF (15 mL) cooled to 0-5° C. was treated with diisopropylethylamine (DIEA) (40 mmol, 4 eq), stirred for 30 min, and then added to the reaction mixture containing acid 3. The reaction mixture was stirred for 24 h while monitoring the reaction by TLC. The solvent was removed, and the residue was dissolved in ethyl acetate (200 mL) and the organic layer was sequentially washed with 10% citric acid (2×40 mL), saturated aqueous $NaHCO_3$ (40 mL), followed by brine (50 mL). The organic layer was dried over anhydrous sodium sulfate, filtered, and concentrated to yield a yellow-colored solid product. Purification by flash chromatography yielded ester 4 as a white solid.

methyl (S)-2-((S)-2-(((cyclohexyloxy)carbonyl)amino)-4-methylpentanamido)-3-((S)-2-oxopyrrolidin-3-yl)propanoate (4a). Yield (50.5%), mp 92-94° C. $^1$H NMR (400 MHz, DMSO-$d_6$) δ 8.37 (d, J=8.1 Hz, 1H), 7.64 (d, J=6.6 Hz, 1H), 7.10 (d, J=8.2 Hz, 1H), 4.55-4.39 (m, 1H), 4.41-4.25 (m, 1H), 4.12-3.94 (m, 1H), 3.62 (s, 3H), 3.23-3.02 (m, 2H), 2.32 (ddq, J=13.6, 11.3, 3.4 Hz, 1H), 2.26-2.01 (m, 2H), 1.78 (t, J=4.7 Hz, 2H), 1.73-1.54 (m, 6H), 1.54-1.45 (m, 1H), 1.45-1.37 (m, 1H), 1.37-1.25 (m, 4H), 1.23-1.11 (m, 1H), 0.87 (dd, J=10.4, 6.6 Hz, 6H).

methyl (S)-2-((S)-2-((((4-ethylcyclohexyl)oxy)carbonyl) amino)-4-methylpentanamido)-3-((S)-2-oxopyrrolidin-3-yl) propanoate (4b). Yield (58.0%), mp 62-64° C. $^1$H NMR (400 MHz, DMSO-$d_6$) S 8.36 (d, J=8.0 Hz, 1H), 7.63 (s, 1H), 7.10 (d, J=8.2 Hz, 1H), 4.53-4.23 (m, 2H), 3.99 (q, J=7.6 Hz, 1H), 3.62 (s, 3H), 3.23-3.01 (m, 2H), 2.37-2.24 (m, 1H), 2.24-1.96 (m, 2H), 1.96-1.78 (m, 2H), 1.78-1.66 (m, 2H), 1.59 (q, J=13.3, 12.0 Hz, 4H), 1.43 (ddd, J=17.6, 10.3, 5.8 Hz, 4H), 1.32-1.12 (m, 5H), 1.12-1.00 (m, 1H), 1.00-0.88 (m, 1H), 0.88-0.78 (m, 6H).

methyl (S)-2-((S)-4-methyl-2-((((4-propylcyclohexyl) oxy)carbonyl)amino)pentanamido)-3-((S)-2-oxopyrrolidin-3-yl)propanoate (4c). Yield (59.0%), mp 58-60° C. $^1$H NMR (400 MHz, DMSO-$d_6$) δ 8.37 (d, J=8.0 Hz, 1H), 7.65 (d, J=18.6 Hz, 1H), 7.08 (d, J=8.0 Hz, 1H), 4.48-4.23 (m, 1H), 4.11-3.91 (m, 1H), 3.62 (s, 3H), 3.24-3.02 (m, 2H), 2.40-2.23 (m, 1H), 2.23-2.00 (m, 2H), 1.88 (d, J=11.3 Hz, 1H), 1.78-1.66 (m, 3H), 1.65-1.51 (m, 3H), 1.51-1.33 (m, 4H), 1.28 (h, J=7.3 Hz, 4H), 1.21-1.08 (m, 4H), 1.03-0.88 (m, 1H), 0.90-0.78 (m, 8H).

methyl (S)-2-((S)-2-((((4-isopropylcyclohexyl)oxy)carbonyl)amino)-4-methylpentanamido)-3-((S)-2-oxopyrrolidin-3-yl)propanoate (4d). Yield (56.0%), mp 70-72° C. $^1$H NMR (400 MHz, DMSO-$d_6$) δ 8.37 (d, J=8.0 Hz, 1H), 7.64 (d, J=8.0 Hz, 1H), 7.10 (d, J=8.1 Hz, 1H), 4.35 (tq, J=11.3, 4.2 Hz, 2H), 4.08-3.92 (m, 1H), 3.62 (s, 3H), 3.25-3.02 (m, 2H), 2.33 (qd, J=10.5, 3.8 Hz, 1H), 2.25-2.02 (m, 2H), 1.96-1.85 (m, 2H), 1.82-1.64 (m, 3H), 1.64-1.51 (m, 3H), 1.41 (ttd, J=10.9, 8.2, 7.7, 3.4 Hz, 4H), 1.19 (q, J=8.0, 7.1 Hz, 2H), 1.02 (dq, J=9.0, 5.7 Hz, 4H), 0.94-0.75 (m, 9H).

methyl (S)-2-((S)-2-((((4-butylcyclohexyl)oxy)carbonyl) amino)-4-methylpentanamido)-3-((S)-2-oxopyrrolidin-3-yl) propanoate (4e). Yield (55.5%), mp 63-65° C. $^1$H NMR (400 MHz, DMSO-$d_6$) δ 8.36 (d, J=8.0 Hz, 1H), 7.63 (s, 1H), 7.10 (d, J=8.2 Hz, 1H), 4.35 (dh, J=11.8, 3.9 Hz, 1H), 4.09-3.90 (m, 1H), 3.61 (s, 3H), 3.24-2.99 (m, 2H), 2.41-2.23 (m, 1H), 2.19-1.99 (m, 2H), 1.87 (d, J=11.6 Hz, 2H), 1.72 (d, J=12.8 Hz, 2H), 1.66-1.52 (m, 3H), 1.52-1.31 (m, 3H), 1.31-1.21 (m, 6H), 1.21-1.06 (m, 4H), 1.06-0.90 (m, 1H), 0.87 (dt, J=10.4, 5.4 Hz, 9H).

methyl (S)-2-((S)-2-(((3-cyclohexylpropoxy)carbonyl) amino)-4-methylpentanamido)-3-((S)-2-oxopyrrolidin-3-yl) propanoate (4f). Yield (59.0%), mp 59-61° C. $^1$H NMR (400 MHz, DMSO-$d_6$) δ 8.38 (d, J=7.9 Hz, 1H), 7.64 (s, 1H), 7.16 (d, J=8.1 Hz, 1H), 4.33 (ddd, J=11.8, 7.8, 4.3 Hz, 1H), 4.11-3.95 (m, 1H), 3.90 (t, J=6.6 Hz, 2H), 3.61 (s, 3H), 3.12 (dtd, J=18.5, 9.4, 7.2 Hz, 2H), 2.31 (ddd, J=12.8, 9.1, 3.8 Hz, 1H), 2.08 (tdd, J=15.3, 10.1, 3.0 Hz, 2H), 1.75-1.57 (m, 8H), 1.57-1.46 (m, 2H), 1.46-1.34 (m, 2H), 1.28-1.05 (m, 6H), 0.87 (dd, J=10.7, 6.6 Hz, 8H).

methyl (S)-2-((S)-2-((((5-ethyl-1,3-dioxan-5-yl)oxy)carbonyl)amino)-4-methylpentanamido)-3-((S)-2-oxopyrrolidin-3-yl)propanoate (4g). Yield (30.5%), mp 60-62° C. $^1$H NMR (400 MHz, DMSO-$d_6$) δ 8.45 (d, J=8.1 Hz, 1H), 7.65 (s, 1H), 7.26 (d, J=8.2 Hz, 1H), 4.82 (d, J=6.0 Hz, 1H), 4.62 (d, J=6.0 Hz, 1H), 4.33 (ddd, J=11.8, 7.8, 4.3 Hz, 1H), 4.10-3.94 (m, 2H), 3.79-3.66 (m, 2H), 3.62 (s, 3H), 3.53-3.40 (m, 1H), 3.13 (dtd, J=18.4, 9.3, 7.3 Hz, 2H), 2.32 (ddd, J=13.8, 11.5, 7.2 Hz, 1H), 2.20-1.98 (m, 2H), 1.75-1.52 (m, 3H), 1.52-1.31 (m, 2H), 1.26 (q, J=7.6 Hz, 2H), 0.88 (dd, J=11.5, 6.5 Hz, 6H), 0.75 (t, J=7.6 Hz, 3H).

methyl (S)-2-((S)-2-((((4,4-difluorocyclohexyl)oxy)carbonyl)amino)-4-methylpentanamido)-3-((S)-2-oxopyrrolidin-3-yl)propanoate (4h). Yield (57.0%), mp 77-79° C. $^1$H NMR (400 MHz, DMSO-$d_6$) δ 8.42 (d, J=7.9 Hz, 1H), 7.64 (s, 1H), 7.26 (d, J=8.1 Hz, 1H), 4.76-4.63 (m, 1H), 4.39-4.21 (m, 1H), 4.10-4.95 (m, 2H), 3.62 (s, 3H), 3.23-3.02 (m, 2H), 2.39-2.24 (m, 2H), 2.17-1.85 (m, 5H), 1.86-1.73 (m, 2H), 1.73-1.54 (m, 4H), 1.53-1.32 (m, 2H), 0.98-0.79 (m, 6H).

methyl (S)-2-((S)-3-cyclohexyl-2-((((4,4-difluorocyclohexyl)oxy)carbonyl)amino)propan-amido)-3-((S)-2-oxopyrrolidin-3-yl)propanoate (4i). Yield (49.0%), mp 80-82° C. $^1$H NMR (400 MHz, DMSO-$d_6$) δ 8.40 (d, J=8.0 Hz, 1H), 7.64 (d, J=6.8 Hz, 1H), 7.24 (d, J=8.1 Hz, 1H), 4.75-4.64 (m, 1H), 4.34 (ddd, J=11.8, 7.8, 4.2 Hz, 1H), 4.12-3.96 (m, 2H), 3.62 (s, 3H), 3.21-3.01 (m, 2H), 2.37-2.25 (m, 1H), 2.25-1.85 (m, 6H), 1.85-1.75 (m, 2H), 1.74-1.51 (m, 9H), 1.51-1.37 (m, 2H), 1.37-1.25 (m, 1H), 1.23-1.04 (m, 2H), 0.98-0.77 (m, 2H).

methyl (S)-2-((S)-2-((((4,4-difluorocyclohexyl)methoxy) carbonyl)amino)-4-methylpentan-amido)-3-((S)-2-oxopyrrolidin-3-yl)propanoate (4j). Yield (52.5%), mp 59-61° C. $^1$H NMR (400 MHz, DMSO-$d_6$) δ 8.41 (d, J=8.9 Hz, 1H), 7.64 (s, 1H), 7.23 (d, J=7.4 Hz, 1H), 4.33 (ddd, J=11.7, 7.7, 4.3 Hz, 1H), 4.08-3.88 (m, 1H), 3.88-3.69 (m, 2H), 3.61 (s, 3H), 3.23-3.04 (m, 2H), 2.36-2.25 (m, 1H), 2.25-1.92 (m, 5H), 1.92-1.68 (m, 4H), 1.68-1.51 (m, 2H), 1.54-1.32 (m, 2H), 1.32-1.10 (m, 3H), 0.87 (dd, J=11.4, 6.5 Hz, 6H).

methyl (2S)-2-((S)-2-((((3,3-difluorocyclobutyl) methoxy)carbonyl)amino)-4-methylpentan-amido)-3-(2-oxopyrrolidin-3-yl)propanoate (4k). Yield (53.0%), mp 55-57° C. $^1$H NMR (400 MHz, DMSO-$d_6$) δ 8.42 (d, J=7.9 Hz, 1H), 7.66 (s, 1H), 7.31 (d, J=8.0 Hz, 1H), 4.33 (ddd, J=11.7, 7.8, 4.3 Hz, 1H), 4.10-3.89 (m, 4H), 3.62 (s, 3H), 3.22-3.04 (m, 2H), 2.70-2.54 (m, 2H), 2.46-2.25 (m, 3H), 2.16-1.99 (m, 2H), 1.61 (ddt, J=15.0, 10.4, 7.0 Hz, 3H), 1.52-1.31 (m, 2H), 0.87 (dd, J=10.9, 6.6 Hz, 6H).

Synthesis of dipeptidyl alcohols 5. General procedure. To a solution of ester 4 (5 mmol) in anhydrous THE (30 mL) was added lithium borohydride (Aldrich) (2 M in THF; 15 mmol) dropwise, followed by dropwise addition of anhydrous methanol (90 mL), and the reaction mixture was stirred at room temperature overnight. The reaction mixture was then acidified by adding 5% HCl and the pH adjusted to ~2. Removal of the solvent left a residue which was taken up in ethyl acetate (100 mL). The organic layer was washed with brine (25 mL), dried over anhydrous sodium sulfate, filtered, and concentrated to yield a crude off-white solid, which was purified by flash chromatography to yield the dipeptidyl alcohol 5 as a white solid.

cyclohexyl ((S)-1-(((S)-1-hydroxy-3-((S)-2-oxopyrrolidin-3-yl)propan-2-yl)amino)-4-methyl-1-oxopentan-2-yl) carbamate (5a). Yield (91.0%), mp 132-134° C. $^1$H NMR (400 MHz, DMSO-$d_6$) δ 7.55 (dd, J=17.6, 9.7 Hz, 1H), 7.12-6.96 (m, 1H), 6.52 (S, 1H), 4.67 (q, J=6.0, 5.5 Hz, 1H), 4.59-4.30 (m, 1H), 3.94 (td, J=8.8, 5.6 Hz, 1H), 3.85-3.70 (m, 1H), 3.42-3.28 (m, 1H), 3.24 (tq, J=10.4, 5.8 Hz, 1H), 3.18-3.00 (m, 1H), 2.31-2.03 (m, 2H), 1.87-1.72 (m, 3H), 1.72-1.62 (m, 3H), 1.56 (dt, J=12.2, 8.4 Hz, 1H), 1.52-1.34 (m, 4H), 1.34-1.12 (m, 5H), 0.85 (dd, J=9.4, 6.6 Hz, 6H).

4-ethylcyclohexyl ((S)-1-(((S)-1-hydroxy-3-((S)-2-oxopyrrolidin-3-yl)propan-2-yl)amino)-4-methyl-1-oxopentan-2-yl)carbamate (5b). Yield (91.0%), mp 100-102° C. $^1$H NMR (400 MHz, DMSO-$d_6$) δ 7.66-7.46 (m, 1H), 7.12-6.96 (m, 1H), 6.52 (s, 1H), 4.66 (t, J=5.4 Hz, 1H), 4.36 (td, J=10.8, 5.4 Hz, 1H), 3.99-3.82 (m, 1H), 3.76 (s, 1H), 3.43-3.29 (m, 1H), 3.22 (dt, J=10.6, 6.2 Hz, 1H), 3.14 (t, J=8.8 Hz, 1H), 3.05 (p, J=8.9, 8.4 Hz, 1H), 2.30-2.05 (m, 2H), 1.93-1.83 (m, 2H), 1.83-1.65 (m, 4H), 1.65-1.52 (m, 2H), 1.52-1.30 (m, 4H), 1.30-1.13 (m, 5H), 1.13-1.03 (m, 1H), 0.95 (t, J=12.9 Hz, 1H), 0.85 (ddd, J=7.5, 5.7, 3.0 Hz, 6H).

4-propylcyclohexyl (( S)-1-(((S)-1-hydroxy-3-((S)-2-oxopyrrolidin-3-yl)propan-2-yl)amino)-4-methyl-1-oxo-pentan-2-yl)carbamate (5c). Yield (92.0%), mp 105-107° C. $^1$H NMR (400 MHz, DMSO-d$_6$) δ 7.66-7.44 (m, 1H), 7.02 (dt, J=27.5, 8.8 Hz, 1H), 6.52 (s, 1H), 4.77-4.54 (m, 1H), 4.36 (tt, J=10.2, 3.8 Hz, 1H), 3.94 (qd, J=8.4, 5.6 Hz, 1H), 3.76 (s, 1H), 3.47-3.30 (m, 1H), 3.22 (dd, J=10.5, 6.6 Hz, 1H), 3.18-3.09 (m, 1H), 3.04 (td, J=9.5, 7.2 Hz, 1H), 2.34-2.04 (m, 2H), 1.89 (d, J=18.0 Hz, 1H), 1.84-1.65 (m, 3H), 1.65-1.51 (m, 2H), 1.41 (dddd, J=27.3, 10.6, 8.4, 4.3 Hz, 5H), 1.28 (dt, J=14.8, 7.5 Hz, 5H), 1.17 (q, J=7.4 Hz, 4H), 1.07-0.90 (m, 1H), 0.86 (ddd, J=9.0, 6.5, 5.2 Hz, 6H).

4-isopropylcyclohexyl ((S)-1-(((S)-1-hydroxy-3-((S)-2-oxopyrrolidin-3-yl)propan-2-yl) amino)-4-methyl-1-oxo-pentan-2-yl)carbamate (5d). Yield (87.0%), mp 77-79° C. $^1$H NMR (400 MHz, DMSO-d$_6$) δ 7.65-7.43 (m, 1H), 7.11-6.95 (m, 1H), 6.59 (d, J=56.3 Hz, 1H), 4.69 (s, 1H), 4.35 (tt, J=11.1, 4.2 Hz, 1H), 3.93 (td, J=9.0, 5.8 Hz, 1H), 3.76 (s, 1H), 3.33 (dd, J=10.6, 5.0 Hz, 1H), 3.22 (dd, J=10.5, 6.5 Hz, 1H), 3.18-3.09 (m, 1H), 3.05 (td, J=9.3, 7.0 Hz, 1H), 2.33-2.03 (m, 2H), 1.97-1.84 (m, 1H), 1.78 (ddd, J=14.1, 11.6, 3.5 Hz, 1H), 1.73-1.62 (m, 2H), 1.62-1.49 (m, 2H), 1.49-1.28 (m, 6H), 1.28-1.11 (m, 2H), 1.12-0.93 (m, 4H), 0.93-0.76 (m, 9H).

4-butylcyclohexyl ((S)-1-(((S)-1-hydroxy-3-((S)-2-oxopyrrolidin-3-yl)propan-2-yl)amino)-4-methyl-1-oxo-pentan-2-yl)carbamate (5e). Yield (86.5%), mp 57-59° C. $^1$H NMR (400 MHz, DMSO-d$_6$) δ 7.65-7.44 (m, 2H), 7.02 (dt, J=26.8, 8.9 Hz, 1H), 4.66 (d, J=4.7 Hz, 2H), 4.36 (tt, J=11.0, 4.2 Hz, 1H), 4.03-3.83 (m, 1H), 3.83-3.67 (m, 1H), 3.33 (s, 1H), 3.28-3.19 (m, 1H), 3.19-3.10 (m, 1H), 3.10 (s, 1H), 2.29-2.05 (m, 2H), 1.94-1.83 (m, 1H), 1.83-1.66 (m, 2H), 1.57 (tt, J=12.3, 6.2 Hz, 2H), 1.50-1.30 (m, 6H), 1.30-1.05 (m, 8H), 1.05-0.74 (m, 9H).

3-cyclohexylpropyl ((S)-1-(((S)-1-hydroxy-3-((S)-2-oxopyrrolidin-3-yl)propan-2-yl)amino)-4-methyl-1-oxo-pentan-2-yl)carbamate (5f). Yield (89.0%), mp 45-47° C. $^1$HNMR (400 MHz, DMSO-d$_6$) δ 7.60 (d, J=8.9 Hz, 1H), 7.54 (s, 1H), 7.18-7.04 (m, 1H), 4.74-4.59 (m, 1H), 4.00-3.85 (m, 4H), 3.83-3.69 (m, 1H), 3.27-3.18 (m, 1H), 3.18-3.01 (m, 2H), 2.27-2.06 (m, 2H), 1.78 (ddd, J=14.6, 11.5, 3.6 Hz, 1H), 1.71-1.57 (m, 5H), 1.57-1.48 (m, 3H), 1.48-1.31 (m, 3H), 1.27-1.03 (m, 6H), 0.85 (dd, J=9.8, 6.6 Hz, 8H).

5-ethyl-1,3-dioxan-5-yl ((S)-1-(((S)-1-hydroxy-3-((S)-2-oxopyrrolidin-3-yl)propan-2-yl) amino)-4-methyl-1-oxo-pentan-2-yl)carbamate (5g). Yield (71.0%), mp 58-60° C. $^1$H NMR (400 MHz, DMSO-d$_6$) δ 7.65 (d, J=8.9 Hz, 1H), 7.53 (s, 1H), 7.21 (d, J=8.3 Hz, 1H), 4.81 (d, J=6.0 Hz, 1H), 4.71-4.58 (m, 2H), 4.12-3.91 (m, 3H), 3.85-3.65 (m, 2H), 3.47 (dd, J=11.4, 2.8 Hz, 2H), 3.22 (dt, J=10.4, 6.1 Hz, 1H), 3.18-2.99 (m, 2H), 2.32-2.06 (m, 2H), 1.78 (ddd, J=14.5, 11.5, 3.5 Hz, 1H), 1.72-1.49 (m, 2H), 1.49-1.31 (m, 2H), 1.31-1.19 (m, 2H), 0.86 (dd, J=10.8, 6.6 Hz, 6H), 0.75 (t, J=7.6 Hz, 3H).

4,4-difluorocyclohexyl ((S)-1-(((S)-1-hydroxy-3-((S)-2-oxopyrrolidin-3-yl)propan-2-yl) amino)-4-methyl-1-oxo-pentan-2-yl)carbamate (5h). Yield (90.0%), mp 126-128° C. $^1$H NMR (400 MHz, DMSO-d$_6$) δ 7.62 (d, J=9.0 Hz, 1H), 7.54 (s, 1H), 7.23 (d, J=8.3 Hz, 1H), 4.77-4.58 (m, 2H), 3.95 (td, J=8.9, 5.6 Hz, 1H), 3.85-3.69 (m, 1H), 3.23 (t, J=8.4 Hz, 1H), 3.09 (dq, J=35.5, 9.0 Hz, 2H), 2.30-2.08 (m, 2H), 2.08-1.85 (m, 4H), 1.85-1.73 (m, 2H), 1.69 (p, J=6.0 Hz, 2H), 1.63-1.49 (m, 2H), 1.49-1.30 (m, 4H), 0.86 (dd, J=10.0, 6.6 Hz, 6H).

4,4-difluorocyclohexyl ((S)-3-cyclohexyl-1-(((S)-1-hy-droxy-3-((S)-2-oxopyrrolidin-3-yl) propan-2-yl)amino)-1-oxopropan-2-yl)carbamate (S$_1$). Yield (93.0%), mp 77-79° C. $^1$H NMR (400 MHz, DMSO-d$_6$) δ 7.61 (d, J=8.2 Hz, 1H), 7.60 (s, 1H), 7.21 (d, J=8.3 Hz, 1H), 4.67-4.43 (m, 2H), 3.97 (td, J=8.9, 5.6 Hz, 1H), 3.75-3.67 (m, 1H), 3.28 (t, J=8.4 Hz, 1H), 3.10 (dq, J=35.5, 9.0 Hz, 2H), 2.37-2.30 (m, 1H), 2.26-1.83 (m, 6H), 1.83-1.77 (m, 2H), 1.77-1.50 (m, 9H), 1.50-1.36 (m, 2H), 1.36-1.23 (m, 1H), 1.23-1.04 (m, 2H), 0.98-0.77 (m, 3H).

(4,4-difluorocyclohexyl)methyl ((S)-1-(((S)-1-hydroxy-3-((S)-2-oxopyrrolidin-3-yl)propan-2-yl)amino)-4-methyl-1-oxopentan-2-yl)carbamate (5j). Yield (90.0%), mp 62-64° C. $^1$H NMR (400 MHz, DMSO-d$_6$) δ 7.60 (d, J=8.9 Hz, 1H), 7.52 (s, 1H), 7.20 (d, J=8.3 Hz, 1H), 4.66 (s, 1H), 3.95 (td, J=8.9, 5.4 Hz, 1H), 3.90-3.69 (m, 3H), 3.23 (d, J=5.7 Hz, 1H), 3.18-3.00 (m, 2H), 2.28-2.07 (m, 2H), 2.06-1.93 (m, 2H), 1.90-1.64 (m, 6H), 1.56 (dq, J=11.9, 8.8 Hz, 2H), 1.51-1.30 (m, 3H), 1.30-1.12 (m, 2H), 0.86 (dd, J=10.5, 6.6 Hz, 6H).

3,3-difluorocyclobutyl)methyl ((2S)-1-(((2S)-1-hydroxy-3-(2-oxopyrrolidin-3-yl)propan-2-yl) amino)-4-methyl-1-oxopentan-2-yl)carbamate (5k). Yield (91.0%), mp 47-49° C. $^1$H NMR (400 MHz, DMSO-d$_6$) δ 7.62 (d, J=8.9 Hz, 1H), 7.52 (s, 1H), 7.28 (d, J=8.2 Hz, 1H), 4.66 (t, J=5.5 Hz, 1H), 4.10-3.85 (m, 3H), 3.76 (d, J=10.8 Hz, 1H), 3.40-3.29 (m, 1H), 3.23 (dt, J=10.4, 6.0 Hz, 1H), 3.18-3.00 (m, 2H), 2.70-2.52 (m, 1H), 2.45-2.27 (m, 3H), 2.28-2.05 (m, 2H), 1.78 (ddd, J=14.6, 11.6, 3.5 Hz, 1H), 1.72-1.50 (m, 2H), 1.47-1.30 (m, 3H), 0.86 (dd, J=9.9, 6.6 Hz, 6H).

Synthesis of dipeptidyl aldehydes 6. General procedure. Compound 5 (5 mmol) was dissolved in excess anhydrous dichloromethane (300 mL) in an oven-dried 500 mL RB flask under a nitrogen atmosphere and cooled to 0° C. Dess-Martin periodinane reagent (15 mmol, 3 eq) was added portion wise over a period of 30 minutes with stirring under a nitrogen atmosphere. The ice bath was removed, and the reaction mixture was stirred at −15° C. for 3 h under a nitrogen atmosphere (monitoring by TLC indicated complete disappearance of the starting material). The reaction mixture was transferred to a separatory funnel and the organic layer was increased to −300 mL by adding fresh dichloromethane. The organic layer was washed thoroughly with 10% aqueous sodium thiosulfate (2×100 mL), followed by saturated aqueous sodium bicarbonate (100 mL), and brine (100 mL) within a period of less than 30 minutes. The organic layer was dried over anhydrous sodium sulfate, filtered, and concentrated to obtain an off-white crude solid which was purified by flash chromatography within an hour to yield the pure aldehyde 6 as a white solid.

cyclohexyl ((S)-4-methyl-1-oxo-1-(((S)-1-oxo-3-((S)-2-oxopyrrolidin-3-yl)propan-2-yl) amino)pentan-2-yl)car-bamate (6a). Yield (57.5%), mp 68-70° C., $^1$H NMR (400 MHz, DMSO-d$_6$) δ 9.40 (s, 1H), 8.43 (d, 7.3 Hz, 1H), 7.64 (d, J=7.0 Hz, 1H), 7.18 (d, J=9.1 Hz, 1H), 4.66 (t, J=5.4 Hz, 1H), 4.56-4.38 (m, 2H), 4.19 (ddd, J=11.4, 7.5, 4.1 Hz, 1H), 4.01-3.86 (m, 1H), 3.86-3.70 (m, 1H), 3.30-2.99 (m, 2H), 2.36-2.05 (m, 2H), 1.96-1.84 (m, 1H), 1.84-1.72 (m, 2H), 1.72-1.53 (m, 3H), 1.46 (dddd, J=18.5, 17.1, 9.3, 4.6 Hz, 2H), 1.24 (dt, J=53.6, 6.7 Hz, 5H), 0.93-0.78 (m, 6H). HRMS (TOF MS ES+) Calc M+H=C$_{20}$H$_{34}$N$_3$O$_5$=396.2498, Found Mass=396.2511, 3.2 ppm Calc M+Na=C$_{20}$H$_{33}$N$_3$O$_5$Na=418.2318, Found Mass=418.2337, 4.6 ppm.

4-ethylcyclohexyl ((S)-4-methyl-1-oxo-1-(((S)-1-oxo-3-((S)-2-oxopyrrolidin-3-yl)propan-2-yl)amino)pentan-2-yl) carbamate (6b). Yield (60.0%), mp 55-57° C., $^1$H NMR (400

MHz, DMSO-$d_6$) δ 9.40 (s, 1H), 8.41 (d, J=7.8 Hz, 1H), 7.64 (d, J=7.8 Hz, 1H), 7.25-7.15 (d, J=7.3 Hz, 1H), 4.77-4.61 (m, 1H), 4.38 (tt, J=11.0, 4.2 Hz, 1H), 4.23-4.09 (m, 1H), 4.09-3.94 (m, 1H), 3.27-3.00 (m, 2H), 2.36-2.07 (m, 2H), 1.96-1.81 (m, 3H), 1.73 (d, J=12.8 Hz, 2H), 1.63 (ddd, J=13.1, 7.4, 2.6 Hz, 2H), 1.46 (ttd, J=13.6, 9.1, 8.5, 4.4 Hz, 3H), 1.31-1.12 (m, 3H), 0.91-0.80 (m, 12H). HRMS (TOF MS ES+) Calc M+H=$C_{22}H_{38}N_3O_5$=424.2811, Found Mass=424.2833, 2.2 mmu Calc M+Na=$C_{22}H_{37}N_3O_5Na$=446.2631, Found Mass=446.2649, 4.1 ppm.

4-propylcyclohexyl ((S)-4-methyl-1-oxo-1-(((S)-1-oxo-3-((S)-2-oxopyrrolidin-3-yl)propan-2-yl)amino)pentan-2-yl)carbamate (6c). Yield (53.0%), mp 50-52° C., $^1$H NMR (400 MHz, DMSO-$d_6$) δ 9.40 (s, 1H), 8.40 (d, J=7.7 Hz, 1H), 7.64 (d, J=7.6 Hz, 1H), 7.15 (d, J=7.5 Hz, 1H), 4.76-4.60 (m, 1H), 4.37 (td, J=10.9, 5.3 Hz, 1H), 4.25-4.07 (m, 1H), 4.09-3.91 (m, 1H), 3.12 (ddt, J=25.3, 17.0, 8.6 Hz, 2H), 2.35-2.04 (m, 2H), 1.95-1.78 (m, 2H), 1.78-1.56 (m, 4H), 1.46 (ddt, J=15.2, 8.7, 4.8 Hz, 4H), 1.28 (h, J=7.1, 6.6 Hz, 5H), 1.21-1.08 (m, 4H), 0.87 (dtd, J=10.3, 7.1, 4.8 Hz, 8H). HRMS (TOF MS ES+) Calc M+H=$C_{23}H_{40}N_3O_5$=438.2968, Found Mass=438.2990, 2.2 mmu Calc M+Na=$C_{23}H_{39}N_3O_5Na$=460.2787, Found Mass=460.2811, 2.4 mmu.

4-isopropylcyclohexyl ((S)-4-methyl-1-oxo-1-(((S)-1-oxo-3-((S)-2-oxopyrrolidin-3-yl)propan-2-yl)amino)pentan-2-yl)carbamate (6d). Yield (57.5%), mp 47-49° C., $^1$H NMR (400 MHz, DMSO-$d_6$) δ 9.40 (s, 1H), 8.41 (d, J=7.7 Hz, 1H), 7.64 (d, J=8.0 Hz, 1H), 7.20 (d, J=8.1 Hz, 1H), 4.36 (tt, J=11.0, 4.2 Hz, 1H), 4.24-4.09 (m, 1H), 4.09-3.88 (m, 1H), 3.28-3.00 (m, 2H), 2.39-2.08 (m, 2H), 2.08-1.85 (m, 3H), 1.81-1.54 (m, 4H), 1.54-1.35 (m, 4H), 1.35-1.11 (m, 2H), 1.02 (s, 3H), 0.94-0.77 (m, 12H). HRMS (TOF MS ES+) Calc M+H=$C_{23}H_{40}N_3O_5$=438.2968, Found Mass=438.2997, 2.9 mmu.

4-butylcyclohexyl ((S)-4-methyl-1-oxo-1-(((S)-1-oxo-3-((S)-2-oxopyrrolidin-3-yl)propan-2-yl)amino)pentan-2-yl) carbamate (6e). Yield (53.0%), mp 45-47° C., $^1$H NMR (400 MHz, DMSO-$d_6$) δ 9.40 (s, 1H), 8.40 (d, J=7.8 Hz, 1H), 7.63 (s, 1H), 7.24-7.12 (d, J=7.2 Hz, 1H), 4.78-4.63 (m, 1H), 4.37 (td, J=10.9, 5.2 Hz, 1H), 4.19 (ddt, J=11.2, 7.7, 3.7 Hz, 1H), 4.11-3.91 (m, 1H), 3.11 (ddt, J=27.6, 19.2, 9.7 Hz, 2H), 2.35-2.05 (m, 2H), 1.97-1.77 (m, 2H), 1.77-1.55 (m, 4H), 1.46 (ttd, J=13.7, 9.0, 8.6, 4.6 Hz, 5H), 1.32-1.07 (m, 8H), 1.07-0.79 (m, 10H). HRMS (TOF MS ES+) Calc M+H=$C_{24}H_{42}N_3O_5$=452.3124, Found Mass=452.3146, 4.8 ppm.

3-cyclohexylpropyl ((S)-4-methyl-1-oxo-1-(((S)-1-oxo-3-((S)-2-oxopyrrolidin-3-yl)propan-2-yl)amino)pentan-2-yl)carbamate (6f). Yield (61.0%), mp 48-50° C., $^1$H NMR (400 MHz, DMSO-$d_6$) δ 9.40 (s, 1H), 8.43 (d, J=7.6 Hz, 1H), 7.63 (s, 1H), 7.25 (d, J=8.0 Hz, 1H), 4.19 (ddd, J=11.4, 7.5, 4.1 Hz, 1H), 4.03 (ddt, J=10.0, 7.0, 3.3 Hz, 1H), 3.96-3.81 (m, 2H), 3.23-3.02 (m, 2H), 2.36-2.06 (m, 2H), 1.97-1.75 (m, 1H), 1.75-1.56 (m, 7H), 1.56-1.30 (m, 4H), 1.30-1.02 (m, 7H), 0.97-0.74 (m, 8H). HRMS (TOF MS ES+) Calc M+H=$C_{23}H_{40}N_3O_5$=438.2968, Found Mass=438.2983, 3.4 ppm Calc M+Na=$C_{23}H_{39}N_3O_5Na$=460.2787, Found Mass=460.2803, 3.4 ppm.

5-ethyl-1,3-dioxan-5-yl ((S)-4-methyl-1-oxo-1-(((S)-1-oxo-3-((S)-2-oxopyrrolidin-3-yl) propan-2-yl)amino)pentan-2-yl)carbamate (6g). Yield (51.0%), mp 41-43° C., $^1$H NMR (400 MHz, DMSO-$d_6$) δ 9.40 (s, 1H), 8.47 (d, J=7.6 Hz, 1H), 7.64 (s, 1H), 7.34 (d, J=8.1 Hz, 1H), 4.82 (d, J=6.0 Hz, 1H), 4.62 (d, J=6.0 Hz, 1H), 4.19 (ddd, J=11.3, 7.3, 4.0 Hz, 1H), 4.11-3.93 (m, 2H), 3.74 (dd, J=12.0, 4.0 Hz, 2H), 3.47 (dd, J=11.4, 2.1 Hz, 2H), 3.12 (dt, J=16.3, 10.4 Hz, 2H), 2.37-2.08 (m, 2H), 1.97-1.79 (m, 1H), 1.79-1.57 (m, 2H), 1.57-1.32 (m, 2H), 1.26 (q, J=7.5 Hz, 2H), 0.87 (ddd, J=10.3, 9.2, 6.6 Hz, 6H), 0.76 (t, J=7.6 Hz, 3H). HRMS (TOF MS ES+) Calc M+Na=$C_{20}H_{33}N_3O_7Na$=450.2216, Found Mass=450.2233, 3.7 ppm.

4,4-difluorocyclohexyl ((S)-4-methyl-1-oxo-1-(((S)-1-oxo-3-((S)-2-oxopyrrolidin-3-yl) propan-2-yl)amino)pentan-2-yl)carbamate (6h). Yield (50.5%), mp 44-46° C., $^1$H NMR (400 MHz, DMSO-$d_6$) δ 9.40 (s, 1H), 8.45 (d, J=7.6 Hz, 1H), 7.66 (s, 1H), 7.34 (d, J=7.4 Hz, 1H), 4.76-4.63 (m, 1H), 4.20 (ddd, J=11.4, 7.6, 4.1 Hz, 1H), 4.09-3.95 (m, 2H), 3.25-2.99 (m, 2H), 2.41-2.09 (m, 2H), 2.09-1.86 (m, 4H), 1.86-1.74 (m, 2H), 1.75-1.56 (m, 5H), 1.55-1.29 (m, 2H), 0.98-0.79 (m, 6H). HRMS (TOF MS ES+) Calc M+H=$C_{20}H_{32}F_2N_3O_5$=432.2310 Found Mass=432.2298, 2.8 ppm.

4,4-difluorocyclohexyl ((S)-3-cyclohexyl-1-oxo-1-(((S)-1-oxo-3-((S)-2-oxopyrrolidin-3-yl) propan-2-yl)amino)propan-2-yl)carbamate (6i). Yield (51.0%), mp 52-54° C., $^1$H NMR (400 MHz, DMSO-$d_6$) δ 9.40 (s, 1H), 8.45 (d, J=7.6 Hz, 1H), 7.64 (s, 1H), 7.33 (d, J=7.9 Hz, 1H), 4.82-4.56 (m, 1H), 4.18 (ddt, J=11.3, 7.7, 3.8 Hz, 1H), 4.05 (dq, J=12.3, 7.7, 7.1 Hz, 2H), 3.22-3.00 (m, 2H), 2.35-2.09 (m, 2H), 2.09-1.85 (m, 4H), 1.81 (dt, J=8.8, 3.6 Hz, 2H), 1.74-1.53 (m, 8H), 1.53-1.38 (m, 2H), 1.32 (q, J=8.9, 7.9 Hz, 1H), 1.24-1.04 (m, 4H), 0.88 (t, J=13.3 Hz, 2H). HRMS (TOF MS ES+) Calc M+H=$C_{23}H_{36}F_2N_3O_5$=472.2623, Found Mass=472.2640, 3.6 ppm Calc M+Na=$C_{23}H_{35}F_2N_3O_5Na$=494.2442, Found Mass=494.2470, 2.8 mmu.

(4,4-difluorocyclohexyl)methyl ((S)-4-methyl-1-oxo-1-(((S)-1-oxo-3-((S)-2-oxopyrrolidin-3-yl)propan-2-yl) amino)pentan-2-yl)carbamate (6j). Yield (50.5%), mp 47-49° C., $^1$H NMR (400 MHz, DMSO-$d_6$) δ 9.40 (s, 1H), 8.44 (d, J=7.5 Hz, 1H), 7.95 (s, 1H), 7.36-7.28 (m, 1H), 4.19 (ddd, J=11.4, 7.6, 4.2 Hz, 1H), 4.03 (td, J=8.8, 6.2 Hz, 1H), 3.84 (d, J=6.1 Hz, 2H), 3.24-3.02 (m, 2H), 2.37-2.08 (m, 2H), 2.08-1.94 (m, 2H), 1.94-1.80 (m, 1H), 1.80-1.55 (m, 7H), 1.55-1.33 (m, 2H), 1.33-1.11 (m, 3H), 0.97-0.79 (m, 6H). HRMS (TOF MS ES+) Calc M+H=$C_{21}H_{34}F_2N_3O_5$=446.2467 Found Mass=446.2452, 3.4 ppm Calc M+Na=$C_{21}H_{33}F_2N_3O_5Na$=468.2286, Found Mass=468.2281, 1.1 ppm (3,3-difluorocyclobutyl)methyl ((2S)-4-methyl-1-oxo-1-(((2S)-1-oxo-3-(2-oxopyrrolidin-3-yl)propan-2-yl)amino) pentan-2-yl)carbamate (6k). Yield (50.5%), mp 40-42° C., $^1$H NMR (400 MHz, DMSO-$d_6$) δ 9.39 (s, 1H), 8.45 (d, J=7.6 Hz, 1H), 7.63 (s, 1H), 7.39 (t, J=7.9 Hz, 1H), 4.31 (td, J=6.7, 4.2 Hz, 1H), 4.19 (ddd, J=11.4, 7.7, 4.1 Hz, 1H), 4.03 (ddt, J=9.8, 7.1, 3.7 Hz, 4H), 3.26-3.00 (m, 2H), 2.60 (tq, J=11.2, 8.8, 5.1, 2.8 Hz, 2H), 2.47-2.24 (m, 3H), 2.24-2.06 (m, 1H), 1.98-1.79 (m, 1H), 1.72-1.55 (m, 2H), 1.55-1.28 (m, 2H), 0.87 (ddd, J=11.1, 7.8, 6.6 Hz, 6H). HRMS (TOF MS ES+) Calc M+H=$C_{19}H_{30}F_2N_3O_5$=418.2154, Found Mass=418.2161, 1.8 ppm Calc M+Na=$C_{19}H_{29}F_2N_3O_5Na$=440.1973, Found Mass=440.1991, 4.1 ppm.

Synthesis of dipeptidyl bisulfite adducts 7. General procedure. To a solution of aldehyde 6 (5 mmol) in dry ethyl acetate (20 mL) was added absolute ethanol (12 mL) with stirring, followed by a solution of sodium bisulfite (540 mg; 5 mmol) in water (5 mL). The reaction mixture was stirred for 3 h at 50° C. The reaction mixture was then allowed to cool to room temperature and filtered through a plug of anhydrous sodium sulfate. The remaining solid in the filter was thoroughly washed with absolute ethanol, and the filtrate was dried over anhydrous sodium sulfate, filtered, and concentrated to yield an off-white solid which was washed with anhydrous diethyl ether (3×50 mL), vacuum filtered and dried in vacuo to obtain compound 7 as white-powder.

sodium (2S)-2-((S)-2-(((cyclohexyloxy)carbonyl)amino)-4-methylpentanamido)-1-hydroxy-3-((S)-2-oxopyrrolidin-3-yl)propane-1-sulfonate (7a). Yield (77.0%), mp 95-97° C., $^1$H NMR (400 MHz, DMSO-$d_6$) δ 7.70-7.32 (m, 2H), 7.30-6.93 (m, 1H), 4.66 (t, J=5.6 Hz, 1H), 4.56-4.30 (m, 1H), 4.07-3.89 (m, 1H), 3.89-3.65 (m, 1H), 3.08 (dt, J=33.4, 7.9 Hz, 2H), 2.40-2.05 (m, 2H), 1.95 (dt, J=31.2, 13.5 Hz, 1H), 1.84-1.71 (m, 3H), 1.71-1.60 (m, 3H), 1.60-1.52 (m, 1H), 1.52-1.32 (m, 2H), 1.32-1.13 (m, 6H), 0.84 (dt, J=9.7, 6.5 Hz, 6H).

sodium (2S)-2-((S)-2-((((4-ethylcyclohexyl)oxy)carbonyl)amino)-4-methylpentanamido)-1-hydroxy-3-((S)-2-oxopyrrolidin-3-yl)propane-1-sulfonate (7b). Yield (81.0%), mp 115-117° C., $^1$H NMR (400 MHz, DMSO-$d_6$) δ 7.69-7.34 (m, 2H), 7.27-6.99 (m, 1H), 4.79-4.58 (m, 1H), 4.37 (tt, J=11.0, 4.2 Hz, 1H), 4.23 (tq, J=9.4, 2.7 Hz, 1H), 4.12-3.70 (m, 2H), 3.20-2.97 (m, 2H), 2.38-2.06 (m, 2H), 2.06-1.82 (m, 2H), 1.73 (d, J=12.8 Hz, 2H), 1.65-1.50 (m, 2H), 1.50-1.31 (m, 4H), 1.31-1.12 (m, 6H), 1.12-1.02 (m, 2H), 1.02-0.90 (m, 1H), 0.85 (td, J=6.9, 4.0 Hz, 6H).

sodium (2S)-1-hydroxy-2-((S)-4-methyl-2-((((4-propylcyclohexyl)oxy)carbonyl)amino) pentanamido)-3-((S)-2-oxopyrrolidin-3-yl)propane-1-sulfonate (7c). Yield (77.5%), mp 124-126° C., $^1$H NMR (400 MHz, DMSO-$d_6$) δ 7.62-7.35 (m, 2H), 7.26-7.00 (m, 1H), 4.80-4.59 (m, 1H), 4.35 (dd, J=9.2, 4.1 Hz, 1H), 4.29-4.12 (m, 1H), 4.12-3.77 (m, 2H), 3.07 (dq, J=33.0, 8.7, 8.3 Hz, 2H), 2.28-2.03 (m, 2H), 2.04-1.80 (m, 2H), 1.71 (d, J=13.1 Hz, 2H), 1.65-1.50 (m, 2H), 1.51-1.35 (m, 4H), 1.28 (h, J=8.2, 7.8 Hz, 6H), 1.23-1.03 (m, 5H), 1.03-0.76 (m, 6H).

sodium (2S)-1-hydroxy-2-((S)-2-((((4-isopropylcyclohexyl)oxy)carbonyl)amino)-4-methyl pentanamido)-3-((S)-2-oxopyrrolidin-3-yl)propane-1-sulfonate (7d). Yield (78.0%), mp 101-103° C., $^1$H NMR (400 MHz, DMSO-$d_6$) δ 7.67-7.26 (m, 2H), 7.16 (dt, J=18.3, 9.0 Hz, 1H), 4.83-4.62 (m, 1H), 4.36 (dq, J=11.2, 6.4, 5.3 Hz, 1H), 4.23 (td, J=9.2, 4.7 Hz, 1H), 4.07-3.70 (m, 2H), 3.21-2.96 (m, 2H), 2.43-2.04 (m, 2H), 2.04-1.84 (m, 2H), 1.84-1.63 (m, 2H), 1.63-1.47 (m, 2H), 1.47-1.34 (m, 4H), 1.34-1.14 (m, 2H), 1.14-0.92 (m, 3H), 0.85 (dd, J=10.5, 6.7 Hz, 12H).

sodium (2S)-2-((S)-2-((((4-butylcyclohexyl)oxy)carbonyl)amino)-4-methylpentanamido)-1-hydroxy-3-((S)-2-oxopyrrolidin-3-yl)propane-1-sulfonate (7e). Yield (50.5%), mp 128-130° C., $^1$H NMR (400 MHz, DMSO-$d_6$) δ 7.65-7.33 (m, 2H), 7.14 (td, J=19.7, 17.5, 8.3 Hz, 1H), 4.80-4.63 (m, 1H), 4.37 (tt, J=8.6, 4.0 Hz, 1H), 4.28-4.16 (m, 1H), 4.11-3.78 (m, 1H), 3.09 (dt, J=34.3, 8.9 Hz, 2H), 2.24-2.05 (m, 2H), 2.05-1.82 (m, 2H), 1.72 (d, J=12.7 Hz, 3H), 1.66-1.51 (m, 3H), 1.51-1.34 (m, 4H), 1.32-1.03 (m, 8H), 1.01-0.75 (m, 10H).

sodium (2S)-2-((S)-2-(((3-cyclohexylpropoxy)carbonyl)amino)-4-methylpentanamido)-1-hydroxy-3-((S)-2-oxopyrrolidin-3-yl)propane-1-sulfonate (7f). Yield (76.0%), mp 104-106° C., $^1$H NMR (400 MHz, DMSO-$d_6$) δ 7.73-7.34 (m, 2H), 7.32-7.08 (m, 1H), 4.23 (t, J=10.6 Hz, 1H), 4.13-3.68 (m, 3H), 3.10 (dt, J=28.3, 9.6 Hz, 2H), 2.27-2.05 (m, 2H), 1.96 (dt, J=26.0, 12.3 Hz, 1H), 1.83-1.49 (m, 10H) 1.49-1.30 (m, 2H), 1.30-1.02 (m, 7H), 0.97-0.75 (m, 8H).

sodium (2S)-2-((S)-2-((((5-ethyl-1,3-dioxan-5-yl)oxy)carbonyl)amino)-4-methylpentan-amido)-1-hydroxy-3-((S)-2-oxopyrrolidin-3-yl)propane-1-sulfonate (7g). Yield (72.0%), mp 92-94° C., $^1$H NMR (400 MHz, DMSO-$d_6$) δ 7.60 (dd, J=34.3, 9.2 Hz, 1H), 7.45 (d, J=3.6 Hz, 1H), 7.28 (dd, J=27.2, 8.4 Hz, 1H), 4.81 (d, J=6.0 Hz, 1H), 4.63 (d, J=6.0 Hz, 1H), 4.22 (t, J=10.5 Hz, 1H), 4.10-3.88 (m, 2H), 3.79-3.64 (m, 2H), 3.47 (dd, J=11.5, 5.1 Hz, 2H), 3.18-2.98 (m, 2H), 2.25-2.04 (m, 2H), 1.95 (dt, J=22.7, 11.9 Hz, 1H), 1.69-1.50 (m, 2H), 1.45 (p, J=7.3, 6.2 Hz, 2H), 1.34-1.16 (m, 2H), 1.16-0.99 (m, 1H), 0.85 (ddd, J=10.9, 6.5, 2.9 Hz, 6H), 0.76 (t, J=7.6 Hz, 3H).

sodium (2S)-2-((S)-2-((((4,4-difluorocyclohexyl)oxy)carbonyl)amino)-4-methylpentan-amido)-1-hydroxy-3-((S)-2-oxopyrrolidin-3-yl)propane-1-sulfonate (7h). Yield (69.0%), mp 74-76° C., $^1$H NMR (400 MHz, DMSO-$d_6$) δ 7.75-7.38 (m, 2H), 7.30 (dt, J=35.6, 7.5 Hz, 1H), 4.80-4.60 (m, 1H), 4.56-4.27 (m, 1H), 4.07-3.88 (m, 1H), 3.73 (q, J=7.1 Hz, 1H), 3.63 (dt, J=9.6, 6.7 Hz, 1H), 3.10 (dq, J=25.2, 9.8, 8.5 Hz, 2H), 2.37-2.08 (m, 2H), 2.08-1.86 (m, 4H), 1.80 (d, J=10.7 Hz, 2H), 1.74-1.55 (m, 4H), 1.55-1.32 (m, 3H), 0.99-0.75 (m, 6H).

sodium (2S)-2-((S)-3-cyclohexyl-2-((((4,4-difluorocyclohexyl)oxy)carbonyl)amino)propan-amido)-1-hydroxy-3-((S)-2-oxopyrrolidin-3-yl)propane-1-sulfonate (7i). Yield (50.5%), mp 99-101° C., $^1$H NMR (400 MHz, DMSO-$d_6$) δ 7.67-7.51 (m, 1H), 7.46 (d, J=3.1 Hz, 1H), 7.43-7.22 (m, 1H), 4.77-4.63 (m, 1H), 4.29-4.15 (m, 1H), 4.12-3.80 (m, 2H), 3.21-2.98 (m, 2H), 2.27-1.85 (m, 6H), 1.85-1.34 (m, 12H), 1.34-1.22 (m, 1H), 1.22-1.03 (m, 4H), 0.96-0.72 (m, 3H).

sodium (2S)-2-((S)-2-((((4,4-difluorocyclohexyl)methoxy)carbonyl)amino)-4-methylpentan-amido)-1-hydroxy-3-((S)-2-oxopyrrolidin-3-yl)propane-1-sulfonate (7j). Yield (50.5%), mp 90-92° C., $^1$H NMR (400 MHz, DMSO-$d_6$) δ 7.57 (t, J=8.9 Hz, 1H), 7.45 (s, 1H), 7.38-7.17 (m, 1H), 4.29-4.10 (m, 1H), 4.05-3.67 (m, 4H), 3.09 (dt, J=29.8, 8.8 Hz, 2H), 2.33-2.05 (m, 2H), 2.05-1.88 (m, 4H), 1.88-1.64 (m, 5H), 1.64-1.48 (m, 2H), 1.43 (q, J=7.3 Hz, 2H), 1.30-1.11 (m, 2H), 1.04-0.78 (m, 6H).

sodium (2S)-2-((S')-2-((((3,E3-difluorocyclobutyl)methoxy)carbonyl)amino)-4-methylpentan-amido)-1-hydroxy-3-(2-oxopyrrolidin-3-yl)propane-1-sulfonate (7k). Yield (50.50%), mp 77-79° C., $^1$H NMR (400 MHz, DMSO-$d_6$) δ 7.74-7.12 (m, 3H), 4.20 (d, J=9.9 Hz, 1H), 4.12-3.90 ((, 4H), 3.90-3.78 (i, 1H), 3.22-2.93 (m, 2H), 2.68-2.53 (i, 2H), 2.47-2.24 (N, 4H), 2.24-2.05 (>, 1H), 2.05-1.70 (m, 1H), 1.70-1.52 (m, 2H), 1.52-1.29 (m, 2H), 0.86 (ddd, J=14.4, 11.0, 6.6 Hz, 6H).

TABLE 1

Structures of the 3CLpro inhibitors and their effects on various coronaviruses in the FRET assay ($IC_{50}$) and cell culture system ($EC_{50}$), as well as cell culture toxicity ($CC_{50}$).

(I)

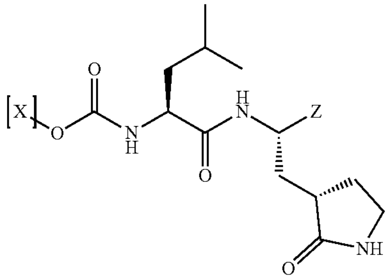

| Compound Scheme 1 | [X] | Z | $IC_{50}$ in enzyme assay (μM) MERS-CoV | SARS-CoV | SARS-CoV-2 | $EC_{50}$ in cell culture (μM) MERS-CoV | SARS-CoV-2 | MHV | FIPV | $CC_{50}$ (μM) |
|---|---|---|---|---|---|---|---|---|---|---|
| 6a | 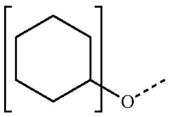 | CHO | 0.35 | 3.9 | 3.7 | ND* | ND | 0.12 | 0.09 | >100 |
| 7a | | $CH(OH)SO_3Na$ | 0.15 | 3.8 | 3.5 | 0.08 | ND | 0.08 | 0.07 | >100 |
| 6c | 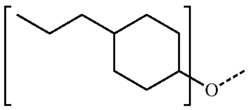 | | 0.15 | 1.7 | 1.6 | 0.05 | 0.10 | 0.13 | 0.12 | >100 |
| 7c | | $CH(OH)SO_3Na$ | 0.10 | 1.7 | 1.6 | ND | ND | 0.16 | 0.17 | >100 |
| 6e | 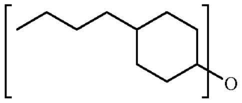 | CHO | 0.15 | 0.9 | 0.8 | ND | 0.10 | 0.12 | 0.22 | >100 |
| 7e | | $CH(OH)SO_3Na$ | 0.13 | 1.0 | 1.1 | 0.53 | ND | 0.13 | 0.17 | >100 |
| 6h | 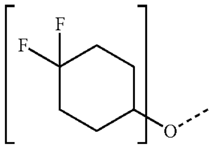 | CHO | 0.07 | 2.3 | 1.5 | ND | 0.11 | 0.08 | 0.22 | >100 |
| 7h | | $CH(OH)SO_3Na$ | 0.08 | 2.2 | 1.6 | 0.21 | ND | 0.11 | 0.12 | >100 |
| 6j | 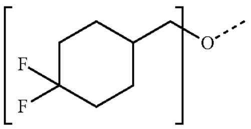 | CHO | 0.08 | 1.2 | 0.9 | 0.03 | 0.19 | 0.20 | 0.08 | >100 |
| 7j | | $CH(OH)SO_3Na$ | 0.1 | 1.1 | 1.1 | ND | ND | 0.16 | 0.07 | >100 |
| GC376# | | | 1.6 | 2.2 | 2.4 | 0.9 | ND | 1.1* | 0.04* | >100 |

#Not determined. Because bisulfite adducts convert to aldehyde form only one between bisulfite adduct and aldehyde was determined.

TABLE 2

Additional compounds of the 3CLpro inhibitors and their effects on MERS-CoV in the FRET assay ($IC_{50}$) as well as cell culture toxicity ($CC_{50}$).

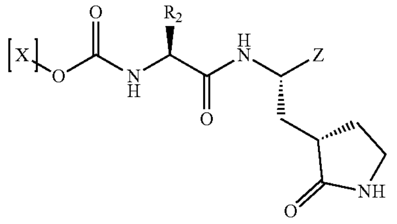

(I)

| Compound | [X] | $R_2$ | Z | MERS-CoV $IC_{50}$(μM) | $CC_{50}$(μM) |
|---|---|---|---|---|---|
| 6b | 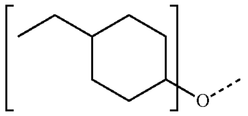 | Leu | CHO | 0.33 | >100 |
| 7b | | | $CH(OH)SO_3Na$ | 0.32 | >100 |
| 6d | 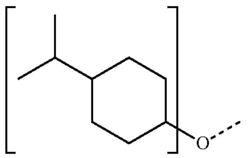 | | CHO | 0.41 | >100 |
| 7d | | | $CH(OH)SO_3Na$ | 0.43 | >100 |
| 6f | 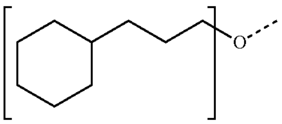 | | CHO | 0.75 | >100 |
| 7f | | | $CH(OH)SO_3Na$ | 0.64 | >100 |
| 6g | 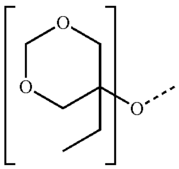 | | CHO | 0.12 | >100 |
| 7g | | | $CH(OH)SO_3Na$ | 0.16 | >100 |
| 6i | 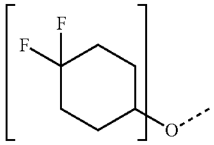 | Cha | CHO | >50 | >100 |
| 7i | | | $CH(OH)SO_3Na$ | >50 | >100 |
| 6k | 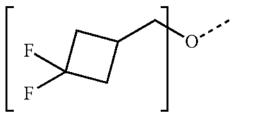 | Leu | CHO | 0.50 | >100 |
| 7k | | | $CH(OH)SO_3Na$ | 0.40 | >100 |

Fluorescence resonance energy transfer (FRET) enzyme assays. The expression and purification of the 3CLpro of MERS-CoV, SARS-CoV or FIPV was performed by a standard method described previously by our lab. We also cloned and expressed 3CLpro of SARS-CoV-2. The codon-optimized cDNA of full length of 3CLpro of SARS-CoV-2 (GeneBank number MN908947.3, incorporated by reference herein) fused with sequences encoding 6 histidine at N-terminal was synthesized by Integrated DNA (Coralville, IA). The synthesized gene was subcloned into the pET-28a(+) vector. The expression and purification of SARS-CoV-2 3CLpro were conducted following the standard procedure described by our lab. Briefly, stock solutions of compounds 6a-k and 7a-k were prepared in DMSO and diluted in assay buffer which was comprised of 20 mM HEPES buffer, pH 8, containing NaCl (200 mM), EDTA (0.4 mM), glycerol (60%), and 6 mM dithiothreitol (DTT). The protease (3CLpro of MERS-CoV, SARS-CoV, SARS-CoV-2 or FIPV) was mixed with serial dilutions of each compound or with DMSO in 25 μL of assay buffer and incubated at 37° C. for 30 min (MERS-CoV and FIPV) or at room temperature for 1 h (SARS-CoV and SARS-CoV-2), followed by the addition of 25 μL of assay buffer containing substrate (FAM-SAVLQ/SG-QXL® 520, AnaSpec, Fremont, CA). The substrate was derived from the cleavage sites on the viral polyproteins of SARS-CoV). Fluorescence readings were obtained using an excitation wavelength of 360 nm and an emission wavelength of 460 nm on a fluorescence microplate reader (FLx800; Biotec, Winoosk, VT) 1 h following the addition of substrate. Relative fluorescence units (RFU) were determined by subtracting background values (substrate-containing well without protease) from the raw fluorescence values. The dose-dependent FRET inhibition curves were fitted with a variable slope by using GraphPad Prism software (GraphPad, La Jolla, CA) in order to determine the $IC_{50}$ values of the compounds.

Antiviral assays in cell-based system. Compounds 6a-k and 7a-k were also investigated for their antiviral activity against the replication of MERS-CoV, FIPV or MHV-1 in Huh-7, CRFK or CCL1 cells, respectively. Briefly, medium containing DMSO (<0.1%) or each compound (up to 100 μM) was added to confluent cells, which were immediately infected with viruses at an MOI of 0.01. After incubation of the cells at 37° C. for 24 h, viral titers were determined with the $TCID_{50}$ method (FIPV or MHV) with the CRFK or CLL1 cells or plaque assay with Vero81 cells (MERS-CoV). For SARS-CoV-2, confluent VeroE6 cells were inoculated with ~50-100 plaque forming units/well, and medium containing various concentrations of each compound and agar was applied to the cells. After 48-72 h, plaques in each well were counted. $EC_{50}$ values were determined by GraphPad Prism software using a variable slope (GraphPad, La Jolla, CA).

Nonspecific cytotoxic effects. The cytotoxic dose for 50% cell death ($CC_{50}$) for compounds 6a-k and 7a-k was determined in Huh-7, CRFK or CCL1 cells. Confluent cells grown in 96-well plates were incubated with various concentrations (1 to 100 μM) of each compound for 72 h. Cell cytotoxicity was measured by a CytoTox 96 nonradioactive cytotoxicity assay kit (Promega, Madison, WI), and the $CC_{50}$ values were calculated using a variable slope by GraphPad Prism software. The in vitro therapeutic index was calculated by dividing the $CC_{50}$ by the $EC_{50}$.

X-ray crystallographic studies. Crystallization and data collection. Purified MERS-CoV 3CLpro or SARS-CoV 3CLpro in 100 mM NaCl, 20 mM Tris pH 8.0 were concentrated to 10.6 mg/mL (0.3 mM) and 22 mg/mL (0.64 mM) respectively for crystallization screening. All crystallization experiments were setup using an NT8 drop-setting robot (Formulatrix Inc.) and UVXPO MRC (Molecular Dimensions) sitting drop vapor diffusion plates at 18° C. 100 nL of protein and 100 nL crystallization solution were dispensed and equilibrated against 50 μL of the latter. Stock solutions (100 mM) of compounds 6b, 6d, 6g, 6h, 7i, and 7j were prepared in DMSO and complexes were generated by mixing 1 μL of the ligand (2 mM) with 49 μL (0.29 mM) of the protease and incubating on ice for 1 h. Crystals of the MERS 3CLpro inhibitor complexes were obtained from the following conditions. Compounds 6b, 6d, 6g and 6h: Proplex screen (Molecular Dimensions) condition E2 (8% (w/v) PEG 8000, 100 mM sodium citrate pH 5.0), compound 7i: Proplex screen (Molecular Dimensions) condition B8 (15% (w/v) PEG 4000, 100 mM sodium citrate pH 5.0, 100 mM magnesium chloride) and compound 7j: Index HT screen (Hampton Research) condition F6 (25% (w/v) PEG 3350, 100 mM Bis-Tris pH 5.5, 200 mM ammonium sulfate). Crystals of the SARS-CoV 3CLpro complex with compound 7j were obtained from the Index HT screen (Hampton Research) condition H8 (15% (w/v) PEG 3350, 100 mM magnesium formate). Samples were transferred to a fresh drop containing 80% crystallant and 20% (v/v) PEG 200 before storing in liquid nitrogen. X-ray diffraction data were collected at the Advanced Photon Source beamline 17-ID using a Dectris Pilatus 6M pixel array detector.

Structure solution and refinement. Intensities were integrated using XDS using Autoproc and the Laue class analysis and data scaling were performed with Aimless. Structure solution was conducted by molecular replacement with Phaser using a previously determined structure of MERS 3CLpro (PDB: 5WKK[21]) and SARS-CoV 3CLpro (PDB: 1Q2W) as the search models. Structure refinement and manual model building were conducted with Phenix and Coot, respectively. Disordered side chains were truncated to the point for which electron density could be observed. Structure validation was conducted with MolProbity and figures were prepared using the CCP4MG package. Crystallographic data are provided in Table 3.

TABLE 3

Crystallographic data for MERS CoV 3CLPro and SARS CoV 3CLPro inhibitor complexes.

| Protease:inhibitor/ PDB Code | MERS:6b 6VGY | MERS:6d 6VGZ | MERS:6g 6VH0 | MERS:6b 6VH1 | MERS:7i 6VH2 | MERS:7j 6VH3 | SARS:7j 6W2A |
|---|---|---|---|---|---|---|---|
| Data Collection | | | | | | | |
| Unit-cell parameters (Å, °) | a = 76.14<br>b = 91.67<br>c = 100.70 | a = 76.19<br>b = 91.72<br>c = 101.56 | a = 75.91<br>b = 91.75<br>c = 100.35 | a = 76.06<br>b = 91.24<br>c = 100.35 | a = 76.03<br>b = 91.10<br>c = 100.78 | a = 75.63<br>b = 90.96<br>c = 100.03 | a = 55.00<br>b = 100.00<br>c = 59.27<br>β = 108.3 |
| Space group | $P2_12_12_1$ | $P2_12_12_1$ | $P2_12_12_1$ | $P2_12_12_1$ | $P2_12_12_1$ | $P2_12_12_1$ | $P2_1$ |
| Resolution (Å)[1] | 45.83-2.05 (2.11-2.05) | 44.44-2.25 (2.32-2.25) | 44.02-1.95 (2.00-1.95) | 43.97-2.30 (2.38-2.30) | 45.55-2.26 (2.33-2.26) | 45.48-2.20 (2.27-2.20) | 50.00-1.65 (1.68-1.65) |
| Wavelength (Å) | 1.0000 | 1.0000 | 1.0000 | 1.0000 | 1.0000 | 1.0000 | 1.0000 |
| Temperature (K) | 100 | 100 | 100 | 100 | 100 | 100 | 100 |
| Observed reflections | 293,623 | 228,970 | 345,604 | 210,802 | 223,848 | 238,120 | 490,396 |
| Unique reflections | 44,480 | 34,478 | 51,804 | 31,745 | 33,514 | 35,788 | 72,975 |
| <I/σ(I)>[1] | 12.2 (1.8) | 9.8 (1.9) | 10.3 (2.1) | 17.8 (2.2) | 10.3 (2.1) | 9.3 (1.9) | 12.6 (1.6) |
| Completeness (%)[1] | 98.9 (99.9) | 99.9 (99.8) | 100 (100) | 100 (100) | 99.6 (98.8) | 100 (100) | 99.9 (99.8) |
| Multiplicity[1] | 6.6 (6.7) | 6.6 (6.5) | 6.7 (6.9) | 6.6 (6.9) | 6.7 (6.5) | 6.7 (6.6) | 6.7 (6.8) |
| $R_{merge}$ (%)[1,2] | 8.2 (110.4) | 12.7 (109.7) | 9.8 (94.3) | 6.2 (91.9) | 12.8 (91.8) | 14.1 (104.0) | 6.9 (126.0) |
| $R_{meas}$ (%)[1,4] | 8.9 (119.7) | 13.8 (119.3) | 10.7 (101.9) | 6.7 (99.4) | 13.9 (99.9) | 15.3 (112.9) | 7.4 (136.4) |
| $R_{pim}$ (%)[1,4] | 3.5 (45.9) | 5.3 (46.4) | 4.1 (38.4) | 2.6 (37.7) | 5.3 (38.7) | 5.9 (43.5) | 2.9 (51.8) |
| $CC_{1/2}$[1,5] | 0.998 (0.737) | 0.996 (0.725) | 0.996 (0.833) | 0.999 (0.829) | 0.997 (0.752) | 0.996 (0.740) | 0.999 (0.703) |

TABLE 3-continued

Crystallographic data for MERS CoV 3CLPro and SARS CoV 3CLPro inhibitor complexes.

| Protease:inhibitor/ PDB Code | MERS:6b 6VGY | MERS:6d 6VGZ | MERS:6g 6VH0 | MERS:6b 6VH1 | MERS:7i 6VH2 | MERS:7j 6VH3 | SARS:7j 6W2A |
|---|---|---|---|---|---|---|---|
| Refinement | | | | | | | |
| Resolution (Å)[1] | 38.18-2.05 | 42.26-2.25 | 39.26-1.95 | 39.12-2.30 | 39.07-2.26 | 43.83-2.20 | 33.93-1.65 |
| Reflections (working/test)[1] | 42,297/ 2,092 | 32,780/ 1,634 | 49,183/ 2,534 | 30,044/ 1,600 | 31,851/ 1,601 | 34,021/ 1,696 | 69,480/ 3,442 |
| $R_{factor}/R_{free}$ (%)[1,3] | 19.2/23.9 | 18.7/24.8 | 19.3/23.9 | 19.2/25.3 | 18.1/24.6 | 18.3/24.5 | 17.2/20.3 |
| No. of atoms (Protein/Ligand/Water) | 4,467/60/ 195 | 4,457/59/ 171 | 4,446/60/ 282 | 4,461/60/ 80 | 4,461/66/ 198 | 4,459/62/ 175 | 4,558/124/ 270 |
| Model Quality | | | | | | | |
| R.m.s deviations | | | | | | | |
| Bond lengths (Å) | 0.009 | 0.009 | 0.011 | 0.013 | 0.009 | 0.012 | 0.010 |
| Bond angles (°) | 0.946 | 0.935 | 1.059 | 1.147 | 0.030 | 1.107 | 1.038 |
| Mean B-factor ($Å^2$) | | | | | | | |
| All Atoms | 46.5 | 42.7 | 40.3 | 61.8 | 39.0 | 37.9 | 32.6 |
| Protein | 46.4 | 42.7 | 40.0 | 61.9 | 38.9 | 37.8 | 32.2 |
| Ligand | 46.0 | 40.4 | 44.9 | 62.8 | 41.6 | 45.8 | 34.8 |
| Water | 47.3 | 43.0 | 43.7 | 51.3 | 40.0 | 38.2 | 39.0 |
| Coordinate error (maximum likelihood) (Å) | 0.25 | 0.29 | 0.23 | 0.33 | 0.31 | 0.26 | 0.17 |
| Ramachandran Plot | | | | | | | |
| Most favored (%) | 98.0 | 97.8 | 98.8 | 95.6 | 98.5 | 98.1 | 98.2 |
| Additionally allowed (%) | 1.9 | 2.2 | 1.0 | 4.1 | 1.4 | 1.5 | 1.8 |

[1]Values in parenthesis are for the highest resolution shell.

[2]$R_{merge} = \Sigma_{hkl}\Sigma_i |I_i(hkl) - \langle I(hkl)\rangle| / \Sigma_{hkl}\Sigma_i I_i(hkl)$, where $I_i(hkl)$ is the intensity measured for the ith reflection and $\langle I(hkl)\rangle$ is the average intensity of all reflections with indices hkl.

[3]$R_{factor} = \Sigma_{hkl} ||F_{obs}(hkl)| - |F_{calc}(hkl)|| / \Sigma_{hkl}|F_{obs}(hkl)|$; Rfree is calculated in an identical manner using 5% of randomly selected reflections that were not included in the refinement.

[4]$R_{meas}$ = redundancy-independent (multiplicity-weighted) $R_{merge}$. $R_{pim}$ = precision-indicating (multiplicity-weighted) $R_{merge}$.

[5]$CC_{1/2}$ is the correlation coefficient of the mean intensities between two random half-sets of data.

Animal care and ethics statement. In vivo studies were performed in animal biosafety level 3 facilities at University of Iowa. All experiments were conducted under protocols approved by the Institutional Animal Care and Use Committee at University of Iowa according to guidelines set by the Association for the Assessment and Accreditation of Laboratory Animal Care and the U.S. Department of Agriculture.

Therapeutic treatment in the mouse model of MERS-CoV infection. Two compounds (6j and 6h) in the series were examined for their in vivo efficacy using 10-week old male hDPP4-KI mice infected with $MERS_{MA}$. In the first study, animals were divided into three groups (N=5-6) and were lightly anesthetized with ketamine/xylazine and infected with 50 μl of 750 plaque forming unit (pfu) MERS-CoV, via intranasal inoculation. Compounds 6j or 6h were formulated in 10% ethanol and 90% PEG400 and given to mice from 1 to 10 dpi at 50 mg/kg/day (once per day) via intraperitoneal administration. The control mice received vehicle. Animals were weighed daily and monitored for 15 days. Animals were euthanized when an animal lost 30% of initial weight or at 15 dpi.

In the next study, we delayed treatment of compound 6j up to 3 dpi to determine the impact of delayed treatment on mice survival. animals were divided into five groups (N=5) and compound 6j (50 mg/kg/day, once per day) was administered to mice starting at one, two or three days after virus challenge (1, 2 or 3 dpi, respectively) until 10 dpi. Mice were monitored for weight loss and survival as described above for 15 days post virus challenge. As controls, vehicle (10% Ethanol+90% PEG400) was administered equivalently to the experimental compound or animals received no treatment (untreated).

The third study was conducted to assess the effects of therapeutic treatment of compound 6j in the lungs. For lung harvest and virus titration, animals were divided into three groups (N=4-5) mice and compound 6j (50 mg/kg/day, once per day) or vehicle was administered to mice at 1 dpi until 10 dpi. Animals were euthanized 3 or 5 dpi, and lungs were removed aseptically, disassociated with a manual homogenizer in 1×PBS, briefly centrifuged, and supernatants removed. Samples were titered on Vero-81 cells as reported elsewhere. For histopathology, mice were euthanized at 6 dpi, lungs were fixed with 10% formalin, and hematoxylin and eosin (HE) stained tissues were examined by a veterinary pathologist using the post-examination method of masking. Briefly, tissues were scored in an ordinal manner for edema and hyaline membranes parameters using the following scale: 0—none, 1—rare (<5 alveoli), 2—<33% of lung fields, 3—34-66% lung fields, and 4—>66% lung fields.

Statistical analysis. The analysis of survival curves in groups was performed using a Log-rank (Mantel-Cox) test and Gehan-Breslow-Wilcoxon test by GraphPad Prism Software (San Diego, CA). Log-transformed viral titers in the lungs, edema and hyaline membranes in groups were analyzed using multiple T test by GraphPad Prism Software.

Results

Figure 5:
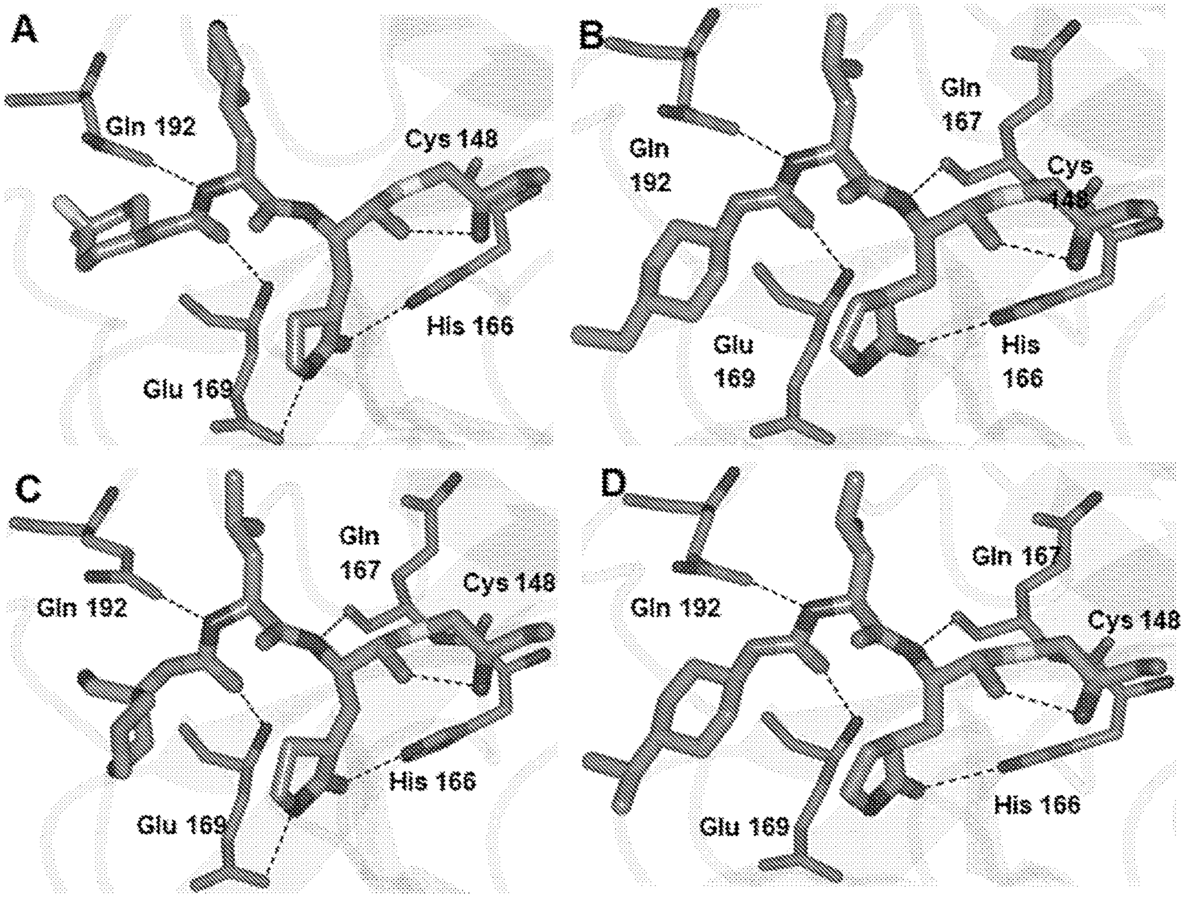
FIG. 5 shows the hydrogen bond interactions (dashed lines) between MERS-CoV 3CLpro and A) 7i, B) 6b, C) 6g, and D) 6d.

Crystallographic studies of 3CLpro. To establish the mechanism of action, as well as to illuminate the structural determinants associated with the binding of inhibitor (I) to the active site of MERS-CoV 3CLpro in general, and the mode of interaction with the $S_4$ subsite in particular, multiple high-resolution cocrystal structures were determined. Inspection of crystal structures of inhibitors bound to MERS-CoV 3CLpro revealed the potential to achieve enhanced binding interactions with the $S_4$ subsite using suitably-decorated cyclohexane derivatives. The vicinity of the $S_4$ pocket of MERS-CoV 3CLpro is encompassed by an array of primarily hydrophobic residues, including Phe188, Val193, Ala171, and Leu170 (FIGS. 2A-F, 2G-L, and FIG. 3). Hydrophobic and hydrogen-bonding functionalities were incorporated into the inhibitors to capture additional interactions, and the position of the cyclohexyl moiety was also examined using appropriate congeners. The bisulfite adducts revert to the corresponding aldehydes which subsequently react with Cys 148 to form nearly identical covalent complexes with a tetrahedral arrangement at the newly formed stereo center (FIGS. 2A-F and FIGS. 3-5). The backbone of compound 6h (Table 1 and FIG. 2A-F) engaged in H-bonding interactions with residues Gln192, Gln167 and Glu169. Three additional side chain H-bonds between the y-lactam ring and His166, Phe143 and Glu169 are also clearly evident (FIG. 2A-F). Furthermore, the side chain of the $P_2$ Leu is snugly ensconced in the hydrophobic $S_2$ pocket (FIG. 2A-F). Interestingly, the extra methylene group in compound 7j (converted to aldehyde, thus identical to 6j) results in re-orientation of the difluorocyclohexyl group and the formation of three H-bonds between Gln195 and Ala171 and the fluorine atoms, with concomitant loss of one of the Gln192 hydrogen bonds and the displacement of Phe143 (FIG. 2A-F). In our enzyme and cell-based assays, substitution of the $P_2$ Leu with $P_2$ Cha (Table 2, compound 7i) resulted in a significant loss of inhibitory activity. Without wishing to be bound by theory, this appears to result from the loss of a H-bond with Gln192 and the loss of two additional H-bonds from the displacement of Gln167 and Phe143 (FIG. 5A). The electron density, hydrogen bond interactions and electrostatic surface representations for MERS 3CLpro in complex with compounds 7i, 6b, 6g and 6d are provided in FIG. 3-5.

In the SARS-CoV 3CLpro-compound 7j complex (FIG. 2G-L), the backbone of compound 7j forms direct H-bonds with Cys 145, His 163, His 164, Glu 166, Gln 189. This compound also forms an additional H-bond with His 41 and a water mediated contact with Gly 143 (FIG. 2G-L). However, there is a loss of three H-bonds with between Gln195 and Ala171 and the fluorine atoms, compared to MERS-CoV 3CLpro. Without wishing to be bound by theory, compound 7j in these tests displayed moderately lower potency against SARS-CoV 3CLpro compared to MERS-CoV 3CLpro in the FRET assay, suggesting that H-bond forming moieties that fit into the $S_4$ subsite play an important role in potency.

Discussion

The 3CLpro compounds have potent activity in the FRET enzyme assay and cell-based assay. The activity of compounds 6a-k and 7a-k against various coronavirus 3CLpro were evaluated in the FRET assay, and select compounds were also tested in the cell-based system. Tables 1-2 show 50% inhibitory concentration ($IC_{50}$) in the enzyme assay and 50% effective concentration ($EC_{50}$) in cell culture for various coronaviruses (average of at least two determinations). The 50% cytotoxic concentration ($CC_{50}$) of compounds are also listed. The results show that inhibitors with a $P_2$ Leu residue, which is strongly preferred by MERS-CoV 3CLpro, display submicromolar $IC_{50}$ values, but replacement of Leu with Cha (cyclohexyl alanine) abolish their activity (6h and 7h versus 6i and 7i) (Tables 1 and 2). The compounds tested against MERS-CoV in cell culture (7a, 6c, 7e, 7g, 7h and 6j) also display submicromolar $EC_{50}$ values, except for 7g. Among these compounds, 6j showed most potent antiviral activity against MERS-CoV with $EC_{50}$ value of 0.03 μM. GC376 that has a $P_2$ Leu residue and a non-fluorinated benzyl cap, exhibited 3-fold lower potency against MERS-CoV in cell culture compared to 6j.

The activity of a select number of compounds (6a, 7a, 6c, 7c, 6e, 7e, 6h, 7h, 6j and 7j) was also determined against SARS-CoV-2, FIPV and mouse hepatitis virus (MHV) in cell culture, and the 3CLpro of SARS-CoV and SARS-CoV-2 in the enzyme assay (Table 1). They are effective against SARS-CoV-2 with $EC_{50}$ values ranging between 100 to 200 nM (Table 1). These compounds are also found to be highly potent against FIPV and MHV, with the $EC_{50}$ values ranging between 70 to 200 nM. In the enzyme assays, these compounds are active against 3CLpro of SARS-CoV and SARS-CoV-2, although the effects were less pronounced (i.e. 6j has a 4.5-fold higher $IC_{50}$ value for SARS-CoV-2 3CLpro than MERS-CoV) (Table 1). Of note, GC376 also showed less activity against SARS-CoV-2 compared to FIPV 3CLpro by 5.6-fold. These findings suggest that the compounds are endowed with broad-spectrum activity against multiple human and animal coronaviruses. The low cytotoxicity of this series of compounds, coupled with the high potency of some of the compounds, provided the impetus for conducting in vivo studies.

Crystallographic studies of 3CLpro. Inspection of previously-obtained crystal structures of inhibitors bound to MERS-CoV 3CLpro revealed the potential to achieve enhanced binding interactions with the $S_4$ subsite using suitably-decorated cyclohexane derivatives. The vicinity of the $S_4$ pocket of MERS-CoV 3CLpro is encompassed by an array of primarily hydrophobic residues, including Phe188, Val193, Ala171, and Leu170 (FIG. 2A-L-FIG. 4). Hydrophobic and hydrogen-bonding functionalities were incorporated into the inhibitors to capture additional interactions, and the position of the cyclohexyl moiety was also examined using appropriate congeners. Cocrystal structures of various compounds including 7j (bisulfite adduct of 6j) with MERS-CoV or SARS-CoV 3CLpro are included in the supplementary materials.

Figure 6:
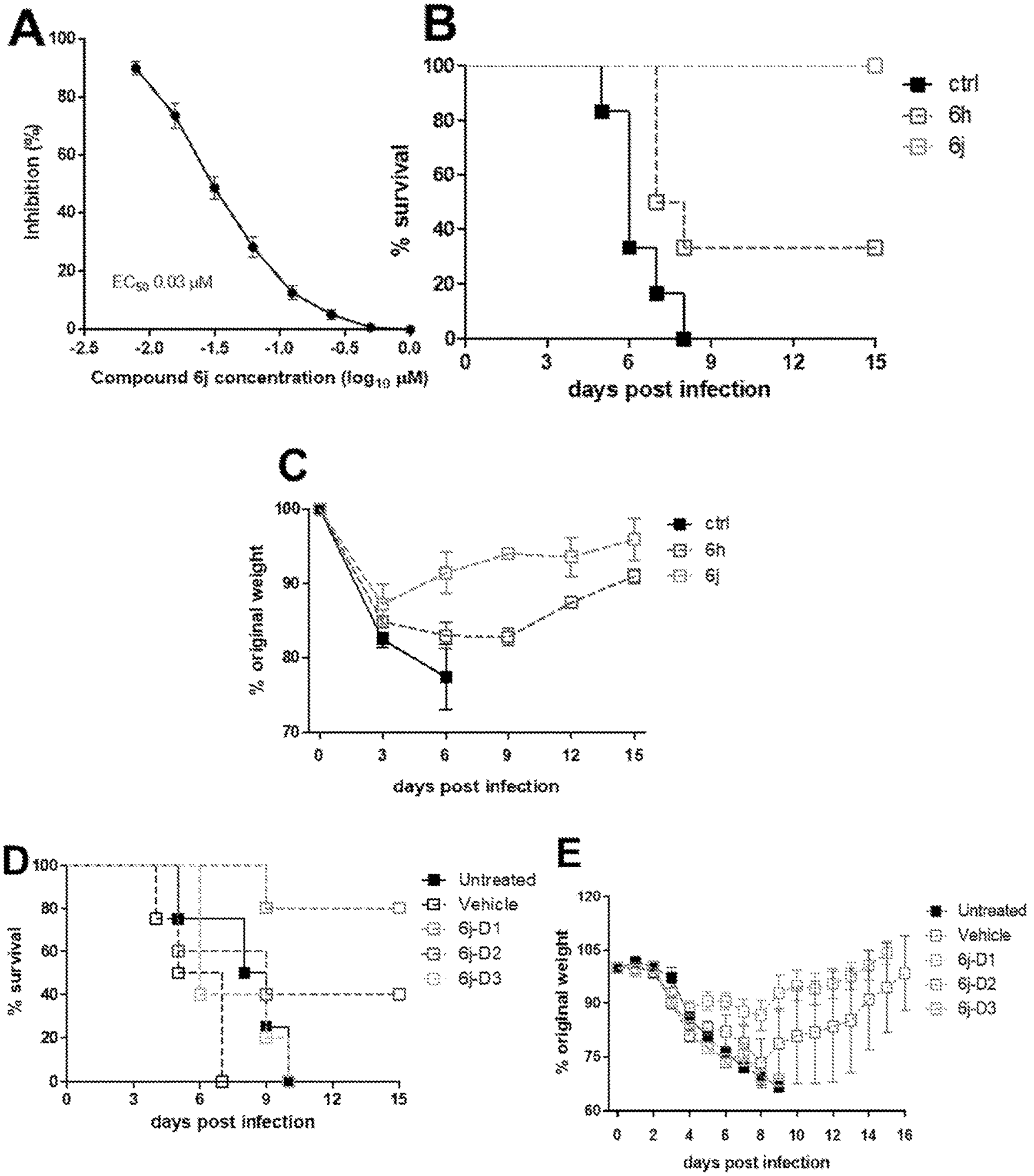
FIG. 6. shows data from therapeutic treatment of compound 6j or 6h in the hDPP4-KI mice infected with $MERS_{MA}$. (A) Shown is a dose-dependent curve for inhibition of MERS-CoV in cell culture by compound 6j. Serial dilutions of compound 6j were added to confluent Huh-7 cells, which were immediately infected with MERS-CoV at a multiplicity of infection (MOI) of 0.01. After incubation of the cells at 37° C. for 48 hours, viral titers were determined using a plaque-forming assay, and 50% inhibitory concentration ($EC_{50}$) values were determined with GraphPad Prism software. (B and C) hDPP4-KI mice infected with mouse-adapted MERS-CoV ($MERS_{MA}$-CoV) (n=6) were treated with compound 6j or 6h starting at 1 day post virus infection (dpi) for up to 10 days, and survival (B) and body weight (C) were monitored for 15 days. Control mice received vehicle only. (D and E) hDPP4-KI mice infected with $MERS_{MA}$-COV were treated with compound 6j (n=5) starting at 1, 2, or 3 dpi, and survival (D) and body weight (E) were monitored for 15 days. Untreated mice and vehicle-treated mice (n=4) were included as controls. Data points represent the mean and the SEM for one experiment. The analysis of survival curves in groups was performed using a log-rank (Mantel-Cox) test and a Gehan-Breslow-Wilcoxon test.

Therapeutic treatment with 3CLpro inhibitors significantly increases survival and reduces lung virus load and pathology in mice. Compound 6j was identified for further study using a cell-based assay with an $EC_{50}$ 0.03 μM against MERS-CoV, and we determined the efficacy of compound 6j and another derivative 6h in the mouse model of MERS-CoV infection. These two compounds (6h and 6j) have strong potency against MERS-CoV in the enzyme or cell-based assay (Table 1 and FIG. 6A). The generation of transgenic mice expressing hDPP4 for MERS-CoV infection was previously reported. The hDPP4 knockin mouse (hDPP4-KI) infected with mouse-adapted virus ($MERS_{MA}$) develop fatal lung disease with severe inflammation, diffuse alveolar damage, and weight loss. In the first study, hDPP4-KI mice were infected with $MERS_{MA}$ and treated with 6h, 6j (50 mg/kg/day, once a day) or vehicle (control) from one day after virus infection (1 dpi) to 10 dpi. All mice treated with vehicle (mock) died by 8 dpi (FIG. 6B). In contrast, 40% of mice treated with 6h survived, and all mice treated with 6j (50 mg/kg/day from 1 to 10 dpi) were alive at the end of the study (15 dpi) (FIG. 6B). The survival of mice treated with 6j or 6h significantly increased compared to the control ($p<0.05$), and the 6j treated mice also had significantly improved survival rate compared to 6h treated mice ($p<0.05$). All mice treated with 6j rapidly recovered from body weight loss from 3 dpi (FIG. 6C). The mice that survived with 6h treatment continued to lose body weight until 6 dpi but started to gain weight from 9 dpi (FIG. 6C).

Interestingly, compounds 6j and 6h share a near identical structure except for the extra methylene group present in compound 6j. Without wishing to be bound by theory, while both compounds 6h and 6j show potent anti-3CLpro activity, the antiviral activity of compound 6h in cell culture was lower in these tests than compound 6j (Table 1), which may explain its lower therapeutic efficacy in the mouse model (FIG. 6B).

After we observed that therapeutic treatment of 6j resulted in survival of infected mice, we conducted another study by delaying treatment initiation by up to 3 dpi. Similar to the first study, no untreated mice or mice given vehicle survived, with no statistical difference between these two groups (0% survival). When 6j treatment was started on 1 dpi, four of the five mice survived (80% survival). There was a statistically significant increased survival in mice treated from 1 dpi compared to untreated or vehicle-treated mice ($P<0.05$). When 6j treatment was delayed by one additional day (2 dpi), survival of mice treated with 6j decreased to 40%, which is still higher than 0% survival for untreated or vehicle-treatment, but there was no statistical difference between 6j treatment (2 dpi) and the untreated or vehicle-treated group (FIG. 6D) ($p<0.05$). 6j treatment started on 3 dpi also failed to statistically improve survival of mice compared to the untreated or vehicle-treated group (FIG. 6D) ($p<0.05$). All mice lost body weight following virus infection, but surviving mice treated with 6j regained the lost weight by 15 dpi (FIG. 1E). Recovery of body weight was faster in mice treated from 1 dpi than from 2 dpi (FIG. 6E). These results show that survival of mice markedly increased when 6j is given to mice at 1 dpi, and the antiviral effect of 6j in the mouse model is greater than 6h with better survival rates and faster recovery of body weight (FIGS. 6D and E) ($p<0.05$). These findings emphasize the importance of early intervention to attain positive clinical outcome.

Figure 7:
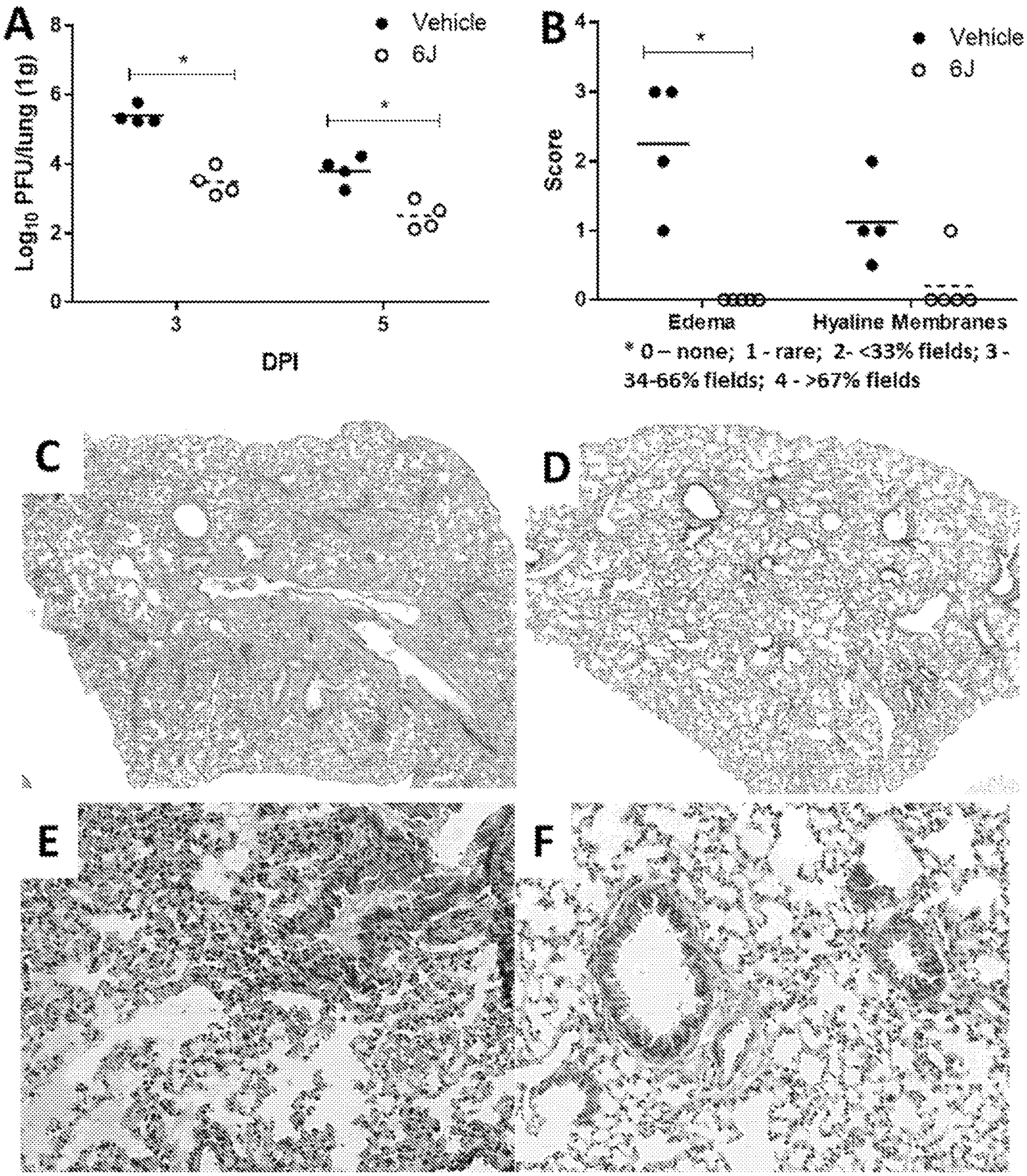
FIG. 7 shows lung virus titers and histopathology of hDPP4-KI mice infected with $MERS_{MA}$. hDPP4-KI mice were infected with $MERS_{MA}$-COV at 0 dpi and then were treated with vehicle as a control or with compound 6j starting at 1 dpi until euthanasia (n=4 or 5 per group). (A) Lungs were collected, and virus titers were measured at 3 and 5 dpi. Lungs were examined for edema and for hyaline membrane formation (B), and lung sections were stained with hematoxylin and eosin stain for histopathology at 6 dpi (C to F). (B) Tissues were scored for edema and hyaline membrane formation using the scale: 0, none; 1, rare (<5 alveoli); 2, <33% of lung fields; 3, 34 to 66% lung fields, and 4, >66% lung fields (30). (C) to (F) show representative histopathology images for vehicle control in (C) and (E) and compound 6j treatment in (D) and (F) at 40×[(C) and (D)] or 100×[(E) and (F)]. Asterisks indicate P<0.01 by multiple t tests.

Lung virus titers and edema significantly reduced with compound 6j treatment. The lung pathology caused by $MERS_{MA}$ infection in hDPP4-KI mice closely resembles that of severe human MERS infection with diffuse alveolar damage, pulmonary edema, hyaline membrane formation, and infiltration of lymphocytes in the alveolar septa (24). A group of mice were infected with virus and treated with 6j or vehicle starting from 1 dpi, and their lungs were collected for the determination of virus load (3 and 5 dpi) or histopathology (6 dpi). Lung virus titers significantly decreased in the treated mice on both days ($P<0.05$) (FIG. 7A). Edema in the lungs from the treated mice were statistically significantly reduced compared to vehicle-treated mice ($P<0.05$) (FIG. 7B-F). Scores for hyaline membranes were reduced in 6j-treated mice but statistically not different from vehicle-treated mice. As reported before, MERS-CoV infection with vehicle treatment produced patchy consolidation (FIGS. 7C and E) variably composed of cellular inflammation, vascular congestion, and atelectasis. The airways were generally intact, with only scattered, uncommon sloughed cells (FIGS. 7C and E). In some lungs, lymphatic vessels were filled with degenerative cells and cellular debris (FIGS. 7C and E). Alveolar edema was detected in some lung fields (FIGS. 7C and E). However, little lesion by MERS-CoV infection was observed in lungs with 6j treatment (FIGS. 7D and F), which supports the survival analysis by 6j treatment.

While there are currently no approved vaccines or small molecule therapeutics for the treatment of MERS-CoV or SARS-CoV infection, numerous preventive and treatment options are in development. The most clinically advanced antiviral compound with a broad-spectrum capacity is Remdesivir, a nucleoside analogue. It was originally developed as an Ebola virus antiviral drug and also shown to be highly effective against both MERS-CoV and SARS-CoV in cell culture and in animal models. With a mouse model, the prophylactic treatment (but not therapeutic treatment) of Remdesvir can significantly reduce MERS-CoV mediated weight loss, lung virus titers and lung injury scores compared to vehicle-treated mice. In summary, we generated 3CLpro inhibitors highly potent against multiple coronaviruses including SARS-CoV-2, demonstrated the proof-of-concept therapeutic efficacy of an inhibitor using the hDPP4-KI mouse model with significantly increased survival of mice infected with MERS-CoV. These studies have laid a solid foundation for advancing this series further along the development pipeline.

Data and materials availability. Coordinates and structure factors for the MERS 3CLpro inhibitor complexes were deposited to the Worldwide Protein Data Bank (wwPDB) with the accession codes: MERS-CoV 3CLpro with inhibitor 6b (6VGY), 6d (6VGZ), 6g (6VH0), 6h (6VH1), 7i (6VH2) and 7j (6VH3). SARS-CoV 3CLpro with inhibitor 7j (6W2A).

Example 2

Additional Compounds

Compounds were synthesized according to Scheme 2 (denoted by "S2" below; see also FIG. 8), each including the indicated warhead (Z group) and glutamine surrogate:

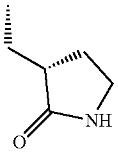

Figure 8:
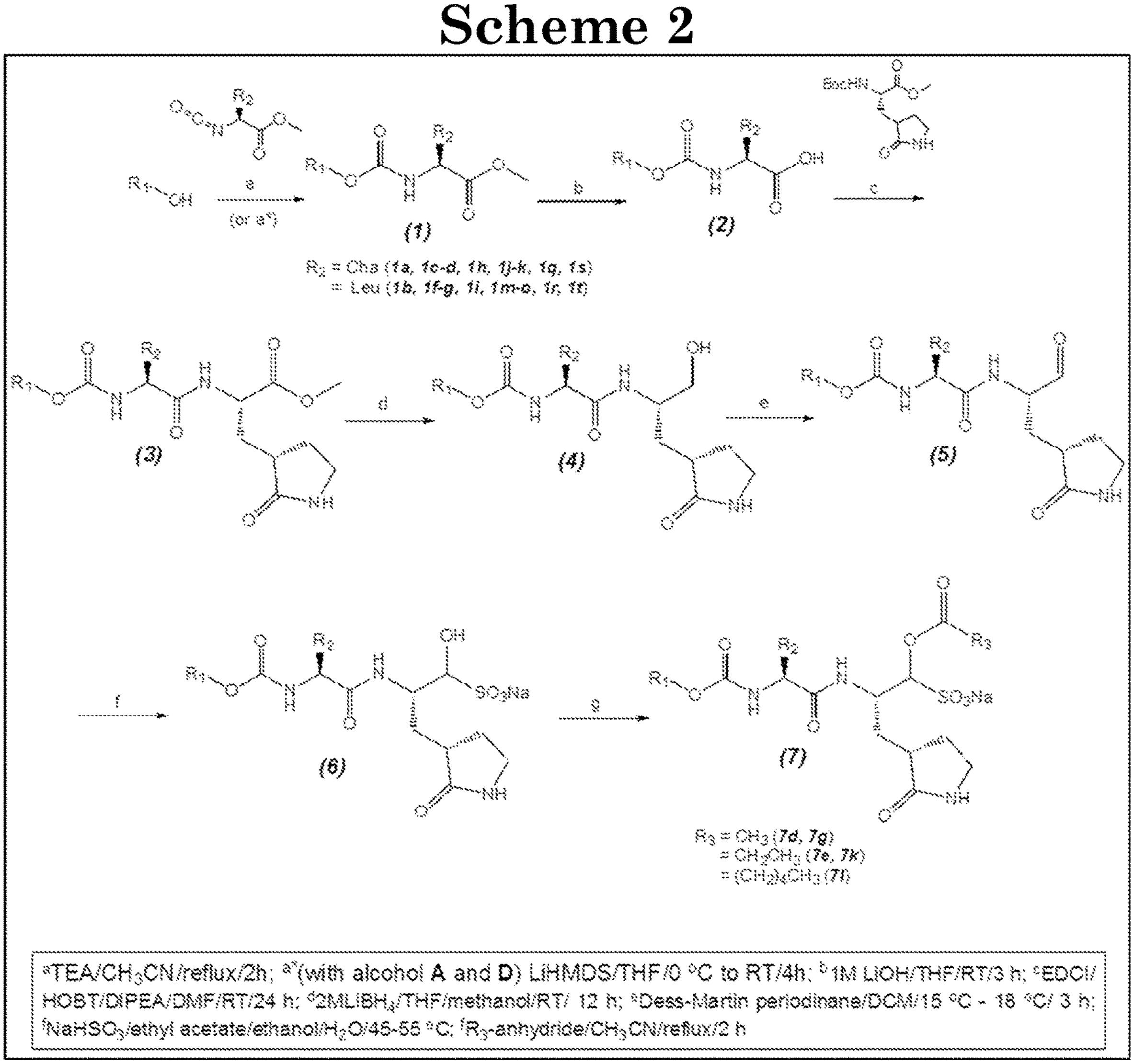
FIG. 8 shows reaction Scheme 2 for the stepwise compound synthesis with intermediate compounds for 3C-like protease (3CLpro) inhibitors of the S2-1-7 series, similar to Scheme 1.
Figure 9:
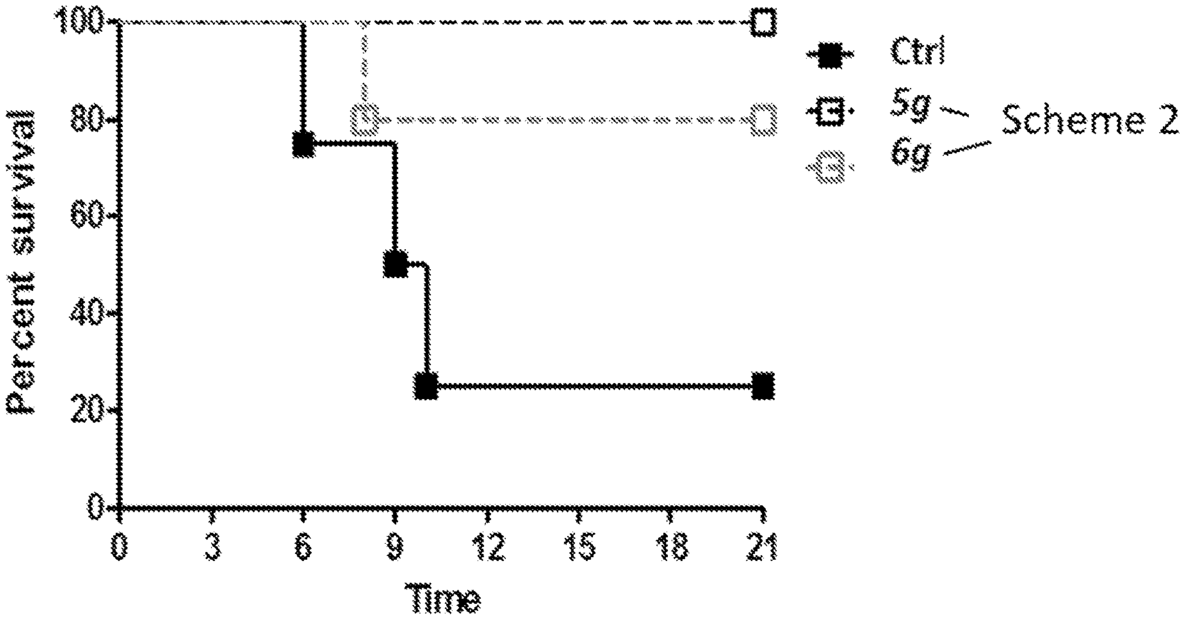
FIG. 9 shows the therapeutic treatment of compound S2-5g and S2-6g in the hDPP4-KI mice infected with $MERS_{MA}$. The hDPP4-KI mice infected with $MERS_{MA}$ (N=5) were treated with compound S2-5g or S2-6g (from Scheme 2) starting at 1 dpi and survival was monitored for 21 days. Each compound was given at daily from 1-11 dpi, 50 mg/kg, i.p. once per day. Control mice (ctrl) received vehicle.

Results from treating hDPP4-KI mice infected with $MERS_{MA}$ (N=5) with compound S2-5g or S2-6g are in FIG. 9. See also Tables 4-6, and Scheme 2 (FIG. 8). Advantageously, these compounds have also exhibited efficacy against norovirus in a separate study (see also Example 5). The inhibitory activity of the synthesized compounds against NV 3CLpro and their anti-norovirus activity in a cell-based replicon system were evaluated. The determined $IC_{50}$ values in enzyme assay, $EC_{50}$ values against NV in the replicon harboring cells (HG23 cells), and $CC_{50}$ values in HG23 cells are shown in the corresponding tables and are the average of at least two determinations.

TABLE 4A

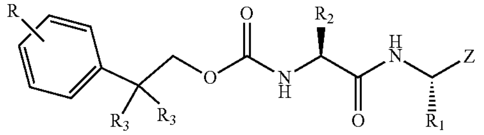

| Compound (Scheme 2) | R | $R_2$ | $R_3$ | Z | MERS-CoV $IC_{50 (\mu M)}$ Enzyme | MERS-CoV $EC_{50 (\mu M)}$ Cell culture | SARS-CoV-2 $IC_{50}$ (μM) enzyme | SARS-CoV-2 $EC_{50}$ (μM) Cell culture |
|---|---|---|---|---|---|---|---|---|
| 5c | H | Cha | $CH_3$ | CHO | 0.07 | ND | 0.7 | ND |
| 6c | | | | $CH(OH)SO_3Na$ | 0.05 | ND | 0.8 | ND |
| 5d | m-Cl | | | CHO | 1.9 | ND | ND | ND |
| 6d | | | | $SO_3Na$ | 1.8 | ND | ND | ND |
| 7d | | | | $[O(C{=}O)CH_3]SO_3Na$ | 9.1 | ND | ND | ND |
| 7e | | | | $[O(C{=}O)CH_2CH_3]SO_3Na$ | 8.5 | ND | ND | ND |
| 5f | H | Leu | | CHO | 0.8 | ND | ND | ND |
| 6f | | | | $CH(OH)SO_3Na$ | 0.9 | ND | ND | ND |
| 5g | m-Cl | | | CHO | 0.08 | 0.05 | 0.3 | 0.18 |
| 6g | | | | $CH(OH)SO_3Na$ | 0.07 | 0.05 | 0.3 | 0.15 |
| 7g | | | | $[O(C{=}O)CH_3]SO_3Na$ | 0.2 | ND | ND | ND |

* R preferably in meta position $R_1$ is glutamine surrogate

TABLE 4B

Cell-based Activity, and Cell-cytotoxicity Values against Norovirus 3CL Protease

| Compound | $IC_{50}$ (μM) ± SD | $EC_{50}$ (μM) ± SD | $CC_{50}$ (μM) ± SD |
|---|---|---|---|
| 5c | 0.45 ± 0.07 | 0.6 ± 0.14 | 80.1 ± 2.12 |
| 6c | 0.32 ± 0.06 | 0.5 ± 0.14 | 83.9 ± 0.9 |
| 5d | 0.23 ± 0.04 | 0.07 ± 0.01 | 13.3 ± 1.27 |
| 6d | 0.2 ± 0.07 | 0.08 ± 0.03 | 14.3 ± 5.66 |
| 7d | 0.09 ± 0.01 | 0.15 ± 0.07 | 67.0 ± 2.83 |
| 7e | 0.07 ± 0.01 | 0.22 ± 0.11 | 70.5 ± 3.54 |
| 5f | 0.45 ± 0.07 | 0.65 ± 0.07 | >100 |
| 6f | 0.4 ± 0.04 | 0.45 ± 0.07 | >100 |
| 5g | 0.27 ± 0.04 | 0.17 ± 0.05 | >100 |
| 6g | 0.3 ± 0.01 | 0.19 ± 0.1 | >100 |
| 7g | 0.13 ± 0.04 | 0.45 ± 0.21 | >100 |

TABLE 5A

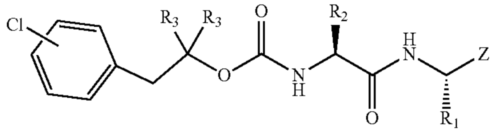

| Compound Scheme 2 | $R_2$ | $R_3$ | Z | MERS-CoV $IC_{50}$ (uM) enzyme |
|---|---|---|---|---|
| 5h | Cha | $CH_3$ | CHO | >10 |
| 6h | | | $CH(OH)SO_3Na$ | 1.5 |
| 5i | Leu | | CHO | 1.1 |
| 6i | | | $CH(OH)SO_3Na$ | 0.9 |

* Cl preferably in meta position $R_1$ is glutamine surrogate.

TABLE 5B

In Vitro and Cell-based Activity, and Cell-cytotoxicity Values against Norovirus 3CL Protease

| Compound | $R_2$ | Z | $IC_{50}$ (μM) ± SD | $EC_{50}$ (μM) ± SD | $CC_{50}$ (μM) ± SD |
|---|---|---|---|---|---|
| 5h | Cha | CHO | 7.7 ± 1.7 | 5.4 ± 1.1 | 15.6 ± 1.8 |
| 6h | | $CH(OH)SO_3Na$ | 6.8 ± 1.2 | 2.9 ± 0.5 | 20.4 ± 1.3 |
| 5i | Leu | CHO | 1.2 ± 0.5 | 0.9 ± 0.21 | >100 |
| 6i | | $CH(OH)SO_3Na$ | 1.0 ± 0.14 | 0.7 ± 0.14 | >100 |

TABLE 6A

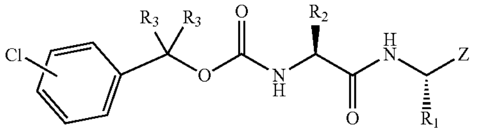

| Compound Scheme 2 | $R_2$ | Z | MERS-CoV $IC_{50}$ (uM) enzyme |
|---|---|---|---|
| 5a | Cha | CHO | 11.5 |
| 6a | | $CH(OH)SO_3Na$ | 24.1 |
| 5b | Leu | CHO | >25 |
| 6b | | $CH(OH)SO_3Na$ | >25 |

* Cl preferably in meta position
$R_1$ is glutamine surrogate.

TABLE 6B

In Vitro and Cell-based Activity, and Cell-cytotoxicity Values against Norovirus 3CL Protease

| Compound | $R_2$ | Z | $IC_{50}$ (μM) ± SD | $EC_{50}$ (μM) ± SD | $CC_{50}$ (μM) ± SD |
|---|---|---|---|---|---|
| 5a | Cha | CHO | 2.9 ± 0.9 | 3.7 ± 2.3 | >100 |
| 6a | | $CH(OH)SO_3Na$ | 2.7 ± 0.14 | 2.9 ± 0.1 | >100 |
| 5b | Leu | CHO | 3.8 ± 1.0 | 3.5 ± 0.1 | >100 |
| 6b | | $CH(OH)SO_3Na$ | 3.3 ± 0.5 | 1.8 ± 0.4 | >100 |

Example 3

The synthesis of the compounds shown are readily accomplished using previously published procedures to make the appropriate precursor 2-methyl-2-aryloxypropanoic acids followed by treatment with carbonyl diimidazole and sodium borohydride to furnish the corresponding alcohols which were then used to make the inhibitors using Scheme 2. The precursor thioaryloxyacids were made using a published procedure followed by reduction to yield the alcohols which were then used to make the inhibitors using Scheme 2. Substituted phenyl compounds in the X position are synthesized accordingly:

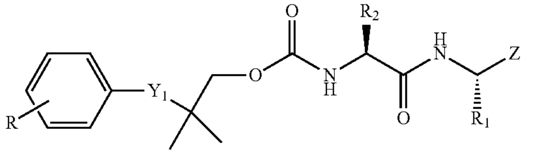

where R is H, p-Cl, m-Cl, m-F, p-F, m-OCH3, $Y_1$ is O or $S(=O)_o$ where o is 0, 1, or 2; $R_1$, $R_2$, and Z are defined as above.

Specific examples include the following, which have demonstrated efficacy against SARS-CoV-2 3CLpro:

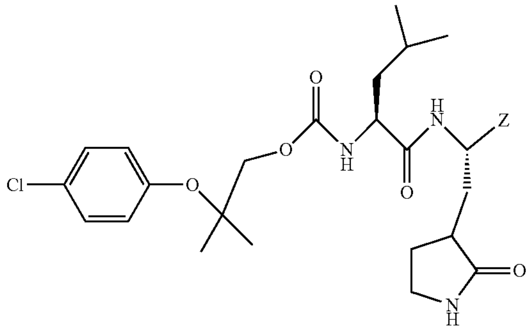

| Z | | $IC_{50}$ against SARS-CoV-2 3CLpro (uM) |
|---|---|---|
| CHO | MM-II-42 | 0.26 |
| $CH(OH)SO_3Na$ | MM-II-43 | 0.24 |

Additional compounds synthesized include:

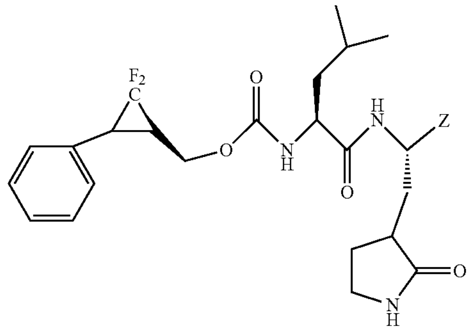

| Z | | | $IC_{50}$ against SARS-CoV-2 3CLpro (uM) |
|---|---|---|---|
| CHO | GC1269 | CSD-III-148 | 0.14 |
| $CH(OH)SO_3Na$ | GC1270 | CSD-III-149 | 0.16 |

Additional iterations include:

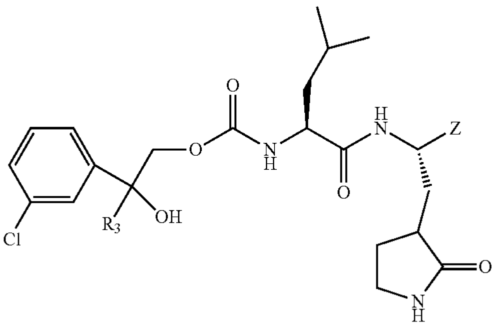

where $R_3$ is a branched or unbranched alkyl group, preferably methyl, ethyl, and n-propyl.

Additional cyclopropane compounds are synthesized in accordance with the reaction schemes described herein where X in the basic backbone design is further defined as depicted below.

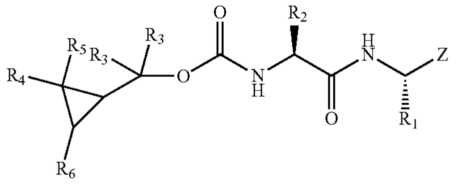

where each $R_1$ is glutamine or imidazole surrogate:

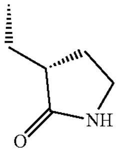

each $R_2$ is branched or unbranched alkyl, cycloalkyl, aryl, arylalkyl, alkenyl, alkynyl, natural or unnatural amino acid side chain, bicyclic or tricyclic side chain, or a combination thereof, and in particular leucine (Leu), cyclohexylalanine (Cha), or a fluorinated side chain;

each $R_3$ is selected from the group consisting of —H, branched or unbranched alkyls (e.g., methyl, ethyl, butyl, isobutyl), substituted or unsubstituted aryls (e.g., phenyl, substituted phenyl), arylalkyl (e.g., benzyl or group where the aryl is naphthyl), and the like;

each $R_4$, $R_5$ and $R_6$ is independently selected from the group consisting of —H, branched or unbranched alkyls (e.g., methyl, ethyl, butyl, isobutyl), halogen (F, Cl, Br), halogenated alkyl, substituted or unsubstituted aryl (e.g., phenyl, substituted phenyl), arylalkyl, and cyclopropane ring (cis and/or trans); and each Z is selected from the group consisting of $C_1$-$C_6$ hydroxyalkyl, aldehydes, alpha-ketoamides, and bisulfite salts, and in particular —$CH_2OH$, —CHO, —$CH(OH)SO_3^-Na^+$, and —$[O(C{=}O)R_w]SO_3^-Na^+$, where $R_w$ is an alkyl or arylalkyl with —$CH_3$ and —$CH_2CH_3$ being particularly preferred.

Additional series of cycloalkane compounds are synthesized:

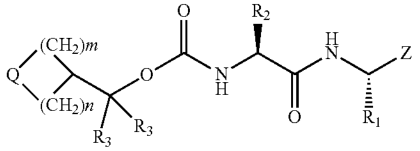

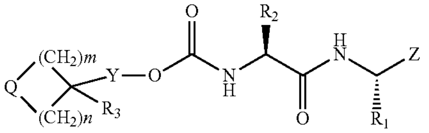

including macrocyclic derivatives thereof.

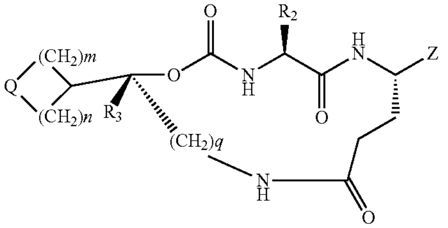

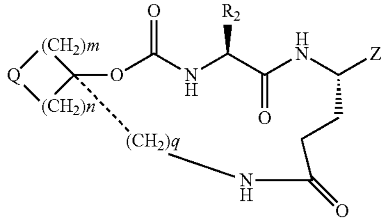

where m and n are each 1-3;

each q is 1-6;

each $R_1$ is a Gln or imidazole surrogate;

each $R_2$ is a branched or unbranched alkyl, cycloalkyl, aryl, arylalkyl, alkenyl, alkynyl, natural or unnatural amino acid side chain, bicyclic or tricyclic side chain, or a combination thereof, and in particular leucine (Leu), cyclohexylalanine (Cha), or a fluorinated side chain;

each $R_3$ is selected from the group consisting of —H, branched or unbranched alkyls (e.g., methyl, ethyl, butyl, isobutyl), substituted or unsubstituted aryls (e.g., phenyl, substituted phenyl), arylalkyl (e.g., benzyl or group where the aryl is naphthyl), and the like;

each Q is selected from branched or unbranched alkyls (e.g., methyl, ethyl, propyl, isopropyl, butyl, isobutyl), $C(CH_3)_2$, CHF, $CF_2$, or $CHCF_3$;

$Y{=}(CR_iR_j)_o$, where o can be 0 (meaning Y is not present and the oxygen is directly bonded to carbon of the ring) or 1 (meaning Y=CRiRj where Ri and Rj can both be H, or both methyl, or one H and the other methyl, or deuterated derivatives thereof; o can also be 3 or more, but 0 and 1 are preferred; and each Z is selected from the group consisting of $C_1$-$C_6$ hydroxyalkyl, aldehydes, alpha-ketoamides, and bisulfite salts, and in particular —$CH_2OH$, —CHO, —$CH(OH)SO_3^-Na^+$, and —$[O(C{=}O)R_w]SO_3^-Na^+$, where $R_w$ is an alkyl or arylalkyl with —$CH_3$ and —$CH_2CH_3$ being particularly preferred.

Example 4

Structure-Guided Design of Potent Inhibitors of SARS-CoV-2 3CL Protease

Introduction

The SARS-CoV-2 life cycle encompasses multiple virus and host-based druggable targets that can be exploited, including for example inhibitors that block virus entry and fusion, and replication inhibitors targeting the 3CL and papain-like proteases and the RNA-dependent RNA polymerase, among others. Attractive host-based targets include the proteases transmembrane serine protease 2 (TMPRSS2), cathepsin L, and furin. Thus, the development of small molecule therapeutics that target host or viral targets essential for viral replication is a potentially fruitful avenue of investigation. SARS-CoV-2 3CLpro is a homodimer with a catalytic Cys-His dyad ($Cys^{145}$-$His^{41}$) and an extended binding cleft. The protease displays a strong preference for a —Y-Z-Leu-Gln-X sequence, corresponding to the subsites -$S_4$-$S_3$-$S_2$-$S_1$-$S_1$'-, where X is a small amino acid (Ser, Ala, Gly), Y is small hydrophobic amino acid, and Z is solvent exposed and can tolerate polar or nonpolar amino acid chains. SARS-CoV-2 3CLpro is therefore an attractive target for drug development.

We recently described the structure-guided design of a dipeptidyl series of MERS-CoV and SARS-CoV-2 3CL protease inhibitors incorporating in their structure a piperidine or cyclohexyl moiety capable of engaging in favorable binding interactions with the $S_4$ pocket (see above examples). We furthermore demonstrated that members of the cyclohexyl series of compounds improve survival in a mouse model of MERS-CoV infection. We report herein the results of structure-guided studies intended to interrogate the effects of stereochemistry, conformation, and structure, including the systematic introduction of fluorine (F-walk) around the structure of clinical candidate, GC376, and the synthesis of deuterated inhibitors, to modulate pharmacological activity, pharmacokinetic properties, and oral bioavailability.

Results and Discussion

Figure 10A:
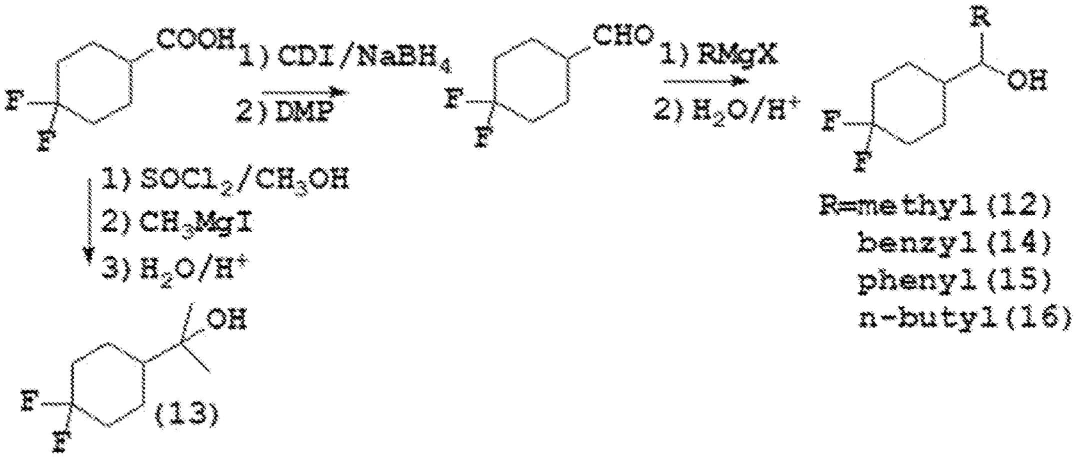
FIG. 10A shows the reaction scheme for the synthesis of precursor alcohols 12-16.

Chemistry. The new synthesis scheme for inhibitors 1-24b/c differs from Schemes 1 and 2 entailed the use of a structurally-diverse set of precursor alcohols (Table 10), some of which were commercially available. Schemes 1 and 2 rely on linear synthesis for making the inhibitors, involving more steps and more purifications, and in some cases, lower final yields of products. The new scheme involves a convergent synthesis which involves the synthesis of two separate fragments which are then linked together, resulting in fewer steps, higher yields of products, less tedious (fewer purifications) protocols. Briefly, Alcohols 12-16 and 13 were readily synthesized from 4,4-difluorocyclohexane carboxylic acid via reduction to the corresponding alcohol by treatment with carbonyl diimidazole and sodium borohydride, followed by oxidation with Dess-Martin periodinane (DMP) reagent to yield the aldehyde. Subsequent treatment with an array of Grignard reagents generated alcohols 12, 14-16 (FIG. 10A). Alcohol 13 was synthesized by reacting the methyl ester of 4,4-difluorocyclohexane carboxylic acid with excess methyl magnesium iodide, followed by acidic work up. Deuterated alcohols 9, 11, 20, and 22 were obtained by treatment of the precursor carboxylic acid with carbonyl diimidazole followed by the addition of sodium borodeuteride. All trans-substituted alcohols were synthesized by reducing the precursor 4-substituted cyclohexanone with sodium borohydride/$CeCl_3$.

Figure 10B:
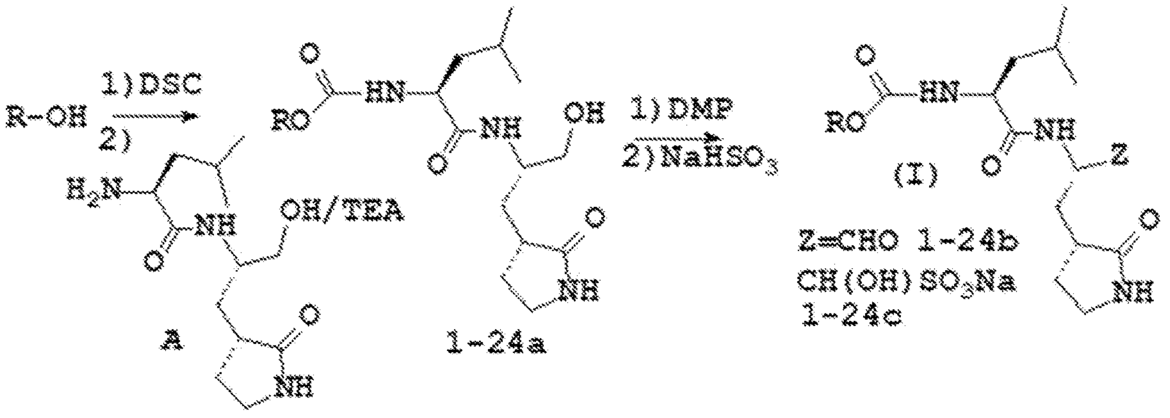
FIG. 10B shows the reaction scheme for the synthesis of inhibitors 1-24b-c.

Inhibitors 1-24b/c were obtained by reacting each precursor alcohol with disuccinimidyl carbonate, followed by coupling with amino alcohol A. The resulting product was treated with Dess-Martin periodinane to yield aldehydes 1-24b which were converted to the corresponding bisulfite adducts 1-24c upon treatment with sodium bisulfite (FIG. 10B). Thus, in FIG. 10B, the final compounds are designated as aldehydes (b) and bisulfite salts (c), while compounds designated as a refer to the intermediates. As such, for example, compounds 1b and 1c refer to the aldehyde and bisulfite salt versions of compound 1, respectively.

Figure 10C:
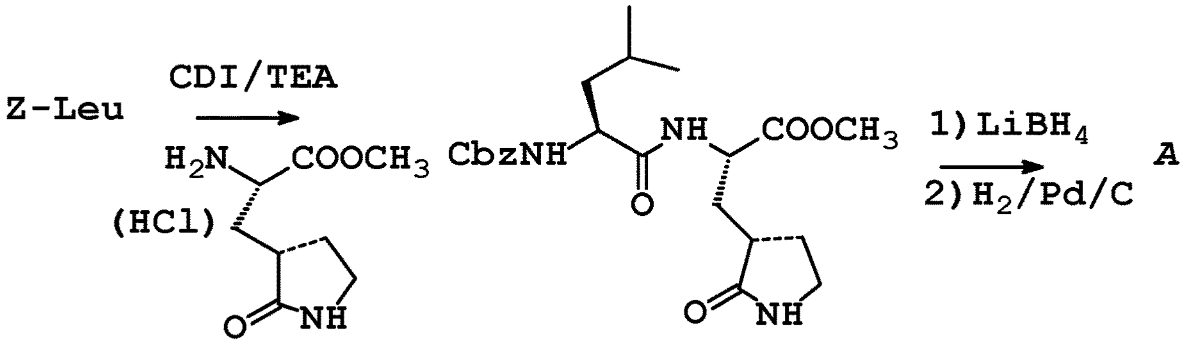
FIG. 10C shows the reaction scheme for the synthesis of the amino alcohol A.

An alternative synthesis was used in the case of inhibitors 6-8, 10-16, 23,24 which involved the reaction of the precursor alcohol with (L) leucine methyl ester isocyanate, as described in detail previously. The synthesis of precursor amino alcohol A is illustrated in FIG. 10C, and was readily accomplished by coupling (L) Z-Leu with a glutamine surrogate, followed by sequential reduction with $LiBH_4$ and removal of the protective group ($H_2$/Pd).

Biochemical Studies. The inhibitory activity of compounds 1-24b/c against SARS-CoV-2 3CL protease in biochemical assays and a cell-based system, were determined as described in the experimental section. The $IC_{50}$ values and the $CC_{50}$ values in Huh-7, CRFK, or CCL1 cells are summarized in Table 7 and they are the average of at least two determinations.

TABLE 7

$IC_{50}$ of inhibitors 1-24 against SARS-CoV-2 3CLpro and $CC_{50}$.

| Compound | $IC_{50}$ (μM) | $CC_{50}$ (μM) |
|---|---|---|
| 1b | 0.28 | >100 |
| 1c | 0.24 | >100 |
| 2b | 0.25 | >100 |
| 2c | 0.23 | >100 |
| 3b | 0.26 | >100 |
| 3c | 0.2 | >100 |
| 4b | 0.16 | >100 |
| 4c | 0.18 | >100 |
| 5b | 0.2 | >100 |
| 5c | 0.25 | >100 |
| 6b | 0.2 | >100 |
| 6c | 0.21 | >100 |
| 7b | 0.2 | >100 |
| 7c | 0.22 | >100 |
| 8b | 0.22 | >100 |
| 8c | 0.21 | >100 |
| 9b | 0.41 | >100 |
| 9c | 0.33 | >100 |
| 10b | 0.43 | >100 |
| 10c | 0.45 | >100 |
| 11b | 0.28 | >100 |
| 11c | 0.3 | >100 |
| 12b | 0.21 | >100 |
| 12c | 0.2 | >100 |
| 13b | 0.8 | >100 |
| 13c | 0.9 | >100 |
| 14b | 0.23 | >100 |
| 14c | 0.22 | >100 |
| 15b | 0.1 | >100 |
| 15c | 0.16 | >100 |
| 16b | 0.16 | >100 |
| 16c | 0.25 | >100 |
| 17b | 0.38 | >100 |
| 17c | 0.4 | >100 |
| 18b | 0.32 | >100 |
| 18c | 0.31 | >100 |
| 19b | 0.36 | >100 |
| 19c | 0.38 | >100 |
| 20b | 0.35 | >100 |
| 20c | 0.36 | >100 |
| 21b | 0.33 | >100 |
| 21c | 0.36 | >100 |

TABLE 7-continued $IC_{50}$ of inhibitors 1-24 against SARS-CoV-2 3CLpro and $CC_{50}$.

| Compound | $IC_{50}$ (μM) | $CC_{50}$ (μM) |
|---|---|---|
| 22b | 0.63 | >100 |
| 22c | 0.45 | >100 |
| 23b | 0.15 | >100 |
| 23c | 0.18 | >100 |
| 24b | 4.1 | >100 |
| 24c | 3.5 | >100 |

For comparative purposes, the inhibitory activity of additional compounds against MERS-CoV 3CL protease was also determined as described previously and the $IC_{50}$ values are listed in Table 8.

TABLE 8

$IC_{50}$ values of selected compounds against MERS-CoV 3CLpro.

| Compound | $IC_{50}$ (μM) |
|---|---|
| 1c | 0.09 |
| 4c | 0.15 |
| 8c | 0.11 |
| 12c | 0.12 |
| 14c | 0.16 |
| 18c | 0.08 |
| 21c | 0.07 |
| 23c | 0.13 |

X-Ray Crystallographic Studies. A series of high resolution cocrystal structures were determined to elucidate the interaction of the inhibitors with the active site of SARS-CoV-2 3CLpro. Specifically, we sought to confirm the mechanism of action, identify the structural determinants associated with the binding of the inhibitors to the active site of the protease and ultimately harness the accumulated structural information and insights gained to further optimize pharmacological activity and PK parameters. Three groups of inhibitor types were analyzed with respect to their functional groups that interact within the $S_4$ subsite which are 1) non-polar substituents, 2) 4,4-difluorocyclohexyl groups that are connected to a stereocenter and, 3) fluorinated aryl compounds based on the structure of GC376.

For all structures described in this Example, the active sites contained prominent difference electron density consistent with inhibitors covalently bound to Cys 145. Additionally, the electron density was consistent with both the R and S enantiomers at the stereocenter formed by covalent attachment of the Sg atom of Cys 145 and were therefore, modeled as each enantiomer with 0.5 occupancy. The γ-lactam ring of the inhibitor forms direct hydrogen bonds with Glu166 and His163, and Glu166 and Gln189 form additional H-bonds with the C═O and NH of the carbamate moiety in the inhibitor. The inhibitor engages in hydrophobic interactions with the leucine side chain, which is snugly accommodated in the $S_2$ pocket. The cocrystal structure confirms that the reaction of Cys145 with the aldehyde warhead results in the formation of a tetrahedral hemithioacetal that is stabilized by a H-bond to His164.

TABLE 9

Crystallographic data for SARS-CoV-2 3CLpro inhibitor complexes

| Data Collection | NN-II-111 (8b) | AMJ-I-106 (12b) | CSD-III-008 (19b) | CSD-III-009 (20b) | AMJ-I-158 (1c) | AMJ-I-159 (3c) |
|---|---|---|---|---|---|---|
| Unit-cell (Å, °) | a = 113.40<br>b = 52.99<br>c = 46.61<br>β = 102.7 | a = 55.40<br>b = 98.97<br>c = 59.15<br>β = 108.3 | a = 55.47<br>b = 98.59<br>c = 58.59<br>β = 108.3 | a = 55.00<br>b = 98.27<br>c = 58.17<br>β = 107.5 | a = 55.26<br>b = 98.37<br>c = 58.76<br>β = 107.9 | a = 114.17<br>b = 53.23<br>c = 46.00<br>β = 102.6 |
| Space group | C2 | $P2_1$ | $P2_1$ | $P2_1$ | $P2_1$ | C2 |
| Resolution (Å)[1] | 47.79-1.55 (1.58-1.55) | 48.83-1.60 (1.63-1.60) | 48.77-1.60 (1.63-1.60) | 29.14-2.20 (2.27-2.20) | 49.19-1.65 (1.68-1.65) | 48.03-1.85 (1.89-1.85) |
| Wavelength (Å) | 1.0000 | 1.0000 | 1.0000 | 1.0000 | 1.0000 | 1.0000 |
| Temperature (K) | 100 | 100 | 100 | 100 | 100 | 100 |
| Observed reflns | 270,384 | 260,948 | 261,946 | 103,525 | 247,291 | 158,821 |
| Unique reflns | 39,266 | 77,930 | 78,513 | 29,889 | 71,150 | 23,121 |
| <I/σ(I)>[1] | 10.5 (1.7) | 12.5 (2.4) | 14.7 (2.1) | 7.9 (1.9) | 10.7 (1.7) | 11.4 (1.9) |
| Completeness (%)[1] | 100 (100) | 97.8 (75.6) | 99.9 (89.0) | 99.7 (99.9) | 99.2 (98.9) | 100 (100) |
| Multiplicity[1] | 6.9 (7.1) | 3.3 (2.5) | 3.3 (2.2) | 3.5 (3.2) | 3.5 (3.6) | 6.9 (6.7) |
| $R_{merge}$ (%)[1,2] | 9.3 (134.9) | 5.4 (35.2) | 4.1 (35.9) | 10.1 (62.2) | 5.3 (70.4) | 8.5 (97.9) |
| $R_{meas}$ (%)[1,4] | 10.1 (145.5) | 6.4 (43.9) | 4.9 (46.8) | 12.0 (74.6) | 6.3 (82.7) | 9.2 (106.2) |
| $R_{pim}$ (%)[1,4] | 3.8 (54.2) | 3.4 (25.7) | 2.6 (29.5) | 6.4 (40.8) | 3.3 (43.0) | 3.5 (40.9) |
| $CC_{1/2}$[1,5] | 0.998 (0.655) | 0.997 (0.855) | 0.998 (0.877) | 0.995 (0.812) | 0.998 (0.756) | 0.998 (0.719) |
| Refinement | | | | | | |
| Resolution (Å)[1] | 34.63-1.55 | 37.12-1.60 | 37.04-1.60 | 36.78-2.20 | 36.94-1.65 | 39.39-1.85 |
| Reflections (working/test)[1] | 37,274/1,971 | 74,216/3,668 | 74,749/3,678 | 28,394/1,442 | 67,590/3,488 | 21,962/1,155 |
| $R_{factor}/R_{free}$ (%)[1,3] | 16.8/19.7 | 17.8/20.1 | 18.5/21.2 | 18.4/25.8 | 17.5/21.4 | 17.6/22.3 |
| No. of atoms (Protein/Ligand/Water) | 2,271/64/250 | 4,463/128/386 | 4,460/120/347 | 4,455/120/142 | 4,542/120/397 | 2,220/62/137 |
| Model Quality | | | | | | |
| R.m.s deviations | | | | | | |
| Bond lengths (Å) | 0.008 | 0.010 | 0.008 | 0.006 | 0.007 | 0.009 |
| Bond angles (°) | 0.964 | 1.073 | 0.913 | 0.779 | 0.955 | 1.009 |

TABLE 9-continued

Crystallographic data for SARS-CoV-2 3CLpro inhibitor complexes

| | | | | | | |
|---|---|---|---|---|---|---|
| Mean B-factor (Å$^2$) | | | | | | |
| All Atoms | 23.1 | 27.8 | 29.8 | 39.8 | 29.8 | 35.5 |
| Protein | 22.2 | 27.1 | 29.3 | 39.7 | 29.2 | 35.5 |
| Ligand | 18.7 | 29.1 | 28.8 | 46.0 | 29.7 | 30.5 |
| Water | 31.3 | 35.9 | 36.6 | 39.0 | 36.6 | 38.8 |
| Coordinate error (max. likelihood) (Å) | 0.17 | 0.20 | 0.18 | 0.32 | 0.19 | 0.22 |
| Ramachandran Plot | | | | | | |
| Most favored (%) | 98.7 | 98.5 | 97.5 | 96.8 | 97.8 | 97.3 |
| Add. allowed (%) | 1.3 | 1.5 | 2.5 | 3.1 | 2.2 | 2.4 |
| Data Collection | AMJ-I-157 (5c) | AMJ-I-114 (13c) | AMJ-I-111 (14c) | CSD-III-028 (17c) | CSD-III-029 (18c) | NN-II-123 (21c) |
| Unit-cell (Å, °) | a = 114.11 | a = 45.74 | a = 55.09 | a = 54.93 | a = 55.02 | a = 55.30 |
| Space group | b = 52.10 | b = 53.54 | b = 98.55 | b = 98.52 | b = 98.61 | b = 98.82 |
| | c = 46.27 | c = 113.42 | c = 59.01 | c = 58.38 | c = 58.34 | c = 58.86 |
| | β = 102.6 | β = 101.3 | β = 108.0 | β = 107.3 | β = 107.4 | β = 108.0 |
| | C2 | $P2_1$ | $P2_1$ | $P2_1$ | $P2_1$ | $P2_1$ |
| Resolution (Å)[1] | 47.93-2.00 (2.05-2.00) | 48.25-2.00 (2.05-2.00) | 48.77-1.65 (1.68-1.65) | 49.26-1.80 (1.84-1.80) | 49.31-2.00 (2.05-2.00) | 48.71-1.75 (1.78-1.75) |
| Wavelength (Å) | 1.0000 | 1.0000 | 0.9201 | 1.0000 | 1.0000 | 1.0000 |
| Temperature (K) | 100 | 100 | 100 | 100 | 100 | 100 |
| Observed reflns | 63,972 | 246,030 | 733,433 | 363,714 | 136,296 | 207,639 |
| Unique reflns | 18,397 | 36,653 | 71,947 | 54,764 | 39,124 | 60,377 |
| $\langle I/\sigma(I)\rangle$[1] | 7.5 (1.8) | 8.9 (1.9) | 8.7 (1.6) | 10.3 (1.8) | 10.3 (1.8) | 12.2 (1.8) |
| Completeness (%)[1] | 99.9 (99.9) | 100 (99.9) | 100 (100) | 99.7 (99.7) | 97.4 (99.9) | 99.7 (100) |
| Multiplicity[1] | 3.5 (3.6) | 6.7 (7.0) | 10.2 (9.8) | 6.6 (7.2) | 3.5 (3.5) | 3.4 (3.5) |
| $R_{merge}$ (%)[1,2] | 9.8 (71.2) | 9.4 (101.3) | 13.9 (138.1) | 8.0 (126.9) | 6.4 (72.3) | 5.7 (75.5) |
| $R_{meas}$ (%)[1,4] | 11.6 (83.7) | 10.2 (109.4) | 14.6 (145.7) | 8.7 (136.5) | 7.6 (85.2) | 6.8 (89.3) |
| Rpim (%)[14] | 6.2 (43.6) | 3.9 (41.1) | 4.6 (46.4) | 3.3 (50.1) | 4.0 (44.8) | 3.6 (47.3) |
| $CC_{1/2}$[1,5] | 0.995 (0.684) | 0.999 (0.866) | 0.997 (0.777) | 0.998 (0.859) | 0.998 (0.731) | 0.998 (0.740) |
| Refinement | | | | | | |
| Resolution (Å)[1] | 34.52-2.00 | 39.05-2.00 | 48.77-1.65 | 35.90-1.80 | 36.91-2.00 | 46.43-1.75 |
| Reflections (working/test)[1] | 17,509/880 | 34,747/1,748 | 68,149/3,505 | 51,801/2,676 | 37,222/1,858 | 57,492/2,830 |
| $R_{factor}/R_{free}$ | 17.2/22.9 | 21.1/26.5 | 17.8/22.4 | 18.1/24.1 | 18.3/24.9 | 18.0/22.3 |
| No. of atoms (Protein/Ligand/Water) | 2,243/68/130 | 4,366/132/221 | 4,480/152/293 | 4,456/106/200 | 4,477/106/105 | 4,496/136/283 |
| Model Quality | | | | | | |
| R.m.s deviations | | | | | | |
| Bond lengths (Å) | 0.009 | 0.010 | 0.011 | 0.008 | 0.009 | 0.008 |
| Bond angles (°) | 0.995 | 0.963 | 1.061 | 0.901 | 0.972 | 0.958 |
| Mean B-factor (Å$^2$) | | | | | | |
| All Atoms | 35.2 | 39.3 | 31.2 | 38.6 | 45.6 | 31.8 |
| Protein | 35.0 | 39.5 | 30.6 | 38.4 | 45.6 | 31.2 |
| Ligand | 33.7 | 33.1 | 37.0 | 37.9 | 47.5 | 39.2 |
| Water | 39.5 | 40.2 | 37.9 | 41.7 | 44.0 | 37.6 |
| Coordinate error (max. likelihood) (Å) | 0.26 | 0.30 | 0.21 | 0.22 | 0.28 | 0.21 |
| Ramachandran Plot | | | | | | |
| Most favored (%) | 97.0 | 97.8 | 98.7 | 98.5 | 96.6 | 98.3 |
| Add. allowed (%) | 3.0 | 2.1 | 1.3 | 1.5 | 3.4 | 1.7 |

[1]Values in parenthesis are for the highest resolution shell.

[2]$R_{merge} = \Sigma_{hkl}\Sigma_i |I_i(hkl) - \langle I(hkl)\rangle| / \Sigma_{hkl}\Sigma_i I_i(hkl)$, where $I_i(hkl)$ is the intensity measured for the ith reflection and $\langle I(hkl)\rangle$ is the average intensity of all reflections with indices hkl.

[3]$R_{factor} = \Sigma_{hkl} ||F_{obs}(hkl)| - |F_{calc}(hkl)|| / \Sigma_{hkl}|F_{obs}(hkl)|$; Rfree is calculated in an identical using 5% of randomly selected reflections that were not included in the refinement.

[4]$R_{meas}$ = redundancy-independent (multiplicity-weighted) $R_{merge}$. $R_{pim}$ = precision-indicating (multiplicity-weighted) $R_{merge}$

[5]$CC_{1/2}$ is the correlation coefficient of the mean intensities between two random half-sets of data.

Figure 11:
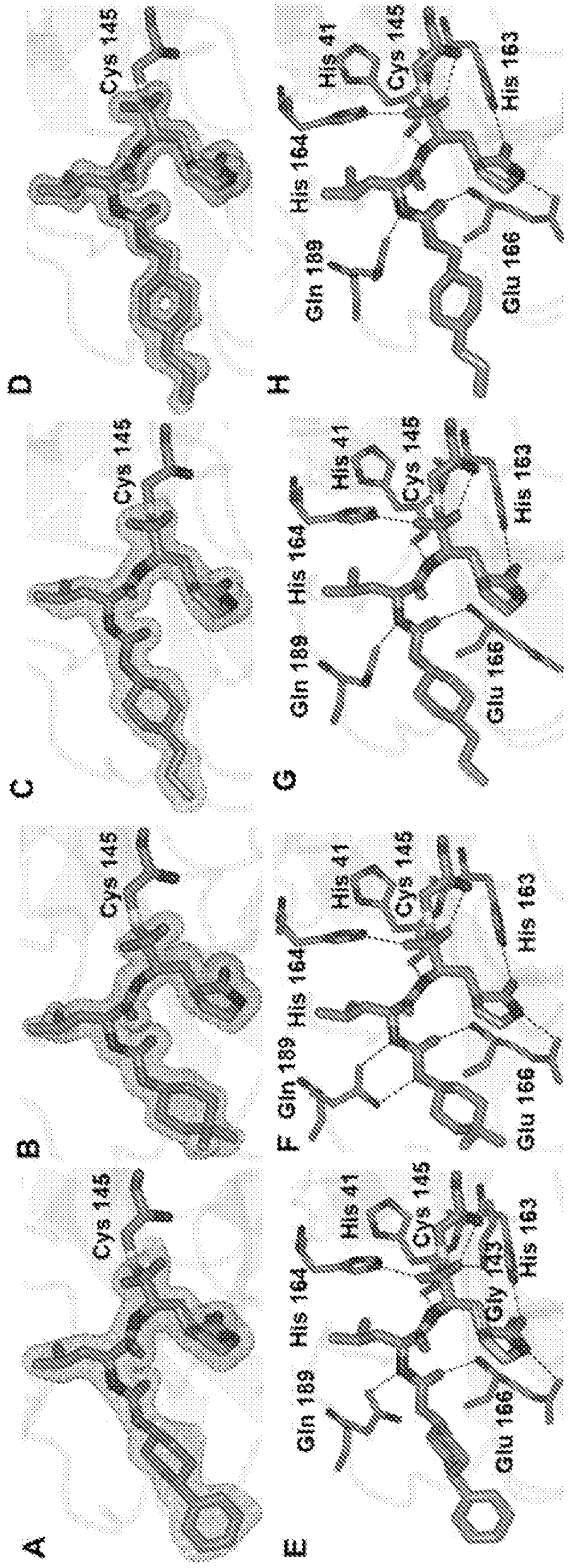
FIG. 11 shows the binding mode of inhibitors containing non-polar substituents. A/E) AMJ-I-157 (5c), B/F) AMJ-I-158 (1c), C/G) AMJ-I-159 (3c) and D/H)NN-II-111 (8b) with SARS-CoV-2 3CLpro. $F_o$-$F_c$ Polder omit map (A-D) contoured at 3σ. Hydrogen bond interactions (E-H) are drawn as dashed lines.
Figure 12:
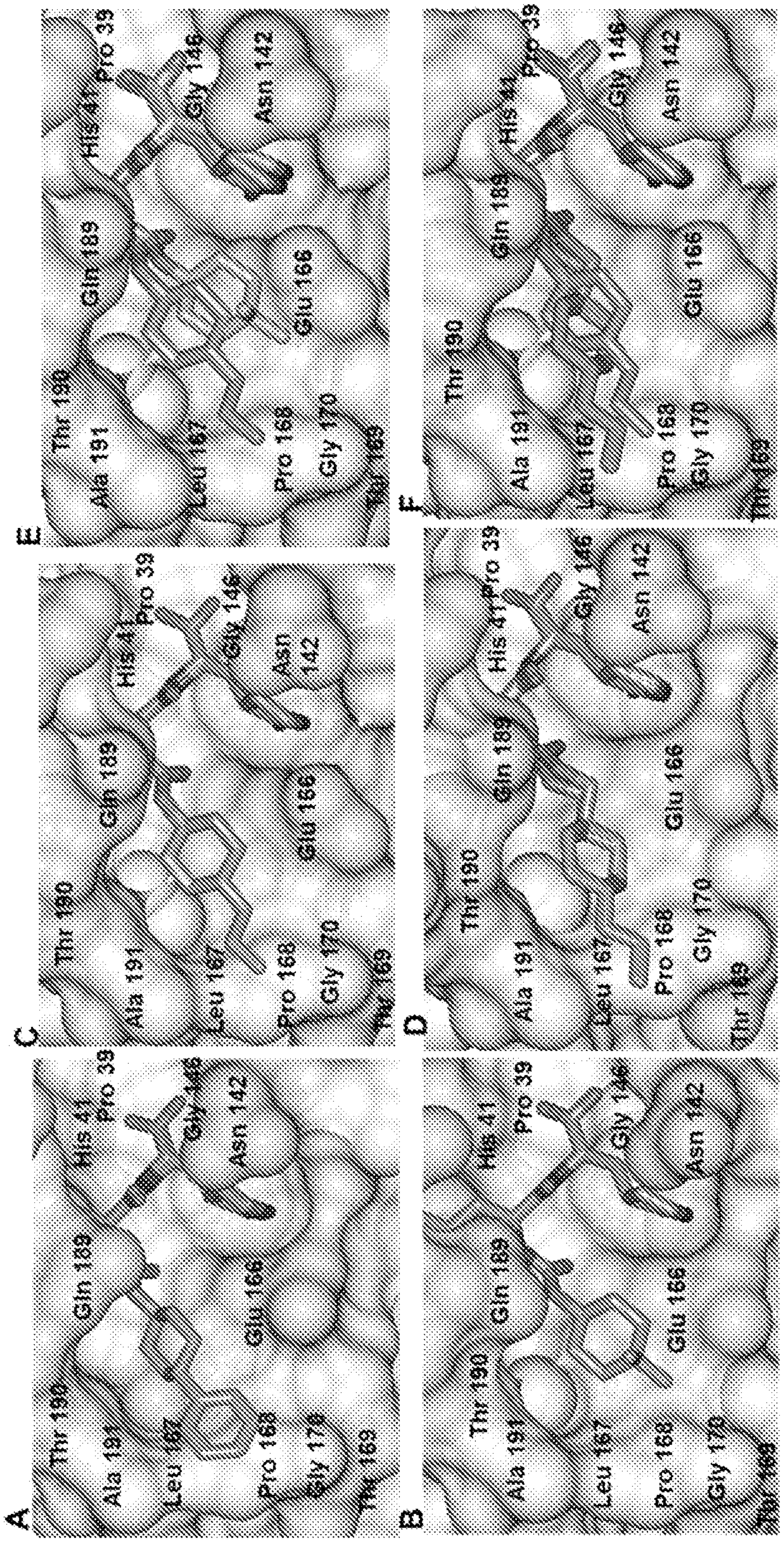
FIG. 12 shows the surface representation showing the orientation of non-polar groups near the S4 subsite of SARS-CoV-2 3CLpro with neighboring residues colored yellow (nonpolar), cyan (polar), and white (weakly polar). A) AMJ-I-157 (5c), B) AMJ-I-158 (1c), C) AMJ-I-159 (3c), D) NN-II-111 (8b). E) Superposition of AMJ-I-159 (3c) gray and AMJ-I-158 (1c) coral. F) Superposition of AMJ-I-159 (3c) gray and NN-II-111 (8b) magenta.

Non-polar substituents. The structures of 5c (AMJ-I-157), 1c (AMJ-I-158), 3c (AMJ-I-159) and 8b (NN-II-111) displayed well-defined electron density and similar hydrogen bond interactions as shown in FIG. 11. For all structures, the non-polar groups are mainly positioned within the $S_4$ subsite near a hydrophobic ridge formed by residues Leu 167, Pro 168, Gly 170 and Ala 191 (FIG. 12). However, the dimethyl cyclohexyl ring in 1c is too short to fully engage the hydrophobic ridge in the $S_4$ subsite (FIG. 12B). The addition of an n-propyl group in 3c permits further engagement with the hydrophobic cleft and the extra carbon atom in 8b allows the propyl group to extend even further (FIGS. 12C and 2D). Superposition of 3c and 1c (FIG. 12E) shows that the 4,4-dimethylcyclohexyl ring is moved slightly out of the $S_4$ subsite relative to the n-propyl group in 3c. Additionally, superposition of 3c and 8b revealed quite similar binding modes although the n-propyl group of 8b is positioned deeper within the $S_4$ subsite (FIG. 12F). Overall, the similar binding modes and attendant high potency of the inhibitors are reflected in their low $IC_{50}$ values and similar potencies (Table 7, compounds 1-5b/c). With respect to inhibitor 8, it was envisaged that the corresponding deuterated inhibitor 9, found to be nearly equipotent to non-deuterated inhibitor 8 (Table 7), would likely display improved PK properties.

Figure 13:
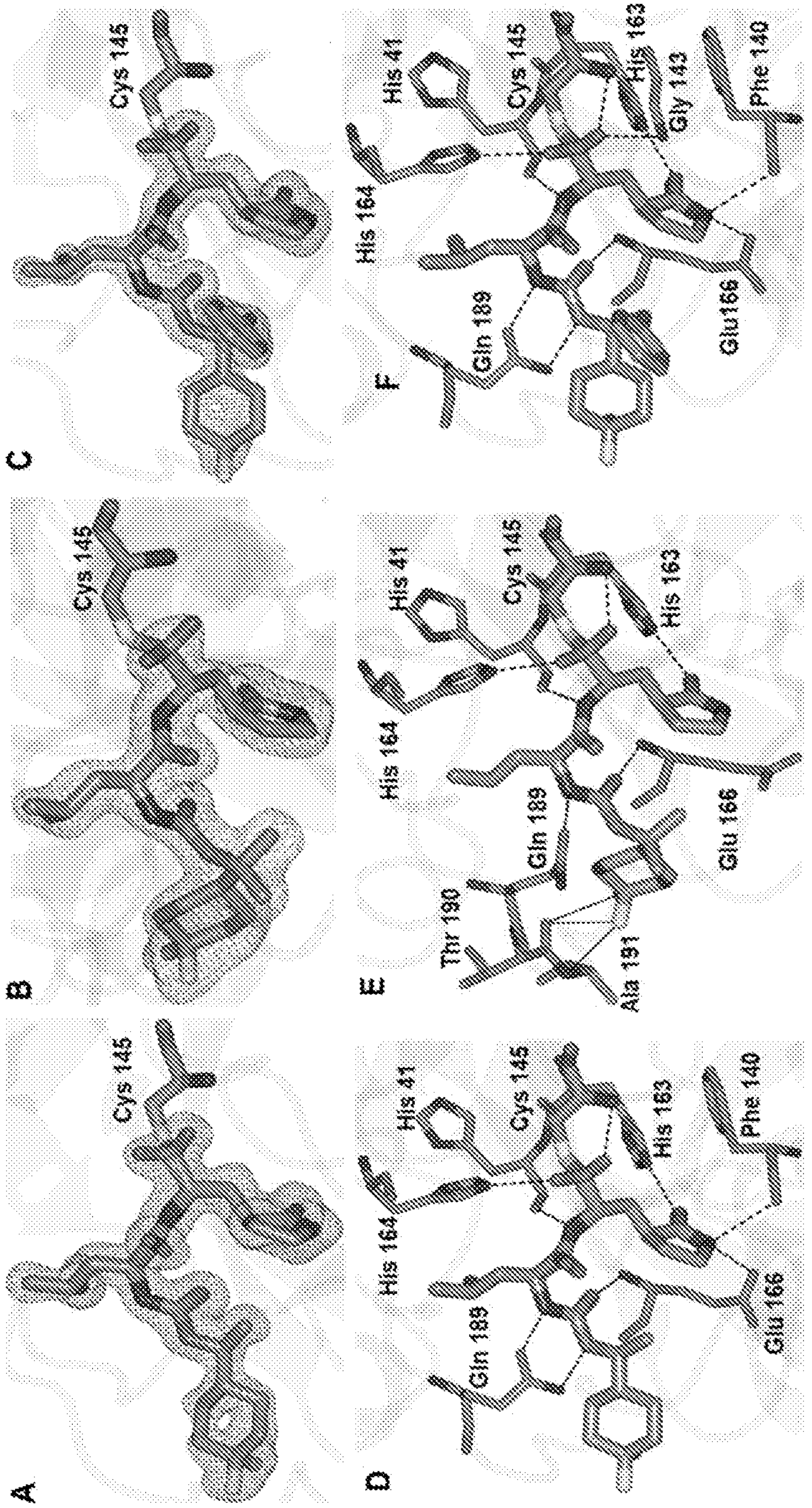
FIG. 13 shows the binding mode of inhibitors containing a 4,4-difluorocyclohexyl group. A/D) AMJ-I-108 (12b), B/E) AMJ-I-114 (13c) and C/F) AMJ-I-111 (14c) with SARS-CoV-2 3CLpro. $F_o$-$F_c$ Polder omit map (A-C) contoured at 3σ. Hydrogen bond interactions (D-F) are drawn as dashed lines.
Figure 14:
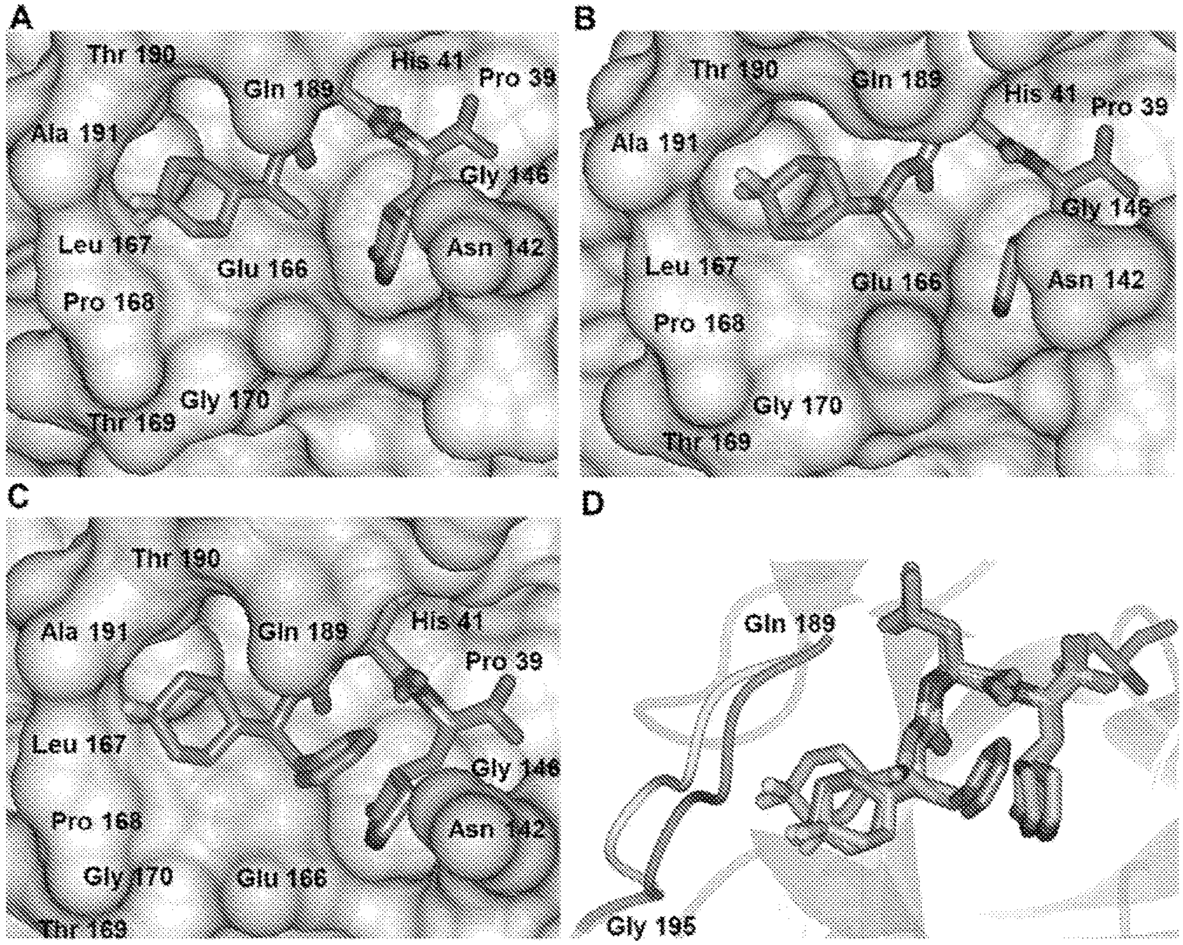
FIG. 14 shows the surface representation showing the orientation of the 4,4-difluorocyclohexyl groups near the S4 subsite of SARS-CoV-2 3CLpro with neighboring residues colored yellow (nonpolar), cyan (polar), and white (weakly polar). A) AMJ-I-108 (12b), B) AMJ-I-114 (13c) and C) AMJ-I-111 (14c). D) Superposition of 12b (gold), 13c (coral) and 14c (gray). The loop between Gln 189 and Gly 195 is colored cyan in the structure with 13c and magenta for 12b/14c.

4,4-Difluorocyclohexyl compounds. In previous studies related to norovirus 3CL protease inhibitors, the strategic introduction of a gem-dimethyl group into the inhibitor structure resulted in enhanced potency by restricting rotation around the nearby single bonds and lowering the entropic penalty associated with binding. Thus, we sought to capitalize on this by synthesizing gem-dimethyl-substituted compound 13c and, additionally, achieve the same end by introducing a stereocenter (compound 12c). The structures of 12b, 13c and 14c with SARS-CoV 3CLpro displayed well-defined electron density and the typically observed hydrogen bond interactions (FIG. 13). The 4,4-difluorocyclohexyl rings for all structures are positioned near the hydrophobic cleft in the $S_4$ subsite as shown in FIG. 14 A-C. Superposition of these structures revealed a nearly identical binding mode for 12b and 13c in which the 4,4-difluorocyclohexyl groups are positioned in the same region within the $S_4$ subsite (FIG. 14D). For 14c, the benzyl ring is oriented in a wide cleft formed by Asn 142 and Gln 189. However, the 4,4-difluorocyclohexyl ring of 13c contacts residues Thr 190 and Ala 191 (3.0-3.2 Å) and forms new hydrogen bond interactions with the backbone oxygen and nitrogen atoms respectively (FIG. 13E). This positions the 4,4-difluorocyclohexyl ring of 13c deeper into the $S_4$ pocket and results in a conformational change in the loop spanning Gln 189 to Gly 195 in order to accommodate the new interactions and avoid steric clash. However, it is not intuitively obvious why the $IC_{50}$ of 13c is ~4-fold higher than those of 12b and 14c.

Figure 15:
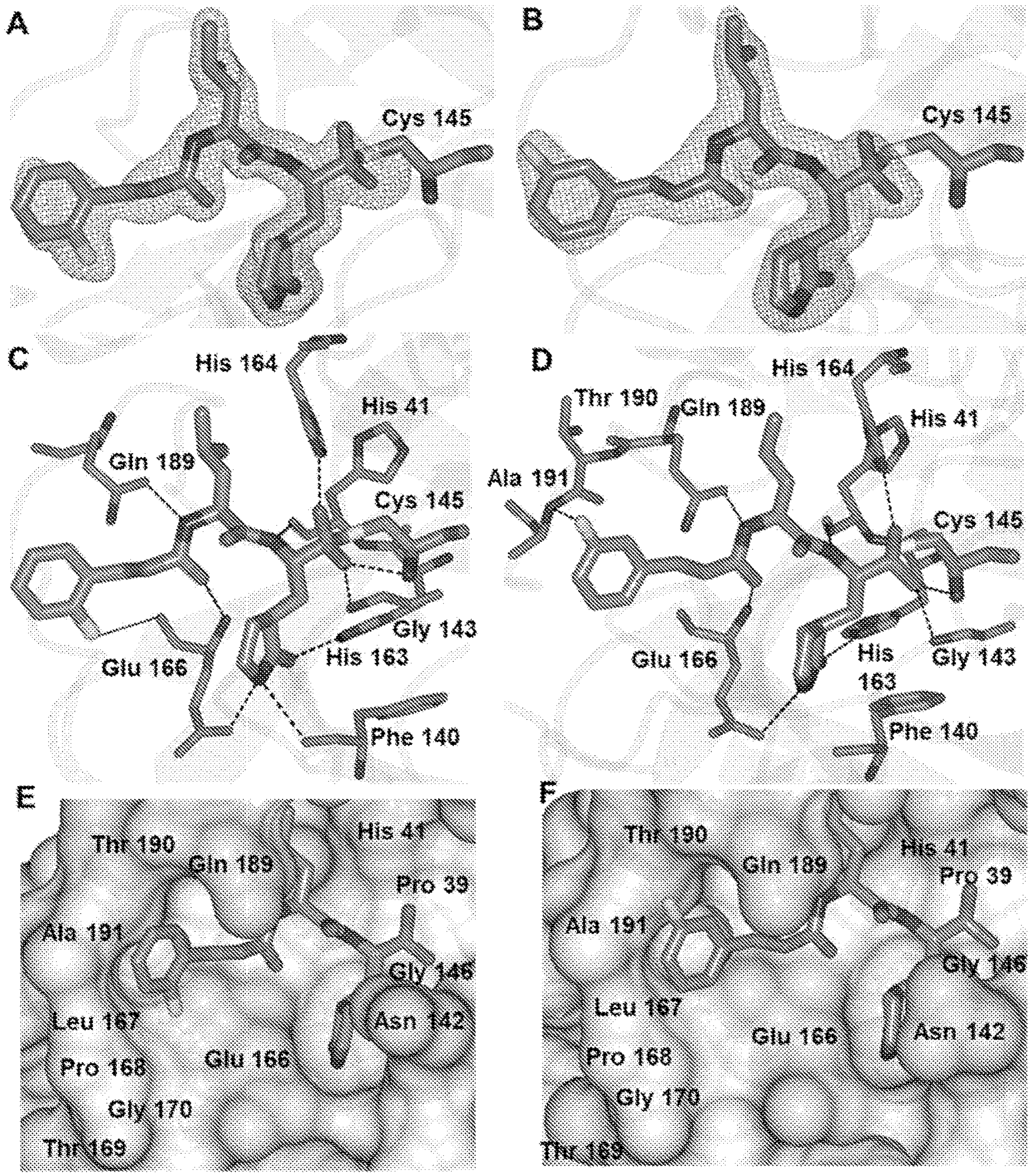
FIG. 15 shows the binding mode of inhibitors containing a fluorinated aromatic group. A/C) CSD-III-028 (17c), B/D) CSD-III-029 (18c) with SARS-CoV-2 3CLpro. $F_o$-$F_c$ Polder omit map (A-B) contoured at 3σ. Hydrogen bond interactions (C-D) are drawn as dashed lines. The 3.38 Å contact between the F-atom of 17c and the backbone O-atom of Glu 166 is drawn as a solid line in panel C. Surface representation showing the orientation of the 4,4-difluorocyclohexyl groups near the S4 subsite of SARS-CoV-2 3CLpro with neighboring residues colored yellow (nonpolar), cyan (polar), and white (weakly polar). E) CSD-III-028 (17c) and F) CSD-III-029 (18c).

Fluorinated Aryl Compounds. Positional analogue scanning is a widely used strategy for optimizing binding affinity, selectivity, and physicochemical properties of lead compounds containing aromatic or heteroaromatic rings. For instance, the introduction of fluorine (F-walk) or nitrogen (N-walk) is an effective means for multiparameter optimization by leveraging the beneficial impact of fluorine (or nitrogen) and minor structural changes. In an effort to determine the effect of fluorine on the binding mode in the $S_4$ subsite of GC376, the structures of the fluorinated benzyl compounds 17c, 18c, 19b, 20b (deuterated analog of 19b) and 21c were determined with SARS-CoV-2 3CLpro. The inhibitor o-fluorobenzyl (17c) and m-fluorobenzyl (18c) compounds displayed well-defined electron density and similar hydrogen bond interactions as shown in FIG. 15. Interestingly, the o-fluorobenzyl ring of 17c adopts a conformation in which the fluorine atom is directed away from Thr 190 and is instead positioned 3.38 Å from the backbone oxygen atom of Glu 166 (FIG. 15C). Conversely, the fluorine atom in 18c is positioned between Thr 190/Ala 191 in the $S_4$ pocket and is 3.10 Å from the backbone nitrogen atom of Ala 191 (FIG. 15D). The orientations of the fluorine atoms in 17c and 18c relative to the hydrophobic ridge in the $S_4$ pocket is shown in FIG. 15E-F.

Figure 17:
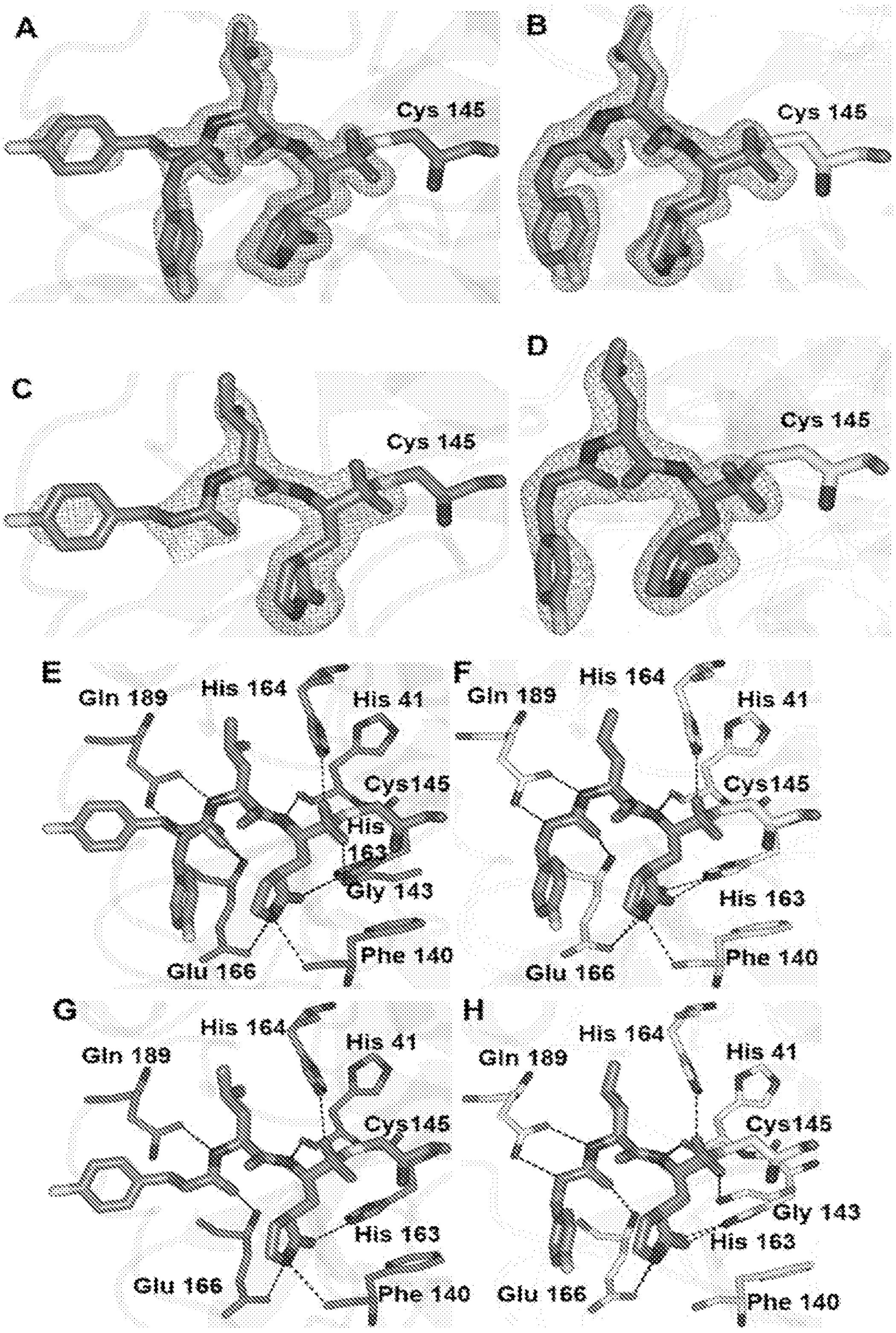
FIG. 17 shows the binding mode of CSD-III-008 (19b) (A and B) and CSD-III-009 (20b) (C and D) with SARS-CoV-2 3CLpro associated with subunit A (A/C) and subunit B (B/D). Electron density is a $F_o$-$F_c$ Polder omit map (green mesh) contoured at 3σ. Hydrogen bond interactions between SARS-CoV-2 3CLpro and CSD-III-008 (E and F) and CSD-III-009 (G and H) with associated with subunit A (E/F) and subunit B (G/H).
Figure 18:
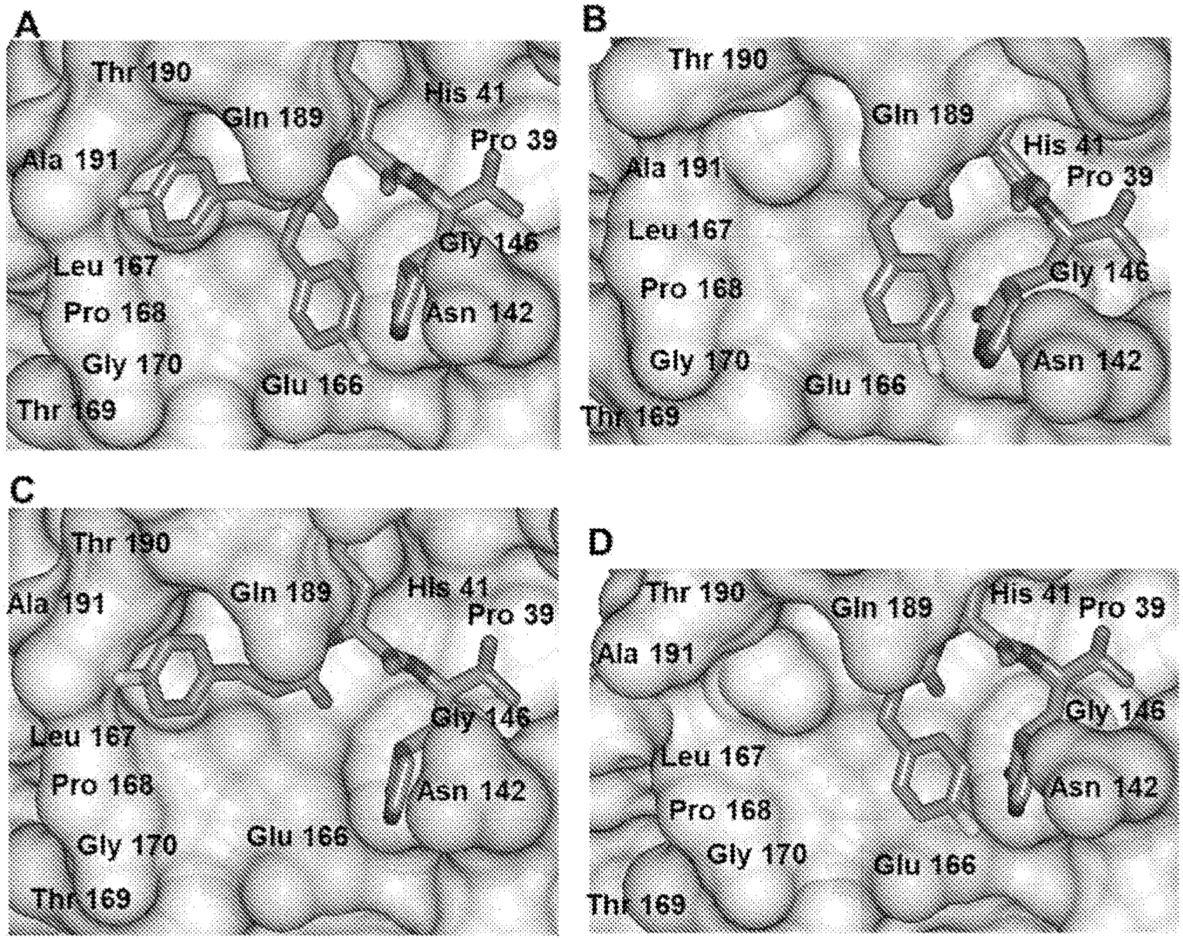
FIG. 18 shows the surface representation showing the orientation of CSD-III-008 (19b) (A and B) and CSD-III-009 (C and D) with associated with subunit A (A/C) and subunit B (B/D) on the SARS-CoV-2 3CLpro surface. Neighboring residues colored yellow (nonpolar), cyan (polar), and white (weakly polar).

The inhibitors that contain a p-fluorobenzyl group 19b and its deuterated analog 20b not surprisingly adopt very similar binding modes and hydrogen bond interactions as shown in FIGS. 17-18. Interestingly, the inhibitor adopts two conformations in which the p-fluorobenzyl ring is projected away from the $S_4$ subsite in subunit B and is positioned in the $S_4$ pocket in subunit A. However, the electron density for the p-fluorobenzyl ring is somewhat weaker in subunit A, which suggests that the pose in subunit B is likely the predominant conformation. This may be due to the fact that the fluorine atom does not form any contacts with polar atoms in the $S_4$ subsite and results in a conformation in which the aryl ring is positioned out of the pocket which is the same conformation observed for the parent compound GC376.

Figure 16:
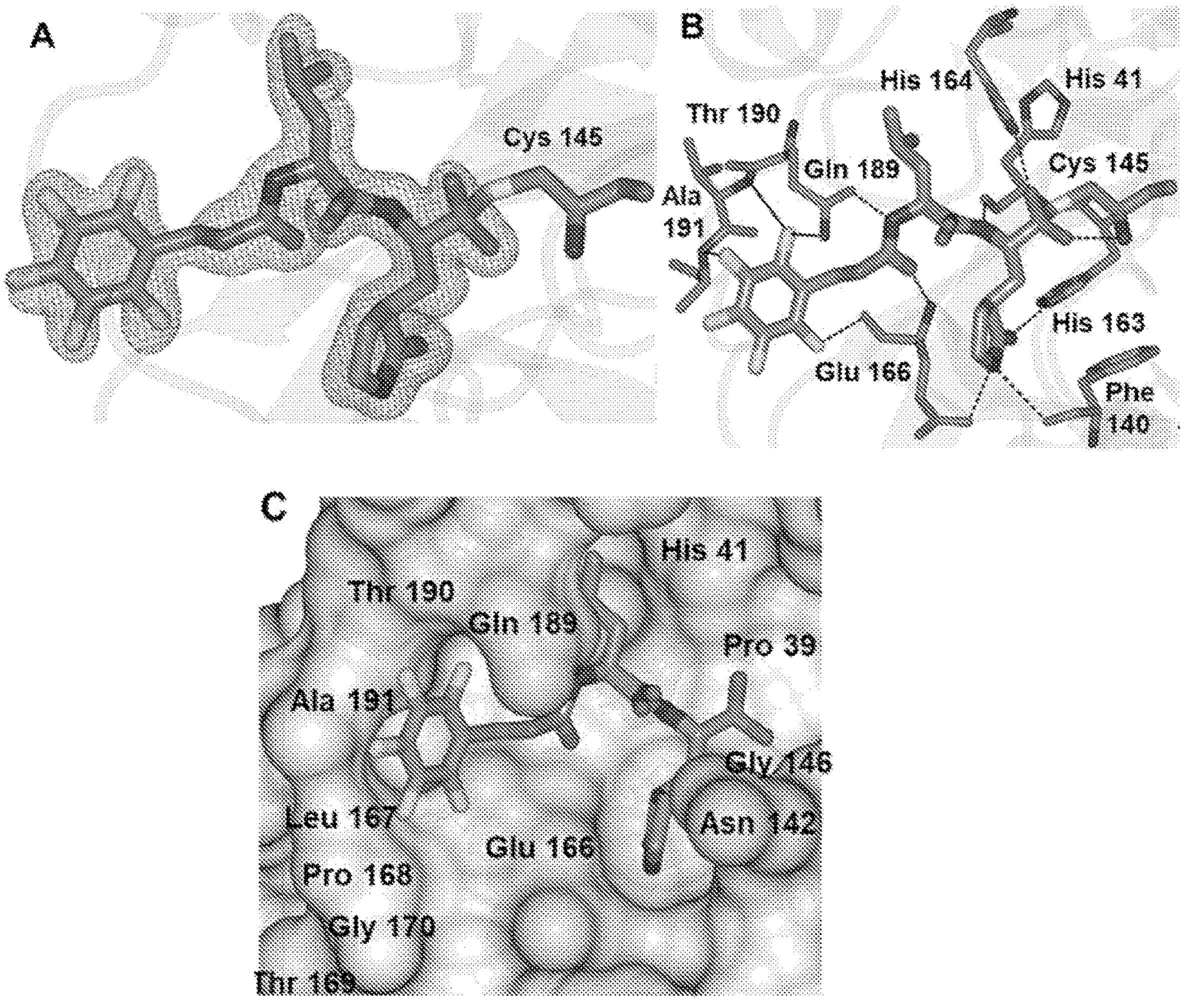
FIG. 16 shows the binding mode of NN-II-123 (21c) containing a perfluorinated aromatic group. A)$F_o$-$F_c$ Polder omit map contoured at 3σ. B) Hydrogen bond interactions are drawn as dashed lines. Close contacts to the perfluorinated ring that are longer than typical polar contact distances are drawn as solid lines. C) Surface representation showing the orientation of NN-II-123 (21c) near the S4 subsite of SARS-CoV-2 3CLpro with neighboring residues colored yellow (nonpolar), cyan (polar), and white (weakly polar).

The perfluorinated compound 21c also displayed well-defined difference electron density consistent with the aryl ring in one conformation (FIG. 16A). Interestingly, one of the o-fluorine atoms interacts with the backbone oxygen of Glu 166 (3.08 Å) which is shorter than that observed for 17c described above (3.38 Å). The other o-fluorine atom is positioned 2.92 Å from the backbone N-atom of Thr 190 and 3.12 Å from the side chain N-atom of Gln 189 (FIG. 16B). Similarly, the m-fluorine atom is positioned near the backbone nitrogen atom of Ala 191 (3.40 Å) which is longer than the distance observed for 18c (3.10 Å). The pentafluorobenzyl ring is positioned on top of the hydrophobic cleft within the $S_4$-subsite (FIG. 16C), unlike GC376 where the phenyl ring undergoes a hydrophobic collapse with the y-lactam ring and the inhibitor assumes a "paper clip" shape.

Finally, GC376 variants 23b/c and 24b/c were synthesized and screened as mixtures of epimers. The aldehyde and bisulfite adduct inhibitors 23b/c were found to potently inhibit 3CLpro ($IC_{50}$ 0.15 and 0.18 μM, respectively), and these were 27-fold and 19-fold more potent than the corresponding 24b/c aldehyde and bisulfite adducts, respectively. These findings provide tentative validation of the design regarding the use of a chiral center to attain directional control and augment binding interactions.

Conclusions

Effective management of SARS-CoV-2, the causative agent of the COVID-19 pandemic, requires not only the availability of safe and effective vaccines, but the availability of small-molecule therapeutics and prophylactics that target viral and host-based druggable targets. SARS-CoV-2 3CL protease is an attractive target for the development of COVID-19 therapeutics because of its vital role in viral replication. An array of approaches was utilized to enhance the potency and physicochemical parameters, including conformational and stereochemical control via the introduction of a gem-dimethyl group (Thorpe-Ingold effect) or stereocenter, deuteration, and fluorine, into the inhibitors. Virtually all inhibitors were found to display sub-micromolar potency and were devoid of cytotoxicity. Furthermore, several deuterated inhibitors which are likely to exhibit improved pharmacokinetics were found to be equipotent with the corresponding non-deuterated inhibitors. The fluorine-walk approach was applied to explore bioisosteric replacements for the phenyl ring in GC376 by replacing one or more hydrogen atoms. The effects of these modifications included unanticipated binding modes of the F-substituted phenyl ring and modestly-enhanced potency. The introduction of multiple fluorine atoms resulted in an orientation that allowed the fluorine atoms to engage in H-bonding with residues in the $S_4$ pocket, although with sub-optimal bond angles. High resolution cocrystal structures with an array of inhibitors unraveled the mechanism of action and provided valuable insights regarding the binding of the inhibitors to the active site and the identity of the structural determinants involved in binding. Collectively, the results of the studies described herein are significant and timely, and provide an effective launching pad for conducting further pre-clinical studies.

Experimental Section

General. Reagents and dry solvents were purchased from various chemical suppliers (Sigma-Aldrich, Acros Organics, Chem-Impex, TCI America, Oakwood chemical, APExBIO, Cambridge Isotopes, Alpha Aesar, Fisher and Advanced Chemblocks) and were used as obtained. Silica gel (230-450 mesh) used for flash chromatography was purchased from Sorbent Technologies (Atlanta, GA). Thin layer chromatography was performed using Analtech silica gel plates. Visualization was accomplished using UV light and/or iodine. NMR spectra were recorded in $CDCl_3$ or DMSO-$d_6$ using Varian XL-400 spectrometer. Melting points were recorded on a Mel-Temp apparatus and are uncorrected. High resolution mass spectrometry (HRMS) was performed at the Wichita State University Mass Spectrometry lab using Orbitrap Velos Pro mass spectrometer (ThermoFisher, Waltham, MA) equipped with an electrospray ion source. The purity of all final compounds was >95% as evidenced by NMR analysis.

Synthesis of Compounds

Preparation of compounds 1-5a, 9a, 17-22a. General procedure. To a solution of alcohol (1 eq) (Table 10) in anhydrous acetonitrile (10 mL/g alcohol) was added N,N'-disuccinimidyl carbonate (DSC) (1.2 eq) and TEA (3.0 eq) and the reaction mixture was stirred for 4h at room temperature. The solvent was removed in vacuo and the residue was dissolved in ethyl acetate (40 mL/g alcohol). The organic phase was washed with saturated aqueous $NaHCO_3$ (2×20 mL/g alcohol), followed by brine (20 mL/g alcohol). The organic layers were combined and dried over anhydrous $Na_2SO_4$, filtered and concentrated in vacuo to yield the mixed carbonate which was used in the next step without further purification.

To a solution of Leu-Gln surrogate amino alcohol (1.0 eq) in dry methylene chloride (10 mL/g of amino alcohol) was added TEA (1.5 eq) and the reaction mixture was stirred for 20 min at room temperature (solution 1). In a separate flask, the mixed carbonate was dissolved in dry methylene chloride (10 mL/g of carbonate) (solution 2). Solution 1 was added to solution 2 and the reaction mixture was stirred 3h at room temperature. Methylene chloride was added to the organic phase (40 mL/g of carbonate) and then washed with saturated aqueous $NaHCO_3$ (2×20 mL/g alcohol), followed by brine (20 mL/g alcohol). The organic phase was dried over anhydrous $Na_2SO_4$, filtered and concentrated in vacuo. The resultant crude product was purified by flash chromatography (hexane/ethyl acetate) to yield dipeptidyl alcohol a as a white solid. The reaction schemes are depicted in FIGS. 10A-10C.

TABLE 10

Alcohol Inputs

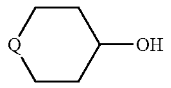

| Compound | Q |
|---|---|
| 1 | $C(CH_3)_2$ |
| 2 | —CH-iso-propyl (trans) |
| 3 | —CH-n-propyl (trans) |
| 4 | —CH-n-butyl (trans) |
| 5 | —CH-phenyl (trans) |

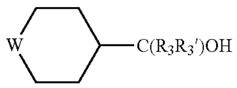

| Compound | W | $R_3$ | $R_3'$ |
|---|---|---|---|
| 6 (trans) | $—CHCF_3$ | H | H |
| 7 (cis) | $—CHCF_3$ | H | H |
| 8 | —CH-n-propyl | H | H |
| 9 | —CH-n-propyl | D | D |
| 10 | $—CF_2$ | H | H |
| 11 | $—CF_2$ | D | D |
| 12 | $—CF_2$ | $CH_3$ | H |
| 13 | $—CF_2$ | $CH_3$ | $CH_3$ |
| 14 | $—CF_2$ | benzyl | H |
| 15 | $—CF_2$ | phenyl | H |
| 16 | $—CF_2$ | n-butyl | H |

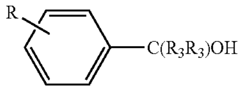

| Compound | R | $R_3$ | $R_3'$ |
|---|---|---|---|
| 17 | o-fluorine | H | H |
| 18 | m-fluorine | H | H |
| 19 | p-fluorine | H | H |
| 20 | p-fluorine | D | D |

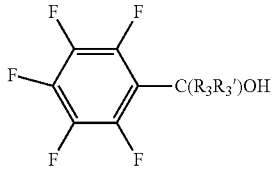

| Compound | $R_3$ | $R_3'$ |
|---|---|---|
| 21 | H | H |
| 22 | D | D |

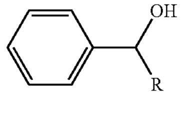

| Compound | R |
|---|---|
| 23 | n-propyl |
| 24 | benzyl |

4,4-Dimethylcyclohexyl ((S)-1-(((S)-1-hydroxy-3-((S)-2-oxopyrrolidin-3-yl)propan-2-yl)amino)-4-methyl-1-oxopentan-2-yl)carbamate (1a). Yield (36%), $^1H$ NMR (400 MHz, DMSO-$d_6$) δ 7.57 (d, J=8.9 Hz, 1H), 7.51 (s, 1H), 7.07 (d, J=8.3 Hz, 1H), 4.67-4.63 (m, 1H), 4.47-4.40 (m, 1H), 3.98-3.88 (m, 1H), 3.78-3.74 (m, 1H), 3.36-3.28 (m, 1H), 3.27-3.17 (m, 1H), 3.13 (t, J=8.9 Hz, 1H), 3.09-2.98 (m, 1H), 2.26-2.16 (m, 1H), 2.15-2.10 (m, 1H), 1.83-1.72 (m, 1H), 1.68-1.63 (m, 2H), 1.62-1.50 (m, 2H), 1.48-1.30 (m, 6H), 1.25-1.13 (m, 3H), 0.92-0.81 (m, 12H). (1r,4S)-4-iso-Propylcyclohexyl ((S)-1-(((S)-1-hydroxy-3-((S)-2-oxopyrrolidin-3-yl)propan-2-yl)amino)-4-methyl-1-oxopentan-2-yl)carbamate (2a). Yield (35%), $^1$H NMR (400 MHz, DMSO-$d_6$) δ 7.57 (d, J=8.9 Hz, 1H), 7.51 (s, 1H), 7.07 (d, J=8.2 Hz, 1H), 4.65 (t, J=5.5 Hz, 1H), 4.34 (td, J=11.0, 5.5 Hz, 1H), 3.97-3.88 (m, 1H), 3.79-3.74 (m, 1H), 3.38-3.28 (m, 1H), 3.27-3.18 (m, 1H), 3.14 (t, J=9.0 Hz, 1H), 3.05 (q, J=8.5 Hz, 1H), 2.29-2.20 (m, 1H), 2.18-2.07 (m, 1H), 1.91 (d, J=7.9 Hz, 2H), 1.84-1.72 (m, 1H), 1.71-1.66 (m, 2H), 1.62-1.50 (m, 2H), 1.48-1.30 (m, 4H), 1.26-1.13 (m, 2H), 1.01 (s, 3H), 0.93-0.80 (m, 12H).

(1s,4S)-4-propylcyclohexyl ((S)-1-(((S)-1-hydroxy-3-((S)-2-oxopyrrolidin-3-yl)propan-2-yl)amino)-4-methyl-1-oxopentan-2-yl)carbamate (3a). Yield (38%), $^1$H NMR (400 MHz, DMSO-$d_6$) δ 7.57 (d, J=9.0 Hz, 1H), 7.51 (s, 1H), 7.07 (d, J=8.2 Hz, 1H), 4.65 (s, 1H), 4.36 (td, J=11.0, 5.5 Hz, 1H), 3.98-3.88 (m, 1H), 3.78-3.74 (m, 1H), 3.36-3.29 (m, 1H), 3.28-3.18 (m, 1H), 3.14 (t, J=8.9 Hz, 1H), 3.10-2.99 (m, 1H), 2.30-2.19 (m, 1H), 2.17-2.07 (m, 1H), 1.93-1.84 (m, 2H), 1.77-1.67 (m, 3H), 1.62-1.48 (m, 2H), 1.48-1.30 (m, 3H), 1.33-1.21 (m, 3H), 1.21-1.08 (m, 4H), 0.97-0.90 (m, 2H), 0.90-0.81 (m, 9H).

(1s,4S)-4-butylcyclohexyl ((S)-1-(((S)-1-hydroxy-3-((S)-2-oxopyrrolidin-3-yl)propan-2-yl)amino)-4-methyl-1-oxopentan-2-yl)carbamate (4a). Yield (35%), $^1$H NMR (400 MHz, DMSO-$d_6$) δ 7.57 (d, J=9.0 Hz, 1H), 7.51 (s, 1H), 7.07 (d, J=8.2 Hz, 1H), 4.65 (t, J=5.5 Hz, 1H), 4.36 (tt, J=10.9, 4.2 Hz, 1H), 3.98-3.88 (m, 1H), 3.79-3.74 (m, 1H), 3.38-3.28 (m, 1H), 3.28-3.18 (m, 1H), 3.14 (t, J=8.9 Hz, 1H), 3.10-2.99 (m, 1H), 2.30-2.18 (m, 1H), 2.18-2.07 (m, 1H), 1.93-1.84 (m, 2H), 1.79-1.65 (m, 3H), 1.62-1.50 (m, 2H), 1.48-1.30 (m, 3H), 1.29-1.14 (m, 9H), 0.97-0.90 (m, 2H), 0.90-0.81 (m, 9H).

(1r,4S)-4-phenylcyclohexyl ((S)-1-(((S)-1-hydroxy-3-((S)-2-oxopyrrolidin-3-yl)propan-2-yl)amino)-4-methyl-1-oxopentan-2-yl)carbamate (5a). Yield (51%), $^1$H NMR (400 MHz, DMSO-$d_6$) δ 7.59 (d, J=9.0 Hz, 1H), 7.51 (s, 1H), 7.32-7.10 (m, 6H), 4.66 (t, J=5.5 Hz, 1H), 4.52 (ddd, J=15.2, 10.8, 4.3 Hz, 1H), 3.99-3.90 (m, 1H), 3.80-3.75 (m, 1H), 3.41-3.28 (m, 1H), 3.28-3.18 (m, 1H), 3.14 (t, J=8.9 Hz, 1H), 3.10-3.00 (m, 1H), 2.29-2.20 (m, 1H), 2.20-2.09 (m, 1H), 2.03-1.98 (m, 3H), 1.81 (d, J=13.0 Hz, 3H), 1.69-1.50 (m, 4H), 1.49-1.31 (m, 5H), 0.86 (dd, J=8.8, 6.5 Hz, 6H).

(4-(Trifluoromethyl) cyclohexyl) methyl ((2S)-1-(((2S)-1-hydroxy-3-(2-oxopyrrolidin-3-yl) propan-2-yl) amino)-4-methyl-1-oxopentan-2-yl) carbamate (6a). Yield (83%). $^1$H NMR (400 MHz, DMSO-$d_6$) δ 7.60 (d, J=8.9 Hz, 1H), 7.52 (s, 1H), 7.16 (d, J=8.3 Hz, 1H), 4.66 (s, 1H), 3.99-3.89 (m, 1H), 3.83-3.71 (m, 2H), 3.27-3.19 (m, 2H), 3.15 (t, 2H), 3.10-3.02 (m, 1H), 2.26-2.08 (m, 3H), 1.91-1.73 (m, 4H), 1.64-1.52 (m, 4H), 1.49-1.31 (m, 1H), 1.30-1.15 (m, 1H), 1.08-0.94 (m, 4H), 0.90-0.81 (m, 6H).

((1r,4S)-4-(Trifluoromethyl) cyclohexyl) methyl ((2S)-1-(((2S)-1-hydroxy-3-(2-oxopyrrolidin-3-yl) propan-2-yl) amino)-4-methyl-1-oxopentan-2-yl) carbamate (7a). Yield (80%).

$^1$H NMR (400 MHz, DMSO-$d_6$) δ 7.61 (d, J=9.0 Hz, 1H), 7.53 (s, 1H), 7.19 (d, J=8.2 Hz, 1H), 4.67 (s, 2H), 4.07-3.86 (m, 2H), 3.76 (s, 1H), 3.26-3.18 (m, 1H), 3.17-3.11 (m, 2H), 3.09-3.01 (m, 2H), 2.33-2.19 (m, 3H), 2.18-2.09 (m, 1H), 1.89-1.85 (m, 2H), 1.84-1.72 (m, 2H), 1.64-1.32 (m, 9H), 0.90-0.81 (m, 6H).

((1r,4R)-4-propylcyclohexyl) methyl ((2S)-1-(((2S)-1-hydroxy-3-(2-oxopyrrolidin-3-yl) propan-2-yl) amino)-4-methyl-1-oxopentan-2-yl) carbamate (8a). Yield (86%). $^1$H NMR (400 MHz, DMSO-$d_6$) δ 7.62-7.57 (m, 1H), 7.52 (s, 1H), 7.12 (d, J=8.3 Hz, 1H), 4.65 (s, 1H), 3.99-3.89 (m, 1H), 3.82-3.68 (m, 3H), 3.37-3.19 (m, 2H), 3.18-3.02 (m, 2H), 2.26-2.07 (m, 4H), 1.76-1.65 (m, 4H), 1.62-1.51 (m, 8H), 1.49-1.32 (m, 2H), 1.32-1.24 (m, 2H), 1.21-1.10 (m, 2H), 0.99-0.78 (m, 9H).

((1s,4S)-4-propylcyclohexyl) methyl-d2 ((2S)-1-(((2S)-1-hydroxy-3-(2-oxopyrrolidin-3-yl) propan-2-yl) amino)-4-methyl-1-oxopentan-2-yl) carbamate (9a). Yield (43%). $^1$H NMR (400 MHz, DMSO-$d_6$) δ 7.59 (d, J=8.9 Hz, 1H), 7.52 (s, 1H), 7.12 (d, J=8.3 Hz, 1H), 4.65 (s, 1H), 3.98-3.89 (m, 1H), 3.80-3.70 (m, 1H), 3.27-3.10 (m, 2H), 3.10-3.00 (m, 2H), 2.28-2.06 (m, 4H), 1.70 (s, 4H), 1.63-1.51 (m, 2H), 1.49-1.34 (m, 8H), 1.32-1.23 (m, 2H), 1.20-1.10 (m, 2H), 0.90-0.81 (m, 9H).

(4,4-Difluorocyclohexyl)methyl ((S)-1-(((S)-1-hydroxy-3-((S)-2-oxopyrrolidin-3-yl)propan-2-yl)amino)-4-methyl-1-oxopentan-2-yl)carbamate (10a). Yield (90%). $^1$H NMR (400 MHz, DMSO-$d_6$) δ 7.60 (d, J=8.9 Hz, 1H), 7.52 (s, 1H), 7.20 (d, J=8.3 Hz, 1H), 4.66 (s, 1H), 3.95 (td, J=8.9, 5.4 Hz, 1H), 3.90-3.69 (m, 3H), 3.23 (d, J=5.7 Hz, 1H), 3.18-3.00 (m, 2H), 2.28-2.07 (m, 2H), 2.06-1.93 (m, 2H), 1.90-1.64 (m, 6H), 1.56 (dq, J=11.9, 8.8 Hz, 2H), 1.51-1.30 (m, 3H), 1.30-1.12 (m, 2H), 0.86 (dd, J=10.5, 6.6 Hz, 6H).

(4,4-Difluorocyclohexyl) methyl-d2 ((2S)-1-(((2S)-1-hydroxy-3-(2-oxopyrrolidin-3-yl) propan-2-yl) amino)-4-methyl-1-oxopentan-2-yl) carbamate (1a). Yield (81%). $^1$H NMR (400 MHz, DMSO-$d_6$) δ 7.60 (d, J=8.9 Hz, 1H), 7.52 (s, 1H), 7.20 (d, J=8.2 Hz, 1H), 3.99-3.90 (m, 1H), 3.77 (s, 1H), 3.37-3.19 (m, 2H), 3.18-3.00 (m, 2H), 2.27-2.07 (m, 2H), 2.03-1.94 (m, 2H), 1.87-1.63 (m, 6H), 1.63-1.49 (m, 2H), 1.47-1.29 (m, 3H), 1.29-1.13 (m, 2H), 0.90-0.81 (m, 6H).

1-(4,4-Difluorocyclohexyl)ethyl ((S)-1-(((S)-1-hydroxy-3-((S)-2-oxopyrrolidin-3-yl)propan-2-yl)amino)-4-methyl-1-oxopentan-2-yl)carbamate (12a). Yield (76%). $^1$H NMR (400 MHz, DMSO-$d_6$) δ 7.61-7.50 (m, 2H), 7.11 (d, J=8.2 Hz, 1H), 4.66 (t, J=5.3 Hz, 1H), 4.59-4.50 (m, 1H), 3.98-3.90 (m, 1H), 3.79-3.75 (m, 1H), 3.39-3.29 (m, 1H), 3.28-3.18 (m, 1H), 3.18-3.10 (m, 1H), 3.10-2.99 (m, 1H), 2.27-2.18 (m, 1H), 2.16-2.09 (m, 1H), 2.02-1.97 (m, 2H), 1.83-1.63 (m, 5H), 1.63-1.51 (m, 3H), 1.47-1.31 (m, 3H), 1.27-1.22 (m, 2H), 1.12 (dd, 2H), 0.90-0.81 (m, 6H).

2-(4,4-Difluorocyclohexyl)propan-2-yl ((S)-1-(((S)-1-hydroxy-3-((S)-2-oxopyrrolidin-3-yl)propan-2-yl)amino)-4-methyl-1-oxopentan-2-yl)carbamate (13a). Yield (72%). $^1$H NMR (400 MHz, $DMSO_6$) δ 7.59-7.47 (m, 2H), 6.94 (d, J=8.2 Hz, 1H), 4.66 (t, J=5.5 Hz, 1H), 3.93-3.83 (m, 1H), 3.79-3.75 (m, 1H), 3.42-3.29 (m, 1H), 3.27-3.18 (m, 1H), 3.14 (t, J=8.9 Hz, 1H), 3.10-2.99 (m, 1H), 2.27-2.09 (m, 2H), 2.06-1.91 (m, 3H), 1.85-1.61 (m, 5H), 1.61-1.51 (m, 2H), 1.46-1.34 (m, 3H), 1.33 (s, 6H), 1.31-1.18 (m, 2H), 0.90-0.81 (m, 6H).

1-(4,4-Difluorocyclohexyl)-2-phenylethyl ((S)-1-(((S)-1-hydroxy-3-((S)-2-oxopyrrolidin-3-yl)propan-2-yl)amino)-4-methyl-1-oxopentan-2-yl)carbamate (14a). Yield (79%). $^1$H NMR (400 MHz, DMSO-$d_6$) δ 7.61-7.54 (m, 1H), 7.52 (s, 1H), 7.11 (d, J=8.2 Hz, 1H), 4.66 (t, J=5.3 Hz, 1H), 4.59-4.50 (m, 1H), 3.98-3.90 (m, 1H), 3.79-3.75 (m, 1H), 3.39-3.29 (m, 1H), 3.28-3.18 (m, 1H), 3.18-3.10 (m, 1H), 3.10-2.99 (m, 1H), 2.27-2.18 (m, 1H), 2.16-2.09 (m, 1H), 2.02-1.97 (m, 2H), 1.83-1.63 (m, 5H), 1.63-1.51 (m, 3H), 1.47-1.31 (m, 3H), 1.27-1.22 (m, 2H), 1.12 (dd, 3H), 0.90-0.81 (m, 6H).

(4,4-Difluorocyclohexyl)(phenyl)methyl ((S)-1-(((S)-1-hydroxy-3-((S)-2-oxopyrrolidin-3-yl)propan-2-yl)amino)-4-methyl-1-oxopentan-2-yl)carbamate (15a). Yield (86%). $^1$H NMR (400 MHz, DMSO-$d_6$) δ 7.64-7.50 (m, 2H), 7.39-7.23 (m, 6H), 4.68-4.64 (m, 1H), 4.00-3.89 (m, 1H), 3.87-3.73 (m, 2H), 3.39-3.29 (m, 1H), 3.27-3.20 (m, 1H), 3.19-3.10 (m, 1H), 3.10-3.02 (m, 1H), 2.25-2.09 (m, 2H), 2.06-1.92 (m, 2H), 1.87-1.66 (m, 5H), 1.65-1.51 (m, 2H), 1.49-1.32 (m, 4H), 1.32-1.18 (m, 2H), 0.93-0.71 (m, 6H).

1-(4,4-Difluorocyclohexyl)pentyl ((S)-1-(((S)-1-hydroxy-3-((S)-2-oxopyrrolidin-3-yl)propan-2-yl)amino)-4-methyl-1-oxopentan-2-yl)carbamate (16a). Yield (91%). $^1$H NMR (400 MHz, DMSO-$d_6$) δ 7.60 (d, J=9.0 Hz, 1H), 7.52 (s, 1H), 7.20 (d, J=8.3 Hz, 1H), 4.66 (t, J=5.6 Hz, 1H), 4.00-3.90 (m, 1H), 3.90-3.77 (m, 1H), 3.77-3.74 (m, 1H), 3.40-3.31 (m, 1H), 3.29-3.19 (m, 1H), 3.14 (t, J=9.0 Hz, 1H), 3.11-3.00 (m, 1H), 2.25-2.15 (m, 1H), 2.15-2.09 (m, 1H), 2.02-1.97 (m, 3H), 1.88-1.80 (m, 1H), 1.79-1.65 (m, 8H), 1.63-1.51 (m, 2H), 1.49-1.31 (m, 4H), 1.26-1.18 (m, 3H), 0.93-0.81 (m, 9H).

2-Fluorobenzyl ((S)-1-(((S)-1-hydroxy-3-((S)-2-oxopyrrolidin-3-yl)propan-2-yl)amino)-4-methyl-1-oxopentan-2-yl)carbamate (17a). Yield (33%). $^1$H NMR (400 MHz, $CDCl_3$) δ 7.76 (d, J=7.2 Hz, 1H), 7.42-7.34 (m, 1H), 7.34-7.27 (m, 1H), 7.12 (td, J=7.5, 1.2 Hz, 1H), 7.09-7.00 (m, 1H), 6.23 (s, 1H), 5.56 (d, J=8.3 Hz, 1H), 5.19-5.14 (m, 2H), 4.27-4.22 (m, 1H), 4.01-3.96 (m, 1H), 3.77-3.46 (m, 2H), 3.37-3.24 (m, 2H), 2.46-2.33 (m, 2H), 2.11-1.87 (m, 2H), 1.85-1.74 (m, 1H), 1.74-1.58 (m, 2H), 1.57-1.46 (m, 1H), 0.94 (d, J=5.8 Hz, 6H).

3-Fluorobenzyl ((S)-1-(((S)-1-hydroxy-3-((S)-2-oxopyrrolidin-3-yl)propan-2-yl)amino)-4-methyl-1-oxopentan-2-yl)carbamate (18a). Yield (41%). $^1$H NMR (400 MHz, $CDCl_3$) δ 7.82 (d, J=7.2 Hz, 1H), 7.35-7.28 (m, 1H), 7.12-7.02 (m, 2H), 7.02-6.94 (m, 1H), 6.41 (s, 1H), 5.70 (d, J=8.3 Hz, 1H), 5.16-5.00 (m, 2H), 4.29-4.22 (m, 1H), 4.02-3.93 (m, 1H), 3.74-3.53 (m, 2H), 3.36-3.22 (m, 2H), 2.45-2.30 (m, 2H), 2.07-1.95 (m, 1H), 1.79 (td, J=9.4, 2.8 Hz, 1H), 1.73-1.43 (m, 4H), 0.94 (d, J=6.1 Hz, 6H).

4-Fluorobenzyl ((S)-1-(((S)-1-hydroxy-3-((S)-2-oxopyrrolidin-3-yl)propan-2-yl)amino)-4-methyl-1-oxopentan-2-yl)carbamate (19a). Yield (37%). $^1$H NMR (400 MHz, $CDCl_3$) δ 7.73 (d, J=7.4 Hz, 1H), 7.37-7.28 (m, 2H), 7.08-6.97 (m, 2H), 6.37 (s, 1H), 5.56 (d, J=8.1 Hz, 1H), 5.12-5.02 (m, 2H), 4.31-4.13 (m, 1H), 4.05-3.90 (m, 1H), 3.66-3.53 (m, 2H), 3.39-3.25 (m, 2H), 2.46-2.31 (m, 2H), 2.05-1.93 (m, 1H), 1.88-1.76 (m, 1H), 1.74-1.57 (m, 3H), 1.57-1.45 (m, 1H), 0.93 (d, J=6.1 Hz, 6H).

(4-Fluorophenyl)methyl-d2 ((S)-1-(((S)-1-hydroxy-3-((S)-2-oxopyrrolidin-3-yl)propan-2-yl)amino)-4-methyl-1-oxopentan-2-yl)carbamate (20a). Yield (37%). $^1$H NMR (400 MHz, $CDCl_3$) δ 7.76 (d, J=7.3 Hz, 1H), 7.36-7.29 (m, 2H), 7.07-6.98 (m, 2H), 6.32 (s, 1H), 5.55 (d, J=8.3 Hz, 1H), 4.27-4.20 (m, 1H), 4.00-3.96 (m, 1H), 3.66-3.53 (m, 2H), 3.37-3.23 (m, 2H), 2.48-2.32 (m, 2H), 2.03-1.93 (m, 1H), 1.87-1.76 (m, 1H), 1.73-1.57 (m, 3H), 1.55-1.45 (m, 1H), 0.93 (d, J=6.1 Hz, 6H).

(Perfluorophenyl)methyl ((2S)-1-(((2S)-1-hydroxy-3-(2-oxopyrrolidin-3-yl) propan-2-yl) amino)-4-methyl-1-oxopentan-2-yl) carbamate (21a). Yield (21%). $^1$H NMR (400 MHz, DMSO-$d_6$) δ 7.66 (d, J=8.9 Hz, 1H), 7.52 (s, 1H), 7.46 (d, J=8.0 Hz, 1H), 5.18-5.07 (m, 2H), 4.64 (s, 1H), 3.99-3.90 (m, 1H), 3.75 (s, 1H), 3.25-3.02 (m, 4H), 2.27-2.16 (m, 1H), 2.15-2.05 (m, 2H), 1.81-1.71 (m, 1H), 1.62-1.50 (m, 2H), 1.47-1.31 (m, 2H), 0.90-0.78 (m, 6H).

(Perfluorophenyl)methyl-d2 ((2S)-1-(((2S)-1-hydroxy-3-(2-oxopyrrolidin-3-yl) propan-2-yl) amino)-4-methyl-1-oxopentan-2-yl) carbamate (22a). Yield (11%). $^1$H NMR (400 MHz, DMSO-$d_6$) δ 7.65 (d, J=8.9 Hz, 1H), 7.52 (s, 1H), 7.46 (d, J=8.0 Hz, 1H), 4.64 (s, 1H), 3.99-3.90 (m, 1H), 3.75 (s, 1H), 3.25-3.02 (m, 4H), 2.26-2.16 (m, 1H), 2.15-2.05 (m, 2H), 1.81-1.71 (m, 1H), 1.60-1.49 (m, 2H), 1.46-1.31 (m, 2H), 0.90-0.77 (m, 6H).

1-Phenylbutyl ((S)-1-(((S)-1-hydroxy-3-((S)-2-oxopyrrolidin-3-yl)propan-2-yl)amino)-4-methyl-1-oxopentan-2-yl) carbamate (23a). Yield (60%). $^1$H NMR (400 MHz, $CDCl_3$) δ 7.59 (dd, J=79.1, 7.3 Hz, 1H), 7.36-7.21 (m, 5H), 6.24 (d, J=37.3 Hz, 1H), 5.60 (t, J=7.1, 7.1 Hz, 1H), 5.41 (dd, J=23.4, 8.0 Hz, 1H), 4.21-4.11 (m, 1H), 4.04-3.89 (m, 1H), 3.69-3.47 (m, 2H), 3.36-3.19 (m, 2H), 2.53-2.17 (m, 2H), 2.03-1.80 (m, 3H), 1.79-1.42 (m, 3H), 1.41-1.21 (m, 2H), 0.98-0.83 (m, 11H).

1,2-Diphenylethyl ((S)-1-(((S)-1-hydroxy-3-((S)-2-oxopyrrolidin-3-yl)propan-2-yl)amino)-4-methyl-1-oxopentan-2-yl)carbamate (24a). Yield (83%). $^1$H NMR (400 MHz, $CDCl_3$) δ 7.58 (dd, J=49.0, 7.4 Hz, 1H), 7.33-7.16 (m, 8H), 7.11-7.02 (m, 2H), 6.09 (d, J=26.6 Hz, 1H), 5.88-5.75 (m, 1H), 5.42-5.32 (m, 1H), 4.17-4.07 (m, 1H), 4.04-3.87 (m, 1H), 3.68-3.43 (m, 2H), 3.33-2.98 (m, 4H), 2.52-2.21 (m, 2H), 2.02-1.39 (m, 6H), 0.94-0.79 (m, 6H).

Preparation of compounds 1-24b. General procedure. To a solution of dipeptidyl alcohol a (1 eq) in anhydrous dichloromethane (300 mL/g dipeptidyl alcohol) kept at 0-5° C. under a $N_2$ atmosphere was added Dess-Martin periodinane reagent (3.0 eq) and the reaction mixture was stirred for 3 h at 15-20° C. The organic phase was washed with 10% aq $Na_2S_2O_3$ (2×100 mL/g dipeptidyl alcohol), followed by saturated aqueous $NaHCO_3$ (2×100 mL/g dipeptidyl alcohol), distilled water (2×100 mL/g dipeptidyl alcohol), and brine (100 mL/g dipeptidyl alcohol). The organic phase was dried over anhydrous $Na_2SO_4$, filtered and concentrated in vacuo. The resulting crude product was purified by flash chromatography (hexane/ethyl acetate) to yield aldehyde b as a white solid. The general reaction scheme is illustrated in FIG. 10B.

4,4-Dimethylcyclohexyl ((S)-4-methyl-1-oxo-1-(((S)-1-oxo-3-((S)-2-oxopyrrolidin-3-yl)propan-2-yl)amino)pentan-2-yl)carbamate (1b). Yield (80%). $^1$H NMR (400 MHz, DMSO-$d_6$) δ 9.40 (s, 1H), 8.39 (d, J=7.7 Hz, 1H), 7.62 (s, 1H), 7.19 (d, J=8.0 Hz, 1H), 4.49-4.40 (m, 1H), 4.24-4.14 (m, 1H), 4.07-3.97 (m, 1H), 3.16 (t, J=9.2 Hz, 1H), 3.12-3.00 (m, 1H), 2.31-2.22 (m, 1H), 2.19-2.09 (m, 1H), 1.95-1.83 (m, 1H), 1.74-1.55 (m, 5H), 1.54-1.31 (m, 6H), 1.25-1.15 (m, 2H), 0.92-0.81 (m, 12H).

(1r,4S)-4-isopropylcyclohexyl ((S)-4-methyl-1-oxo-1-(((S)-1-oxo-3-((S)-2-oxopyrrolidin-3-yl)propan-2-yl) amino)pentan-2-yl)carbamate (2b). Yield (78%). $^1$H NMR (400 MHz, DMSO-$d_6$) δ 9.40 (s, 1H), 8.40 (d, J=7.6 Hz, 1H), 7.63 (s, 1H), 7.19 (d, J=8.0 Hz, 1H), 4.42-4.30 (m, 1H), 4.19 (ddd, J=11.4, 7.6, 4.2 Hz, 1H), 4.07-3.96 (m, 1H), 3.28-3.01 (m, 2H), 2.35-2.19 (m, 1H), 2.19-2.08 (m, 1H), 1.95-1.84 (m, 3H), 1.73-1.57 (m, 5H), 1.53-1.36 (m, 3H), 1.27-1.20 (m, 2H), 1.02 (s, 3H), 0.97-0.80 (m, 12H).

(1s,4S)-4-propylcyclohexyl ((S)-4-methyl-1-oxo-1-(((S)-1-oxo-3-((S)-2-oxopyrrolidin-3-yl)propan-2-yl)amino)pentan-2-yl)carbamate (3b). Yield (73%). $^1$H NMR (400 MHz, DMSO-$d_6$) δ 9.40 (s, 1H), 8.40 (d, J=7.7 Hz, 1H), 7.63 (s, 1H), 7.19 (d, J=7.9 Hz, 1H), 4.37 (td, J=11.0, 5.5 Hz, 1H), 4.24-4.12 (m, 1H), 4.07-3.97 (m, 1H), 3.21-3.01 (m, 2H), 2.35-2.22 (m, 1H), 2.19-2.08 (m, 1H), 1.95-1.85 (m, 3H), 1.76-1.55 (m, 5H), 1.54-1.37 (m, 2H), 1.35-1.19 (m, 4H), 1.19-1.09 (m, 3H), 1.01-0.91 (m, 2H), 0.91-0.81 (m, 9H).

(1s,4S)-4-Butylcyclohexyl ((S)-4-methyl-1-oxo-1-(((S)-1-oxo-3-((S)-2-oxopyrrolidin-3-yl)propan-2-yl)amino)pentan-2-yl)carbamate (4b). Yield (65%). $^1$H NMR (400 MHz, DMSO-$d_6$) δ 9.40 (s, 1H), 8.40 (d, J=7.6 Hz, 1H), 7.63 (s, 1H), 7.19 (d, J=7.9 Hz, 1H), 4.37 (td, J=11.0, 5.3 Hz, 1H), 4.19 (ddd, J=11.5, 7.7, 4.1 Hz, 1H), 4.02 (q, J=8.5 Hz, 1H), 3.17 (t, J=9.1 Hz, 1H), 3.13-3.01 (m, 1H), 2.32-2.23 (m, 1H), 2.20-2.08 (m, 1H), 1.96-1.84 (m, 3H), 1.76-1.72 (m, 3H), 1.72-1.55 (m, 3H), 1.53-1.37 (m, 2H), 1.29-1.13 (m, 8H), 1.01-0.91 (m, 2H), 0.91-0.80 (m, 9H). (1r,4S)-4-Phenylcyclohexyl ((S)-4-methyl-1-oxo-1-(((S)-1-oxo-3-((S)-2-oxopyrrolidin-3-yl)propan-2-yl)amino)pentan-2-yl)carbamate (5b). Yield (63%). $^1$H NMR (400 MHz, DMSO-$d_6$) δ 9.41 (s, 1H), 8.43 (d, J=7.7 Hz, 1H), 7.63 (s, 1H), 7.32-7.10 (m, 6H), 4.53 (td, J=10.9, 5.4 Hz, 1H), 4.20 (ddd, J=11.4, 7.5, 4.0 Hz, 1H), 4.07-3.92 (m, 1H), 3.29-3.02 (m, 2H), 2.36-2.23 (m, 1H), 2.21-2.10 (m, 1H), 2.07-1.96 (m, 2H), 1.96-1.85 (m, 1H), 1.81 (d, J=12.8 Hz, 2H), 1.70-1.56 (m, 6H), 1.56-1.42 (m, 4H), 0.89 (dd, J=9.5, 6.6 Hz, 6H).

(4-(Trifluoromethyl) cyclohexyl) methyl ((2S)-4-methyl-1-oxo-1-(((2S)-1-oxo-3-(2-oxopyrrolidin-3-yl) propan-2-yl) amino) pentan-2-yl) carbamate (6b). Yield (88%). $^1$H NMR (400 MHz, DMSO-$d_6$) δ 9.40 (s, 1H), 8.43 (d, J=7.6 Hz, 1H), 7.63 (s, 1H), 7.29 (d, J=8.0 Hz, 1H), 4.22-4.15 (m, 1H), 4.07-3.99 (m, 1H), 3.78 (d, J=2.0 Hz, 2H), 3.20-3.05 (m, 3H), 2.31-2.08 (m, 3H), 1.95-1.76 (m, 4H), 1.70-1.40 (m, 5H), 1.29-1.16 (m, 1H), 1.02 (q, J=13.0 Hz, 4H), 0.92-0.81 (m, 6H).

((1r,4S)-4-(Trifluoromethyl) cyclohexyl) methyl ((2S)-4-methyl-1-oxo-1-(((2S)-1-oxo-3-(2-oxopyrrolidin-3-yl) propan-2-yl) amino) pentan-2-yl) carbamate (7b). Yield (91%). $^1$H NMR (400 MHz, DMSO-$d_6$) δ 9.40 (s, 1H), 8.43 (d, J=7.6 Hz, 1H), 7.63 (s, 1H), 7.31 (d, J=8.0 Hz, 1H), 4.24-4.14 (m, 1H), 4.08-3.99 (m, 1H), 3.98-3.92 (m, 2H), 3.21-3.04 (m, 3H), 2.33-2.20 (m, 3H), 2.19-2.08 (m, 1H), 1.92-1.83 (m, 4H), 1.69-1.38 (m, 9H), 0.92-0.81 (m, 6H).

((1r,4R)-4-Propylcyclohexyl) methyl ((2S)-4-methyl-1-oxo-1-(((2S)-1-oxo-3-(2-oxopyrrolidin-3-yl) propan-2-yl) amino) pentan-2-yl) carbamate (8b). Yield (42%). $^1$H NMR (400 MHz, DMSO-$_6$) δ 9.40 (s, 1H), 8.42 (d, J=7.7 Hz, 1H), 7.63 (s, 1H), 7.25 (d, J=8.0 Hz, 1H), 4.22-4.15 (m, 1H), 4.05-4.01 (m, 1H), 3.78-3.74 (m, 2H), 3.20-3.05 (m, 2H), 2.19-2.10 (m, 3H), 1.94-1.85 (m, 3H), 1.75-1.60 (m, 10H), 1.54-1.40 (m, 2H), 1.33-1.23 (m, 2H), 1.17-1.10 (m, 2H), 0.97-0.81 (m, 9H).

((1s,4S)-4-Propylcyclohexyl) methyl-d2 ((2S)-4-methyl-1-oxo-1-(((2S)-1-oxo-3-(2-oxopyrrolidin-3-yl) propan-2-yl) amino) pentan-2-yl) carbamate (9b). Yield (96%). $^1$H NMR (400 MHz, DMSO-$d_6$) δ 9.40 (s, 1H), 8.42 (d, J=7.6 Hz, 1H), 7.63 (s, 1H), 7.25 (d, J=8.0 Hz, 1H), 4.24-4.14 (m, 1H), 4.08-3.97 (m, 1H), 3.21-3.03 (m, 4H), 2.31-2.10 (m, 4H), 1.75-1.67 (m, 4H), 1.55-1.35 (m, 8H), 1.35-1.22 (m, 2H), 1.18-1.10 (m, 2H), 1.00-0.76 (m, 9H).

(4,4-Difluorocyclohexyl)methyl ((S)-4-methyl-1-oxo-1-(((S)-1-oxo-3-((S)-2-oxopyrrolidin-3-yl)propan-2-yl) amino)pentan-2-yl)carbamate (10b). Yield (51%). $^1$H NMR (400 MHz, DMSO-$d_6$) δ 9.40 (s, 1H), 8.44 (d, J=7.5 Hz, 1H), 7.95 (s, 1H), 7.36-7.28 (m, 1H), 4.19 (ddd, J=11.4, 7.6, 4.2 Hz, 1H), 4.03 (td, J=8.8, 6.2 Hz, 1H), 3.84 (d, J=6.1 Hz, 2H), 3.24-3.02 (m, 2H), 2.37-2.08 (m, 2H), 2.08-1.94 (m, 2H), 1.94-1.80 (m, 1H), 1.80-1.55 (m, 7H), 1.55-1.33 (m, 2H), 1.33-1.11 (m, 3H), 0.97-0.79 (m, 6H). HRMS m/z: $[M+H]^+$ Calculated for $C_{21}H_{34}F_2N_3O_5$ 446.2467; Found 446.2452, m/z: $[M+Na]^+$ Calculated for $C_{21}H_{33}F_2N_3O_5Na$ 468.2286; Found 468.2281.

(4,4-Difluorocyclohexyl) methyl-$d_2$ ((2S)-4-methyl-1-oxo-1-(((2S)-1-oxo-3-(2-oxopyrrolidin-3-yl) propan-2-yl) amino) pentan-2-yl) carbamate (11b). Yield (63%). $^1$H NMR (400 MHz, DMSO-$d_6$) δ 9.40 (s, 1H), 8.44 (d, J=7.5 Hz, 1H), 7.63 (s, 1H), 7.32 (d, J=8.1 Hz, 1H), 4.23-4.15 (m, 1H), 4.07-3.99 (m, 1H), 3.21-3.05 (m, 2H), 2.32-2.20 (m, 1H), 2.19-2.10 (m, 2H), 2.05-1.95 (m, 2H), 1.79-1.58 (m, 8H), 1.55-1.40 (m, 2H), 1.30-1.15 (m, 2H), 0.92-0.83 (m, 6H).

1-(4,4-Difluorocyclohexyl)ethyl ((S)-4-methyl-1-oxo-1-(((S)-1-oxo-3-((S)-2-oxopyrrolidin-3-yl)propan-2-yl) amino)pentan-2-yl)carbamate (12b). Yield (70%). $^1$H NMR (400 MHz, DMSO-$d_6$) δ 9.40 (s, 1H), 8.46-8.36 (m, 1H), 7.63 (s, 1H), 7.23 (d, J=8.2 Hz, 1H), 4.59-4.52 (m, 1H), 4.23-4.18 (m, 1H), 4.06-3.98 (m, 1H), 3.21-3.03 (m, 2H), 2.32-2.22 (m, 1H), 2.18-2.09 (m, 1H), 2.06-1.95 (m, 3H), 1.95-1.76 (m, 2H), 1.72-1.59 (m, 5H), 1.55-1.40 (m, 2H), 1.31-1.14 (m, 3H), 1.12 (d, J=6.3 Hz, 3H), 0.92-0.81 (m, 6H).

2-(4,4-Difluorocyclohexyl)propan-2-yl ((S)-4-methyl-1-oxo-1-(((S)-1-oxo-3-((S)-2-oxo pyrrolidin-3-yl)propan-2-yl)amino)pentan-2-yl)carbamate (13b). Yield (42%). $^1$H NMR (400 MHz, DMSO-$d_6$) δ 9.40 (s, 1H), 8.35 (d, J=7.7 Hz, 1H), 7.70-7.60 (m, 1H), 7.06 (d, J=8.1 Hz, 1H), 4.02-3.89 (m, 2H), 3.21-3.00 (m, 2H), 2.31-2.11 (m, 1H), 2.07-1.83 (m, 4H), 1.82-1.74 (m, 4H), 1.69-1.58 (m, 4H), 1.56-1.36 (m, 3H), 1.34 (s, 6H), 1.30-1.23 (m, 1H), 0.92-0.81 (m, 6H).

1-(4,4-Difluorocyclohexyl)-2-phenylethyl ((S)-4-methyl-1-oxo-1-(((S)-1-oxo-3-((S)-2-oxopyrrolidin-3-yl)propan-2-yl)amino)pentan-2-yl)carbamate (14b). Yield (80%). $^1$H NMR (400 MHz, DMSO-$d_6$) δ 9.39 (s, 1H), 8.38-8.30 (m, 1H), 7.62 (s, 1H), 7.26-7.15 (m, 5H), 4.77-4.73 (m, 1H), 4.22-4.18 (m, 1H), 3.93-3.87 (m, 1H), 3.18-2.99 (m, 2H), 2.92-2.83 (m, 1H), 2.78-2.68 (m, 1H), 2.32-2.18 (m, 1H), 2.16-2.07 (m, 1H), 2.07-1.94 (m, 2H), 1.91-1.80 (m, 3H), 1.79-1.68 (m, 1H), 1.67-1.41 (m, 7H), 1.41-1.27 (m, 3H), 0.92-0.80 (m, 4H), 0.75 (dd, J=11.6, 6.5 Hz, 2H).

(4,4-Difluorocyclohexyl)(phenyl)methyl ((S)-4-methyl-1-oxo-1-(((S)-1-oxo-3-((S)-2-oxopyrrolidin-3-yl)propan-2-yl)amino)pentan-2-yl)carbamate (15b). Yield (63%). $^1$H NMR (400 MHz, DMSO-$d_6$) δ 9.41 (s, 1H), 8.48-8.35 (m, 1H), 7.65 (d, J=5.4 Hz, 1H), 7.52-7.43 (m, 1H), 7.39-7.20 (m, 5H), 4.22-4.17 (m, 1H), 4.00-3.96 (m, 1H), 3.85 (d, J=6.0 Hz, 1H), 3.23-3.05 (m, 2H), 2.32-2.22 (m, 1H), 2.17-2.13 (m, 1H), 2.05-1.87 (m, 3H), 1.84-1.72 (m, 2H), 1.70-1.59 (m, 4H), 1.55-1.38 (m, 3H), 1.33-1.16 (m, 3H), 0.97-0.74 (m, 6H).

1-(4,4-Difluorocyclohexyl)pentyl ((S)-4-methyl-1-oxo-1-(((S)-1-oxo-3-((S)-2-oxopyrrolidin-3-yl)propan-2-yl) amino)pentan-2-yl)carbamate (16b). Yield (88%). $^1$H NMR (400 MHz, DMSO-$d_6$) δ 9.40 (s, 1H), 8.43 (d, J=7.6 Hz, 1H), 7.63 (s, 1H), 7.32 (d, J=8.0 Hz, 1H), 4.24-4.14 (m, 1H), 4.05-4.00 (m, 1H), 3.87-3.81 (m, 1H), 3.21-3.04 (m, 2H), 2.30-2.22 (m, 1H), 2.19-2.08 (m, 1H), 2.06-1.94 (m, 3H), 1.94-1.80 (m, 3H), 1.79-1.71 (m, 5H), 1.69-1.58 (m, 4H), 1.55-1.41 (m, 3H), 1.26-1.18 (m, 3H), 0.92-0.81 (m, 9H).

2-Fluorobenzyl ((S)-4-methyl-1-oxo-1-(((S)-1-oxo-3-((S)-2-oxopyrrolidin-3-yl)propan-2-yl)amino)pentan-2-yl) carbamate (17b). Yield (68%). $^1$H NMR (400 MHz, $CDCl_3$) δ 9.48 (s, 1H), 8.35 (d, J=5.9 Hz, 1H), 7.39 (t, J=7.6 Hz, 1H), 7.35-7.27 (m, 1H), 7.18-7.00 (m, 2H), 6.02 (s, 1H), 5.38 (d, J=8.5 Hz, 1H), 5.22-5.16 (m, 2H), 4.44-4.26 (m, 2H), 3.39-3.27 (m, 2H), 2.49-2.30 (m, 2H), 2.01-1.92 (m, 2H), 1.91-1.80 (m, 1H), 1.81-1.45 (m, 3H), 0.97 (d, J=5.8 Hz, 6H). HRMS m/z: $[M+Na]^+$ Calculated for $C_{21}H_{28}FN_3NaO_5$: 444.1911, Found: 444.1907.

3-Fluorobenzyl ((S)-4-methyl-1-oxo-1-(((S)-1-oxo-3-((S)-2-oxopyrrolidin-3-yl)propan-2-yl)amino)pentan-2-yl) carbamate (18b). Yield (68%). $^1$H NMR (400 MHz, $CDCl_3$) δ 9.48 (s, 1H), 8.45 (d, J=5.7 Hz, 1H), 7.35-7.24 (m, 1H), 7.13-7.05 (m, 2H), 7.05-6.94 (m, 1H), 6.18 (s, 1H), 5.48 (d, J=8.6 Hz, 1H), 5.16-5.03 (m, 2H), 4.41-4.26 (m, 2H), 3.41-3.27 (m, 2H), 2.56-2.29 (m, 2H), 2.00-1.79 (m, 2H), 1.77-1.64 (m, 3H), 1.60-1.51 (m, 1H), 0.97 (d, J=6.0 Hz, 6H). HRMS m/z: $[M+Na]^+$ Calculated for $C_{21}H_{28}FN_3NaO_5$: 444.1911, Found: 444.1911.

4-Fluorobenzyl ((S)-4-methyl-1-oxo-1-(((S)-1-oxo-3-((S)-2-oxopyrrolidin-3-yl)propan-2-yl)amino)pentan-2-yl) carbamate (19b). Yield (60%). $^1H$ NMR (400 MHz, $CDCl_3$) δ 9.48 (s, 1H), 8.36 (d, J=5.7 Hz, 1H), 7.38-7.29 (m, 2H), 7.09-6.98 (m, 2H), 6.00 (s, 1H), 5.36 (d, J=8.6 Hz, 1H), 5.11-5.04 (m, 2H), 4.35-4.28 (m, 2H), 3.41-3.28 (m, 2H), 2.50-2.31 (m, 2H), 1.97-1.93 (m, 1H), 1.90-1.76 (m, 1H), 1.74-1.65 (m, 3H), 1.59-1.51 (m, 1H), 0.96 (d, J=6.0 Hz, 6H). HRMS m/z: $[M+H]^+$ Calculated for $C_{21}H_{29}FN_3O_5$: 422.2091, Found: 422.2085. HRMS m/z: $[M+Na]^+$ Calculated for $C_{21}H_{28}FN_3NaO_5$: 444.1911, Found: 444.1903.

(4-Fluorophenyl)methyl-d2 ((S)-4-methyl-1-oxo-1-(((S)-1-oxo-3-((S)-2-oxopyrrolidin-3-yl)propan-2-yl)amino)pentan-2-yl)carbamate (20b). Yield (75%). $^1H$ NMR (400 MHz, $CDCl_3$) δ 9.48 (s, 1H), 8.36 (d, J=5.7 Hz, 1H), 7.37-7.28 (m, 2H), 7.08-6.98 (m, 2H), 6.06 (s, 1H), 5.38 (d, J=8.6 Hz, 1H), 4.39-4.14 (m, 2H), 3.41-3.30 (m, 2H), 2.48-2.29 (m, 2H), 2.01-1.92 (m, 1H), 1.92-1.80 (m, 1H), 1.80-1.62 (m, 3H), 1.59-1.46 (m, 1H), 0.96 (d, J=5.9 Hz, 6H). HRMS m/z: $[M+H]^+$ Calculated for $C_{21}H_{27}D_2FN_3O_5$: 424.2217, Found: 424.2210. HRMS m/z: $[M+Na]^+$ Calculated for $C_{21}H_{26}D_2FN_3NaO_5$: 446.2037, Found: 446.2027.

(Perfluorophenyl)methyl ((2S)-4-methyl-1-oxo-1-(((2S)-1-oxo-3-(2-oxopyrrolidin-3-yl) propan-2-yl) amino) pentan-2-yl) carbamate (21b). Yield (86%). $^1H$ NMR (400 MHz, DMSO-$d_6$) δ 9.39 (s, 1H), 8.47 (d, J=7.5 Hz, 1H), 7.63 (s, 1H), 7.59 (d, J=7.8 Hz, 1H), 5.14 (s, 2H), 4.23-4.14 (m, 1H), 4.07-3.98 (m, 1H), 3.22-3.03 (m, 2H), 2.33-2.20 (m, 1H), 2.17-2.06 (m, 2H), 1.93-1.83 (m, 1H), 1.70-1.56 (m, 2H), 1.51-1.39 (m, 2H), 0.91-0.80 (m, 6H).

(Perfluorophenyl)methyl-d2 ((2S)-4-methyl-1-oxo-1-(((2S)-1-oxo-3-(2-oxopyrrolidin-3-yl) propan-2-yl) amino) pentan-2-yl) carbamate (22b). Yield (83%). $^1H$ NMR (400 MHz, DMSO-$d_6$) δ 9.38 (s, 1H), 8.46 (d, J=7.6 Hz, 1H), 7.63 (s, 1H), 7.58 (d, J=7.8 Hz, 1H), 4.22-4.14 (m, 1H), 4.06-3.99 (m, 1H), 3.20-3.05 (m, 2H), 2.27 (d, J=7.9 Hz, 1H), 2.16-2.07 (m, 2H), 1.92-1.83 (m, 1H), 1.68-1.58 (m, 2H), 1.50-1.41 (m, 2H), 0.90-0.80 (m, 6H).

1-Phenylbutyl ((S)-4-methyl-1-oxo-1-(((S)-1-oxo-3-((S)-2-oxopyrrolidin-3-yl)propan-2-yl) amino)pentan-2-yl)carbamate (23b). Yield (71%). $^1H$ NMR (400 MHz, $CDCl_3$) δ 9.44 (d, J=36.5 Hz, 1H), 8.21 (dd, J=43.6, 6.1 Hz, 1H), 7.41-7.17 (m, 5H), 6.28 (d, J=30.3 Hz, 1H), 5.68-5.54 (m, 1H), 5.36 (dd, J=26.5, 8.5 Hz, 1H), 4.40-4.19 (m, 2H), 3.41-3.15 (m, 2H), 2.56-2.14 (m, 2H), 2.01-1.81 (m, 3H), 1.77-1.62 (m, 3H), 1.59-1.44 (m, 1H), 1.42-1.25 (m, 1H), 1.00-0.77 (m, 11H).

1,2-Diphenylethyl ((S)-4-methyl-1-oxo-1-(((S)-1-oxo-3-((S)-2-oxopyrrolidin-3-yl)propan-2-yl)amino)pentan-2-yl) carbamate (24b). Yield (82%). $^1H$ NMR (400 MHz, DMSO-$d_6$) δ 9.35 (dd, J=24.5, 7.6 Hz, 1H), 8.48-8.32 (m, 1H), 7.61 (d, J=21.6 Hz, 1H), 7.53-7.42 (m, 1H), 7.36-7.09 (m, 10H), 5.83-5.71 (m, 1H), 4.24-4.08 (m, 1H), 4.06-3.89 (m, 1H), 3.24-2.86 (m, 4H), 2.34-2.05 (m, 3H), 1.94-1.78 (m, 1H), 1.67-1.28 (m, 4H), 0.90-0.68 (m, 6H).

Preparation of compounds 1-24c. General procedure. To a solution of dipeptidyl aldehyde b (1 eq) in ethyl acetate (10 mL/g of dipeptidyl aldehyde) was added absolute ethanol (5 mL/g of dipeptidyl aldehyde) with stirring, followed by a solution of sodium bisulfite (1 eq) in water (1 mL/g of dipeptidyl aldehyde). The reaction mixture was stirred for 3 h at 50° C. The reaction mixture was allowed to cool to room temperature and then vacuum filtered. The solid was thoroughly washed with absolute ethanol and the filtrate was dried over anhydrous sodium sulfate, filtered, and concentrated to yield a white solid. The white solid was stirred with dry ethyl ether (3×10 mL/g of dipeptidyl aldehyde), followed by careful removal of the solvent using a pipette and dried using a vacuum pump for 2 h to yield dipeptidyl bisulfite adduct c as a white solid. The general reaction scheme is illustrated in FIG. 10B.

Sodium (2S)-2-((S)-2-((((4,4-dimethylcyclohexyl)oxy) carbonyl)amino)-4-methylpentan amido)-1-hydroxy-3-((S)-2-oxopyrrolidin-3-yl)propane-1-sulfonate (1c). Yield (39%). $^1H$ NMR (400 MHz, DMSO-$d_6$) δ 7.50 (dd, J=13.4, 9.1 Hz, 1H), 7.44 (s, 1H), 7.21-7.11 (m, 1H), 5.45-5.27 (m, 1H), 4.53-4.39 (m, 1H), 4.01-3.92 (m, 1H), 3.95-3.78 (m, 1H), 3.14-3.08 (m, 1H), 3.06-3.01 (m, 1H), 2.19-2.05 (m, 1H), 2.04-1.86 (m, 1H), 1.70-1.65 (m, 3H), 1.62-1.52 (m, 3H), 1.52-1.31 (m, 6H), 1.28-1.09 (m, 2H), 0.92-0.80 (m, 12H).

Sodium (2S)-1-hydroxy-2-((S)-2-(((((1r,4S)-4-isopropylcyclohexyl)oxy)carbonyl)amino)-4-methylpentanamido)-3-((S)-2-oxopyrrolidin-3-yl)propane-1-sulfonate (2c). Yield (36%). $^1H$ NMR (400 MHz, DMSO-$d_6$) δ 7.54-7.42 (m, 2H), 7.23-7.11 (m, 1H), 5.45-5.28 (m, 1H), 4.41-4.30 (m, 1H), 4.00-3.89 (m, 1H), 3.89-3.78 (m, 1H), 3.17-3.09 (m, 1H), 3.08-2.97 (m, 1H), 2.14-2.04 (m, 2H), 2.01-1.84 (m, 3H), 1.73-1.65 (m, 2H), 1.62-1.51 (m, 3H), 1.48-1.34 (m, 3H), 1.30-1.14 (m, 2H), 1.01 (s, 3H), 0.89-0.80 (m, 12H).

Sodium (2S)-1-hydroxy-2-((S)-4-methyl-2-(((((1s,4S)-4-propylcyclohexyl)oxy)carbonyl) amino)pentanamido)-3-((S)-2-oxopyrrolidin-3-yl)propane-1-sulfonate (3c). Yield (40%). $^1H$ NMR (400 MHz, DMSO-$d_6$) δ 7.54-7.39 (m, 2H), 7.23-7.10 (m, 1H), 5.45-5.28 (m, 1H), 4.42-4.32 (m, 1H), 4.03-3.88 (m, 1H), 3.89-3.78 (m, 1H), 3.18-3.08 (m, 1H), 3.07-2.97 (m, 1H), 2.19-2.03 (m, 2H), 1.97-1.80 (m, 3H), 1.71 (d, J=13.2 Hz, 2H), 1.59-1.56 (m, 3H), 1.48-1.37 (m, 2H), 1.34-1.02 (m, 7H), 0.97-0.89 (m, 2H), 0.92-0.80 (m, 9H).

Sodium (2S)-2-((S)-2-(((((1s,4S)-4-butylcyclohexyl)oxy) carbonyl)amino)-4-methylpentan amido)-1-hydroxy-3-((S)-2-oxopyrrolidin-3-yl)propane-1-sulfonate (4c). Yield (33%). $^1H$ NMR (400 MHz, DMSO-$d_6$) δ 7.55-7.42 (m, 2H), 7.22-7.12 (m, 1H), 5.48-5.30 (m, 1H), 4.42-4.32 (m, 1H), 3.97-3.89 (m, 1H), 3.88-3.79 (m, 1H), 3.17-3.08 (m, 1H), 3.07-2.98 (m, 1H), 2.19-2.02 (m, 2H), 1.99-1.83 (m, 3H), 1.72 (d, J=13.3 Hz, 3H), 1.60-1.55 (m, 3H), 1.48-1.37 (m, 2H), 1.27-1.17 (m, 6H), 1.17-1.13 (m, 3H), 0.97-0.92 (m, 1H), 0.90-0.80 (m, 9H).

Sodium (2S)-1-hydroxy-2-((S)-4-methyl-2-(((((1r,4S)-4-phenylcyclohexyl)oxy)carbonyl) amino)pentanamido)-3-((S)-2-oxopyrrolidin-3-yl)propane-1-sulfonate (5c). Yield (35%). $^1H$ NMR (400 MHz, DMSO-$d_6$) δ 7.57-7.47 (m, 1H), 7.44 (s, 1H), 7.32-7.10 (m, 6H), 5.52-5.22 (m, 1H), 4.55-4.50 (m, 1H), 4.06-3.89 (m, 1H), 3.89-3.77 (m, 1H), 3.15-3.10 (m, 1H), 3.09-3.00 (m, 1H), 2.14-2.09 (m, 2H), 2.05-1.97 (m, 2H), 1.81 (d, J=13.1 Hz, 3H), 1.62-1.52 (m, 5H), 1.50-1.39 (m, 4H), 1.14-1.03 (m, 1H), 0.93-0.81 (m, 6H).

Sodium (2S)-1-hydroxy-2-((S)-4-methyl-2-((((4-(trifluoromethyl) cyclohexyl) methoxy) carbonyl) amino) pentanamido)-3-(2-oxopyrrolidin-3-yl) propane-1-sulfonate (6c). Yield (81%). $^1H$ NMR (400 MHz, DMSO-$d_6$) δ 7.62-7.49 (m, 1H), 7.46 (s, 1H), 7.25-7.13 (m, 1H), 5.50 (d, J=6.3 Hz, 1H), 5.34 (d, J=6.0 Hz, 1H), 4.41-4.33 (m, 1H), 4.27-4.18 (m, 1H), 3.81-3.70 (m, 2H), 3.13 (s, 2H), 3.08-2.99 (m, 1H), 2.20-2.06 (m, 3H), 1.91-1.76 (m, 4H), 1.63-1.57 (m, 4H), 1.49-1.37 (m, 1H), 1.27-1.16 (m, 1H), 1.13-0.92 (m, 4H), 0.93-0.80 (m, 6H).

Sodium (2S)-1-hydroxy-2-((S)-4-methyl-2-(((((1r,4S)-4-(trifluoromethyl) cyclohexyl) methoxy) carbonyl) amino) pentanamido)-3-(2-oxopyrrolidin-3-yl) propane-1-sulfonate (7c). Yield (76%). $^{1}$H NMR (400 MHz, DMSO-$d_6$) δ 7.58-7.50 (m, 1H), 7.46 (d, J=9.6 Hz, 1H), 7.25-7.16 (m, 1H), 5.41 (d, J=6.3 Hz, 1H), 5.28 (d, J=5.9 Hz, 1H), 4.45-4.32 (m, 1H), 4.00-3.90 (m, 2H), 3.50-3.25 (m, 1H), 3.08-3.01 (m, 2H), 2.31-2.26 (m, 3H), 2.15-2.08 (m, 1H), 1.90-1.85 (m, 4H), 1.67-1.33 (m, 10H), 0.91-0.81 (m, 6H).

Sodium (2S)-1-hydroxy-2-((S)-4-methyl-2-(((((1r,4R)-4-propylcyclohexyl) methoxy) carbonyl) amino) pentanamido)-3-(2-oxopyrrolidin-3-yl) propane-1-sulfonate (8c). Yield (82%). $^{1}$H NMR (400 MHz, DMSO-$d_6$) δ 7.53-7.40 (m, 1H), 7.20-7.09 (m, 1H), 6.10-6.04 (m, 1H), 5.41 (d, J=6.2 Hz, 1H), 5.29 (d, J=6.0 Hz, 1H), 4.43-4.32 (m, 1H), 4.00-3.89 (m, 1H), 3.74 (s, 2H), 3.16-3.01 (m, 2H), 2.15-2.05 (m, 6H), 1.71 (d, J=11.4 Hz, 10H), 1.53-1.36 (m, 2H), 1.35-1.22 (m, 2H), 1.19-1.03 (m, 2H), 0.98-0.77 (m, 9H).

Sodium (2S)-1-hydroxy-2-((S)-4-methyl-2-(((((1s,4S)-4-propylcyclohexyl) methoxy-d2) carbonyl) amino) pentanamido)-3-(2-oxopyrrolidin-3-yl) propane-1-sulfonate (9c). Yield (77%). $^{1}$H NMR (400 MHz, DMSO-$d_6$) δ 7.57-7.42 (m, 1H), 7.27-7.09 (m, 1H), 6.07 (d, J=10.0 Hz, 1H), 5.40 (d, J=6.4 Hz, 1H), 5.29 (d, J=6.0 Hz, 1H), 3.99-3.89 (m, 1H), 3.78-3.69 (m, 1H), 3.17-2.98 (m, 4H), 2.20-2.06 (m, 4H), 1.71 (d, J=11.6 Hz, 4H), 1.49-1.35 (m, 8H), 1.35-1.22 (m, 2H), 1.18-1.09 (m, 2H), 0.90-0.80 (m, 9H).

Sodium (2S)-2-((S)-2-((((4,4-difluorocyclohexyl) methoxy)carbonyl)amino)-4-methyl pentanamido)-1-hydroxy-3-((S)-2-oxopyrrolidin-3-yl)propane-1-sulfonate (10c). Yield (50.5%). $^{1}$H NMR (400 MHz, DMSO-$d_6$) δ 7.57 (t, J=8.9 Hz, 1H), 7.45 (s, 1H), 7.38-7.17 (m, 1H), 4.29-4.10 (m, 1H), 4.05-3.67 (m, 4H), 3.09 (dt, J=29.8, 8.8 Hz, 2H), 2.33-2.05 (m, 2H), 2.05-1.88 (m, 4H), 1.88-1.64 (m, 5H), 1.64-1.48 (m, 2H), 1.43 (q, J=7.3 Hz, 2H), 1.30-1.11 (m, 2H), 1.04-0.78 (m, 6H).

Sodium (2S)-2-((S)-2-((((4,4-difluorocyclohexyl) methoxy-$d_2$) carbonyl) amino)-4-methylpentanamido)-1-hydroxy-3-(2-oxopyrrolidin-3-yl) propane-1-sulfonate (11c). Yield (81%). $^{1}$H NMR (400 MHz, DMSO-$d_6$) δ 7.60-7.50 (m, 1H), 7.45 (s, 1H), 7.29-7.18 (m, 1H), 5.41 (d, J=6.3 Hz, 1H), 5.24 (d, J=6.0 Hz, 1H), 4.37-4.32 (m, 1H), 3.98-3.89 (m, 1H), 3.15-3.02 (m, 2H), 2.14-2.05 (m, 3H), 2.01-1.96 (m, 1H), 1.84-1.70 (m, 8H), 1.62-1.53 (m, 4H), 1.45-1.38 (m, 1H), 0.90-0.80 (m, 6H).

Sodium (2S)-2-((2S)-2-(((1-(4,4-difluorocyclohexyl) ethoxy)carbonyl)amino)-4-methylpentan amido)-1-hydroxy-3-((S)-2-oxopyrrolidin-3-yl)propane-1-sulfonate (12c). Yield (48%). $^{1}$H NMR (400 MHz, DMSO-$d_6$) δ 7.52 (d, J=9.9 Hz, 1H), 7.43 (s, 1H), 7.28-7.13 (m, 1H), 5.36-5.17 (m, 1H), 4.58-4.51 (m, 1H), 3.96-3.91 (m, 1H), 3.83-3.78 (m, 1H), 3.18-3.09 (m, 1H), 3.06-3.01 (m, 1H), 2.17-1.88 (m, 3H), 1.87-1.77 (m, 4H), 1.74-1.66 (m, 2H), 1.65-1.51 (m, 3H), 1.48-1.35 (m, 2H), 1.30-1.16 (m, 3H), 1.16-1.04 (m, 3H), 0.89-0.80 (m, 6H).

Sodium (2S)-2-((S)-2-((((2-(4,4-difluorocyclohexyl)propan-2-yl)oxy)carbonyl)amino)-4-methylpentanamido)-1-hydroxy-3-((S)-2-oxopyrrolidin-3-yl)propane-1-sulfonate (13c). Yield (39%). $^{1}$H NMR (400 MHz, DMSO-$d_6$) δ 7.49 (d, J=10.6 Hz, 1H), 7.43 (s, 1H), 7.12-6.95 (m, 1H), 5.47-5.26 (m, 1H), 4.06-3.71 (m, 2H), 3.17-3.08 (m, 1H), 3.08-2.97 (m, 1H), 2.14-1.93 (m, 6H), 1.86-1.65 (m, 5H), 1.64-1.49 (m, 2H), 1.44-1.36 (m, 2H), 1.33 (s, 6H), 1.28-1.23 (m, 2H), 0.84 (ddd, J=11.6, 6.5, 3.0 Hz, 6H).

Sodium (2S)-2-((2S)-2-(((1-(4,4-difluorocyclohexyl)-2-phenylethoxy)carbonyl)amino)-4-methylpentanamido)-1-hydroxy-3-((S)-2-oxopyrrolidin-3-yl)propane-1-sulfonate (14c). Yield (41%). $^{1}$H NMR (400 MHz, DMSO-$d_6$) δ 7.53-7.47 (m, 1H), 7.43 (s, 1H), 7.39-7.33 (m, 1H), 7.28-7.15 (m, 5H), 5.38-5.15 (m, 1H), 4.75-4.71 (m, 1H), 3.96-3.91 (m, 1H), 3.87-3.68 (m, 1H), 3.13-3.09 (m, 2H), 3.07-2.96 (m, 1H), 2.90-2.82 (m, 1H), 2.00 (s, 4H), 1.92-1.80 (m, 3H), 1.76 (s, 3H), 1.59-1.51 (m, 4H), 1.49-1.33 (m, 3H), 0.89-0.79 (m, 4H), 0.79-0.67 (m, 2H).

Sodium (2S)-2-((2S)-2-((((4,4-difluorocyclohexyl)(phenyl)methoxy)carbonyl)amino)-4-methylpentanamido)-1-hydroxy-3-((S)-2-oxopyrrolidin-3-yl)propane-1-sulfonate (15c). Yield (66%). $^{1}$H NMR (400 MHz, DMSO-$d_6$) δ 7.64-7.50 (m, 1H), 7.49-7.44 (m, 1H), 7.42-7.19 (m, 6H), 5.48-5.35 (m, 1H), 4.01-3.75 (m, 3H), 3.18-3.10 (m, 1H), 3.08-3.01 (m, 1H), 2.22-2.06 (m, 1H), 2.06-1.91 (m, 3H), 1.87-1.68 (m, 4H), 1.61-1.54 (m, 3H), 1.49-1.40 (m, 3H), 1.35-1.14 (m, 3H), 0.93-0.71 (m, 6H).

Sodium (2S)-2-((2S)-2-((((1-(4,4-difluorocyclohexyl) pentyl)oxy)carbonyl)amino)-4-methyl pentanamido)-1-hydroxy-3-((S)-2-oxopyrrolidin-3-yl)propane-1-sulfonate (16c). Yield (58%). $^{1}$H NMR (400 MHz, DMSO-$d_6$) δ 7.60-7.51 (m, 1H), 7.44 (s, 1H), 7.38-7.23 (m, 1H), 5.46-5.21 (m, 1H), 3.98-3.74 (m, 3H), 3.14-3.07 (m, 1H), 3.06-2.98 (m, 1H), 2.16-2.04 (m, 2H), 2.04-1.92 (m, 4H), 1.86-1.66 (m, 8H), 1.64-1.52 (m, 3H), 1.49-1.36 (m, 3H), 1.21-1.17 (m, 3H), 0.83 (ddd, J=11.9, 6.5, 3.1 Hz, 9H).

Sodium (2S)-2-((S)-2-((((2-fluorobenzyl)oxy)carbonyl) amino)-4-methylpentanamido)-1-hydroxy-3-((S)-2-oxopyrrolidin-3-yl)propane-1-sulfonate (17c). Yield (71%). $^{1}$H NMR (400 MHz, DMSO-$d_6$) δ 7.77-7.70 (m, 1H), 7.70-7.59 (m, 1H), 7.59-7.33 (m, 3H), 7.26-7.12 (m, 2H), 5.65 (d, J=78.6 Hz, 1H), 5.16-5.01 (m, 2H), 4.11-3.84 (m, 2H), 3.17-2.97 (m, 2H), 2.39-2.07 (m, 2H), 2.07-1.85 (m, 1H), 1.70-1.51 (m, 3H), 1.51-1.33 (m, 2H), 0.92-0.77 (m, 6H). HRMS m/z: $[M]^-$ Calculated for $C_{21}H_{29}FN_3O_8S$: 502.1659, Found: 502.1650. HRMS m/z: $[M+Na]^+$ Calculated for $C_{21}H_{29}FN_3Na_2O_8S$: 548.1455, Found: 548.1446.

Sodium (2S)-2-((S)-2-((((3-fluorobenzyl)oxy)carbonyl) amino)-4-methylpentanamido)-1-hydroxy-3-((S)-2-oxopyrrolidin-3-yl)propane-1-sulfonate (18c). Yield (89%). $^{1}$H NMR (400 MHz, DMSO-$d_6$) δ 7.75 (d, J=9.0 Hz, 1H), 7.64 (d, J=9.3 Hz, 1H), 7.57 (d, J=7.9 Hz, 1H), 7.54-7.35 (m, 2H), 7.25-7.08 (m, 2H), 5.75-5.46 (m, 1H), 5.15-4.98 (m, 2H), 4.13-3.87 (m, 2H), 3.17-2.89 (m, 2H), 2.23-2.04 (m, 2H), 2.04-1.91 (m, 1H), 1.89-1.74 (m, 1H), 1.70-1.31 (m, 4H), 0.91-0.77 (m, 6H). HRMS m/z: $[M+Na]^+$ Calculated for $C_{21}H_{29}FN_3Na_2O_8S$: 548.1455, Found: 548.1450. HRMS m/z: $[M]^-$ Calculated for $C_{21}H_{29}FN_3O_8S$: 502.1659, Found: 502.1655.

Sodium (2S)-2-((S)-2-((((4-fluorobenzyl)oxy)carbonyl) amino)-4-methylpentanamido)-1-hydroxy-3-((S)-2-oxopyrrolidin-3-yl)propane-1-sulfonate (19c). Yield (68%). $^{1}$H NMR (400 MHz, DMSO-$d_6$) δ 7.70-7.57 (m, 1H), 7.57-7.49 (m, 1H), 7.48-7.37 (m, 3H), 7.23-7.14 (m, 2H), 5.43 (d, J=85.6 Hz, 1H), 5.09-4.92 (m, 2H), 4.12-3.81 (m, 2H), 3.14-2.94 (m, 2H), 2.23-1.91 (m, 2H), 1.62-1.50 (m, 4H), 1.50-1.38 (m, 2H), 0.90-0.80 (m, 6H). HRMS m/z: $[M+Na]^+$ Calculated for $C_{21}H_{29}FN_3Na_2O_8S$: 548.1455, Found: 548.1448. HRMS m/z: $[M]^-$ Calculated for $C_{21}H_{29}FN_3O_8S$: 502.1659, Found: 502.1645.

Sodium (2S)-2-((S)-2-((((4-fluorophenyl)methoxy-d2) carbonyl)amino)-4-methylpentan amido)-1-hydroxy-3-((S)-2-oxopyrrolidin-3-yl)propane-1-sulfonate (20c). Yield (90%). $^{1}$H NMR (400 MHz, DMSO-$d_6$) δ 7.68 (d, J=9.2 Hz, 1H), 7.63 (d, J=9.2 Hz, 1H), 7.53 (d, J=7.8 Hz, 1H), 7.48-7.35 (m, 2H), 7.23-7.13 (m, 2H), 5.52 (dd, J=85.5, 6.2 Hz, 1H), 4.04-3.84 (m, 2H), 3.18-2.97 (m, 2H), 2.27-1.90 (m, 2H), 1.63-1.50 (m, 3H), 1.53-1.38 (m, 3H), 0.92-0.78

(m, 6H). HRMS m/z: [M+Na] Calculated for $C_{21}H_{27}D_2FN_3Na_2O_8S$: 550.1581, Found: 550.1573. HRMS m/z: $[M+Na]^+$ Calculated for $C_{21}H_{27}D_2FN_3O_8S$: 504.1785, Found: 504.1769.

Sodium (2S)-1-hydroxy-2-((S)-4-methyl-2-((((perfluorophenyl) methoxy) carbonyl) amino) pentanamido)-3-(2-oxopyrrolidin-3-yl) propane-1-sulfonate (21c). Yield (81%). $^1H$ NMR (400 MHz, DMSO-$d_6$) δ 7.68-7.42 (m, 2H), 6.06 (s, 1H), 5.41 (d, J=6.3 Hz, 1H), 5.24 (d, J=5.9 Hz, 1H), 5.13 (s, 2H), 4.36 (d, J=7.2 Hz, 1H), 4.01-3.89 (m, 1H), 3.48-3.41 (m, 3H), 2.20-2.04 (m, 3H), 1.63-1.33 (m, 4H), 0.89-0.78 (m, 6H).

Sodium (2S)-1-hydroxy-2-((S)-4-methyl-2-((((perfluorophenyl)methoxy-d2) carbonyl) amino) pentanamido)-3-(2-oxopyrrolidin-3-yl) propane-1-sulfonate (22c). Yield (89%). $^1H$NMR (400 MHz, DMSO-$d_6$) δ 7.67 (d, J=9.1 Hz, 1H), 7.58 (s, 1H), 7.50 (d, J=8.8 Hz, 1H), 5.12 (d, J=12.4 Hz, 1H), 4.42-4.36 (m, 1H), 3.99-3.90 (m, 2H), 3.16-3.00 (m, 2H), 2.20-2.05 (m, 3H), 1.77 (s, 1H), 1.62-1.50 (m, 2H), 1.47-1.37 (m, 2H), 0.88-0.78 (m, 6H).

Sodium(2S)-1-hydroxy-2-((2S)-4-methyl-2-(((1-phenylbutoxy)carbonyl)amino)pentanamido)-3-((S)-2-oxopyrrolidin-3-yl)propane-1-sulfonate (23c). Yield (63%). $^1H$ NMR (400 MHz, DMSO-$d_6$) δ 7.60 (d, J=9.8 Hz, 1H), 7.47 (d, J=5.0 Hz, 1H), 7.41 (d, J=7.4 Hz, 1H), 7.38-7.22 (m, 5H), 5.54 (t, J=6.6, 6.6 Hz, 1H), 5.37-5.25 (m, 1H), 4.12-3.78 (m, 2H), 3.17-2.95 (m, 2H), 2.31-1.88 (m, 3H), 1.85-1.38 (m, 4H), 1.36-1.18 (m, 2H), 0.93-0.82 (m, 10H), 0.79-0.70 (m, 2H).

Sodium (2S)-2-((2S)-2-(((1,2-diphenylethoxy)carbonyl) amino)-4-methylpentanamido)-1-hydroxy-3-((S)-2-oxopyrrolidin-3-yl)propane-1-sulfonate (24c). Yield (69%). $^1H$ NMR (400 MHz, DMSO-$d_6$) δ 7.69-7.36 (m, 2H), 7.36-7.07 (m, 11H), 5.82-5.71 (m, 1H), 5.59-5.32 (m, 1H), 4.15-3.81 (m, 2H), 3.18-2.76 (m, 4H), 2.32-1.72 (m, 4H), 1.71-1.30 (m, 4H), 0.90-0.60 (m, 6H).

Enzyme assays and inhibition studies. Cloning and expression of the 3CL protease of SARS-CoV-2 and FRET enzyme assays. The codon-optimized cDNA of full length of 3CLpro of SARS-CoV-2 (GenBank number MN908947.3) fused with sequences encoding 6 histidine at the N-terminal was synthesized by Integrated DNA (Coralville, IA). The synthesized gene was subcloned into the pET-28a(+) vector. The expression and purification of SARS-CoV-2 3CLpro were conducted following a standard procedure described previously. Briefly, a stock solution of an inhibitor was prepared in DMSO and diluted in assay buffer comprised of 20 mM HEPES buffer, pH 8, containing NaCl (200 mM), EDTA (0.4 mM), glycerol (60%), and 6 mM dithiothreitol (DTT). The SARS-CoV-2 protease was mixed with serial dilutions of inhibitor or with DMSO in 25 μL of assay buffer and incubated at 37° C. for 1 h, followed by the addition of 25 μL of assay buffer containing substrate (FAM-SAVLQ/SG-QXL® 520, AnaSpec, Fremont, CA). The substrate was derived from the cleavage sites on the viral polyproteins of SARS-CoV. Fluorescence readings were obtained using an excitation wavelength of 480 nm and an emission wavelength of 520 nm on a fluorescence microplate reader (FLx800; Biotec, Winoosk, VT) 1 h following the addition of substrate. Relative fluorescence units (RFU) were determined by subtracting background values (substrate-containing well without protease) from the raw fluorescence values, as described previously. The dose-dependent FRET inhibition curves were fitted with a variable slope by using GraphPad Prism software (GraphPad, La Jolla, CA) in order to determine the $IC_{50}$ values of the compounds. The expression and purification of the 3CLpro of MERS-CoV, as well as the FRET enzyme assays were performed as described previously.

Cell-based assay for antiviral activity. Compounds 2a and 3a were investigated for their antiviral activity against the replication of SARS-CoV-2. Briefly, confluent Vero E6 cells were inoculated with SARS-CoV-2 at 50-100 plaque forming units/well, and medium containing various concentrations of each compound and agar was applied to the cells. After 48-72 hr, plaques in each well were counted. The 50% effective concentration ($EC_{50}$) values were determined by GraphPad Prism software using a variable slope (GraphPad, La Jolla, CA).

Nonspecific cytotoxic effects/In vitro cytotoxicity. Confluent cells grown in 96-well plates were incubated with various concentrations (1 to 100 μM) of each compound for 72 h. Cell cytotoxicity was measured by a CytoTox 96 nonradioactive cytotoxicity assay kit (Promega, Madison, WI), and the $CC_{50}$ values were calculated using a variable slope by GraphPad Prism software. The in vitro Safety Index was calculated by dividing the $CC_{50}$ by the $IC_{50}$.

X-ray Crystallographic Studies. Crystallization and Data Collection. Purified SARS-CoV-2 3CLpro[17] in 100 mM NaCl, 20 mM Tris pH 8.0 was concentrated to 9.6 mg/mL (0.28 mM) for crystallization screening. All crystallization experiments were setup using an NT8 drop-setting robot (Formulatrix Inc.) and UVXPO MRC (Molecular Dimensions) sitting drop vapor diffusion plates at 18° C. 100 nL of protein and 100 nL crystallization solution were dispensed and equilibrated against 50 uL of the latter. A stock solution of 100 mM inhibitor was prepared in DMSO and the SARS-CoV-2 3CLpro:inhibitor complex was prepared by mixing 1 μL of the ligand (2 mM) with 49 μL (0.28 mM) of SARS2 3CLpro and incubating on ice for 1 hour. Crystals were obtained in 1-2 days from various conditions for the following complexes. 8b (NN-II-111): Proplex HT screen (Molecular Dimensions) condition F7 (0.5 M ammonium sulfate, 100 mM MES pH 6.5). 12b, AMJ-I-106, 13c (AMJ-I-114), 14c (AMJ-I-111) and 21c (NN-II-123): Index HT screen (Hampton Research) condition D10 (20% (w/v) PEG 5000 MME, 100 mM Bis-Tris pH 6.5). 19b (CSD-III-008) and 20b (CSD-III-009): Proplex HT screen (Rigaku Reagents) condition C5 (20% (w/v) PEG 4000, 100 mM Tris pH 8.0). 1c (AMJ-I-158): Index HT screen (Hampton Research) condition F2 (20% (w/v) PEG 2000 MME, 100 mM Tris pH 8.5, 200 mM Trimethylamine N-oxide dihydrate). 3c (AMJ-I-159): Index HT screen (Hampton Research) condition F5 (17% (w/v) PEG 10,000, 100 mM Bis-Tris pH 5.5, 100 mM ammonium acetate). 5c (AMJ-I-157): Index HT screen (Hampton Research) condition F1 (10% (w/v) PEG 3350, 100 mM Hepes pH 7.5, 200 L-proline). 17c (CSD-III-028) and 18c (CSD-III-029): Index HT screen (Rigaku Reagents) condition H11 (30% (w/v) PEG 2000 MME, 100 mM potassium thiocyanate). Samples were transferred to a fresh drop composed of 80% crystallization solution and 20% (v/v) PEG 200 and stored in liquid nitrogen. Crystals of SARS-CoV-2 3CLpro with 8b were transferred to a cryoprotectant solution containing 80% crystallant and 20% (v/v) glycerol prior to freezing. X-ray diffraction data were collected at the Advanced Photon Source beamline except for the SARS-CoV-2 3CLpro complex with 14c which were collected at the National Synchrotron Light Source II (NSLS-II) AMX beamline 17-ID-1. All diffraction data were collected using a Dectris Eiger2× 9M pixel array detector.

Structure Solution and Refinement. Intensities were integrated using XDS via Autoproc and the Laue class analysis and data scaling were performed with Aimless. Structure solution was conducted by molecular replacement with Phaser using a previously determined structure of SARS2 3CLpro (PDB 6XMK) as the search model. Structure refinement and manual model building were conducted with Phenix and Coot respectively. Disordered side chains were truncated to the point for which electron density could be observed. Structure validation was conducted with Molprobity and figures were prepared using the CCP4MG package.

Coordinates and structure factors for the following SARS2 3CLpro complexes with inhibitors were deposited to the Worldwide Protein Databank (wwPDB) with the accession codes: 8b (NN-II-111), 12b (AMJ-I-106), 19b (CSD-III-008), 20b (CSD-III-009), 1c (AMJ-I-158), 3c (AMJ-I-159), 5c (AMJ-I-157), 13c (AMJ-I-114), 14c (AMJ-I-111), 17c (CSD-III-028), 18c (CSD-III-029) and 21c (NN-II-123).

Example 5

Using the new reaction scheme described in Example 4, additional phenyl derivative compounds have been synthesized, using the following alcohol inputs:

A

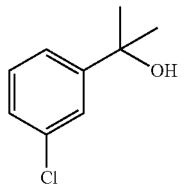

B

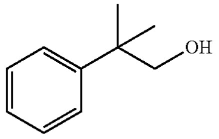

C

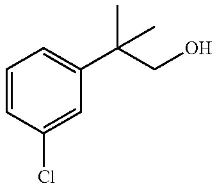

D

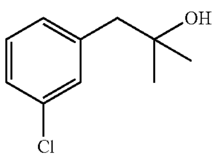

E

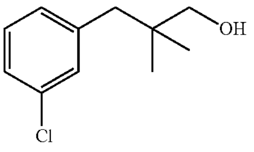

F

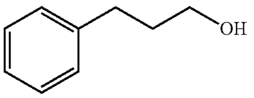

-continued

G

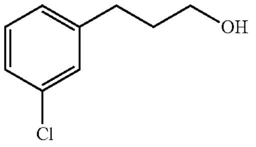

H

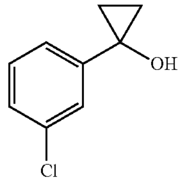

I

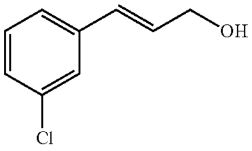

The inhibitory activity of the synthesized compounds against NV 3CLpro and their anti-norovirus activity in a cell-based replicon system, were evaluated similar to MERS and SARS. The determined $IC_{50}$ values in enzyme assay, $EC_{50}$ values against NV in the replicon harboring cells (HG23 cells), and $CC_{50}$ values in HG23 cells are listed in following Tables (see also Tables 4B, 5B, and 6B) and they are the average of at least two determinations.

TABLE 11

In Vitro and Cell-based Activity, and Cell-cytotoxicity Values of Norovirus 3CL Protease Inhibitors 5, 6 (q, r).

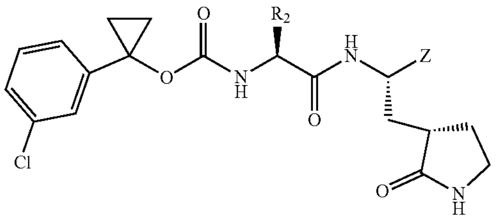

| Compound | $R_2$ | Z | $IC_{50}$ (μM) ± SD | $EC_{50}$ (μM) ± SD | $CC_{50}$ (μM) ± SD |
|---|---|---|---|---|---|
| 5q | Cha | CHO | 0.28 ± 0.06 | 0.25 ± 0.07 | 36.5 ± 7.1 |
| 6q | | $CH(OH)SO_3Na$ | 0.27 ± 0.04 | 0.18 ± 0.04 | 42.3 ± 15.6 |
| 5r | Leu | CHO | 0.28 ± 0.03 | 0.65 ± 0.2 | >100 |
| 6r | | $CH(OH)SO_3Na$ | 0.25 ± 0.08 | 0.55 ± 0.08 | >100 |

TABLE 12

In Vitro and Cell-based Activity, and Cell-cytotoxicity Values of Norovirus 3CL Protease Inhibitors 5 and 6 (j, k, m, n, o), and 7 (k, l, o)

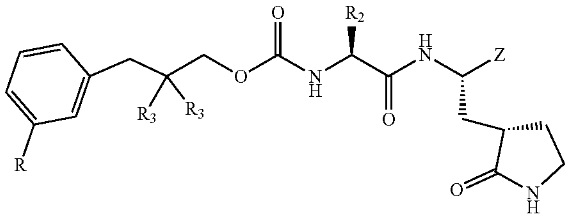

| Compound | R | $R_2$ | $R_3$ | Z | $IC_{50}$ (μM) ± SD | $EC_{50}$ (μM) ± SD | $CC_{50}$ (μM) ± SD |
|---|---|---|---|---|---|---|---|
| 5j | m-Cl | Cha | H | CHO | 0.17 ± 0.02 | 0.08 ± 0.01 | 30.3 ± 2.83 |
| 6j | | | | $CH(OH)SO_3Na$ | 0.18 ± 0.05 | 0.06 ± 0.02 | 35.2 ± 4.1 |
| 5k | | | $CH_3$ | CHO | 0.11 ± 0.02 | 0.06 ± 0.01 | 14.1 ± 1.7 |
| 6k | | | | $CH(OH)SO_3Na$ | 0.14 ± 0.05 | 0.07 ± 0.02 | 16.2 ± 3.82 |
| 7k | | | | $CH[O(C{=}O)CH_2CH_3]SO_3Na$ | 0.34 ± 0.1 | 0.1 ± 0.06 | 18.4 ± 2.63 |
| 7l | | | | $CH[O(C{=}O)(CH_2)_4CH3]SO_3N$ | 0.34 ± 0.06 | 0.08 ± 0.02 | 20.7 ± 4.03 |
| 5m | H | Leu | H | CHO | 0.75 ± 0.07 | 0.77 ± 0.06 | >100 |
| 6m | | | | $CH(OH)SO_3Na$ | 0.6 ± 0.14 | 0.85 ± 0.07 | >100 |
| 5n | m-Cl | | | CHO | 0.26 ± 0.08 | 0.16 ± 0.06 | >100 |
| 6n | | | | $CH(OH)SO_3Na$ | 0.19 ± 0.06 | 0.09 ± 0.01 | >100 |
| 5o | | | $CH_3$ | CHO | 0.17 ± 0.06 | 0.14 ± 0.04 | >100 |
| 6o | | | | $CH(OH)SO_3Na$ | 0.16 ± 0.03 | 0.15 ± 0.08 | >100 |

TABLE 13

In Vitro and Cell-based Activity, and Cell-cytotoxicity Values of Norovirus 3CL Protease Inhibitors 5, 6 (s, t).

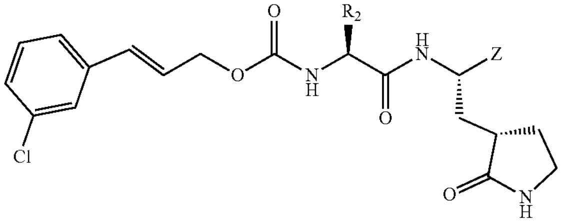

| Compound | $R_2$ | Y | $IC_{50}$ (μM) ± SD | $EC_{50}$ (μM) ± SD | $CC_{50}$ (μM) ± SD |
|---|---|---|---|---|---|
| 5s | Cha | CHO | 0.14 ± 0.01 | 0.06 ± 0.01 | 24.1 ± 0.6 |
| 6s | | $CH(OH)SO_3Na$ | 0.16 ± 0.01 | 0.07 ± 0.02 | 28.3 ± 2.8 |
| 5t | Leu | CHO | 0.15 ± 0.05 | 0.08 ± 0.01 | >100 |
| 6t | | $CH(OH)SO_3Na$ | 0.11 ± 0.02 | 0.08 ± 0.02 | >100 |

The invention claimed is:

1. A compound comprising of formula I:

(I)

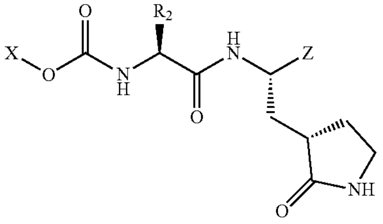

or a pharmaceutically acceptable salt thereof, where:

X is selected from the following structures shown in brackets with the oxygen linkage from formula (I) depicted for clarity:

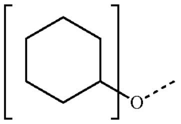,
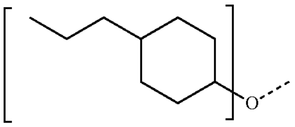,
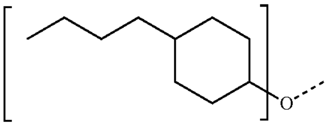,

-continued

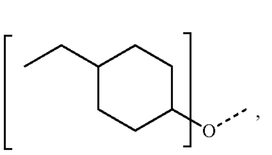

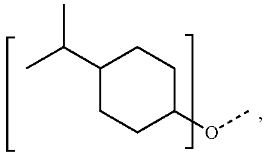

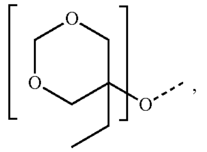

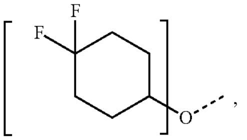

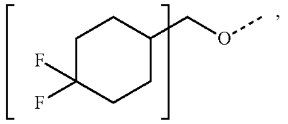

and

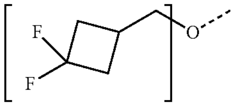

and $R_2$ is a branched or unbranched $C_1$-$C_6$ alkyl, $C_3$-$C_{10}$ cycloalkyl, $C_{6-10}$ aryl, $C_1$-$C_6$ alkylene-$C_{6-10}$ aryl, $C_2$-$C_6$ alkenyl, $C_2$-$C_6$ alkynyl, bicyclic or tricyclic moiety, or a combination thereof, wherein $C_1$-$C_6$ alkyl is optionally substituted with one or more halogen, —OH, —SH, —$SCH_3$, —$NH_2$, —COOH, —C(O)$NH_2$, —NH(C═NH)$NH_2$, $C_3$-$C_{10}$ cycloalkyl, $C_{6-10}$ aryl optionally substituted with —OH, or 5-9 membered heteroaryl having 1-3 ring heteroatoms selected from N, O, and S; and Z is selected from the group consisting of $C_1$-$C_6$ hydroxyalkyl, aldehydes, alpha-ketoamides, and bisulfite salts, —$CH_2OH$, —CHO, —CH(OH)$SO_3^-Na^+$, —[O(C═O)$CH_3$]$SO_3^-Na^+$, and —[O(C═O)$CH_2CH_3$]$SO_3^-Na^+$.

2. The compound or salt of claim 1, wherein Z is $C_1$-$C_6$ hydroxyalkyl or an aldehyde.

3. The compound or salt of claim 1, wherein Z is —$CH_2OH$ or —CHO.

4. The compound or salt of claim 1, wherein $R_2$ is $C_1$-$C_6$ alkyl optionally substituted with one or more halogen, —OH, —SH, —$SCH_3$, —$NH_2$, —COOH, —C(O)$NH_2$, —NH(C═NH)$NH_2$, $C_3$-$C_{10}$ cycloalkyl, $C_{6-10}$ aryl optionally substituted with —OH, or 5-9 membered heteroaryl having 1-3 ring heteroatoms selected from N, O, and S.

5. The compound or salt of claim 1, wherein $R_2$ is isobutyl.

6. The compound or salt of claim 1, wherein X is:

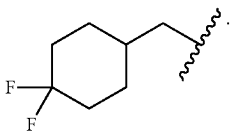

7. The compound or salt of claim 1, wherein X is:

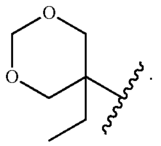 [SMILES: *C1(CC)COCOC1]

8. A compound according to claim 1 comprising a structure selected from

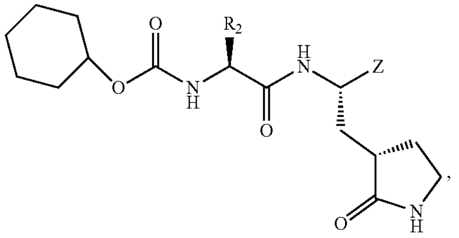

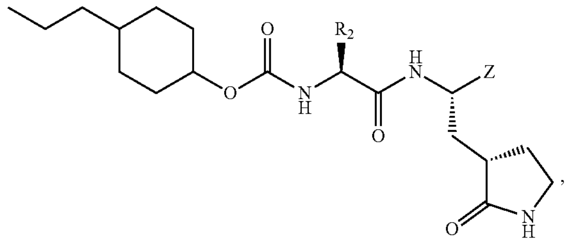

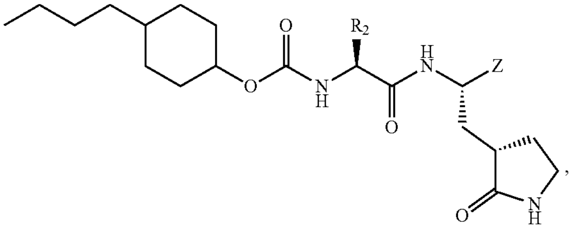

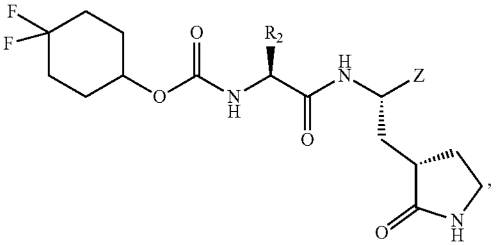

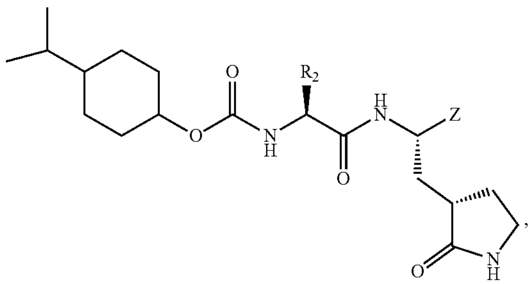

-continued

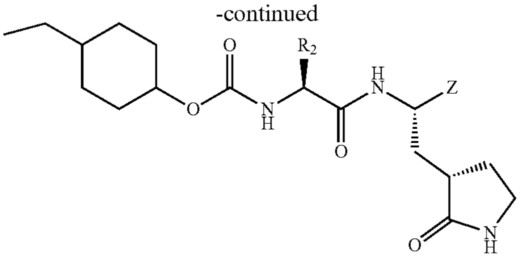

,

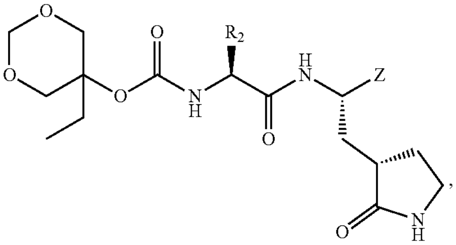

,

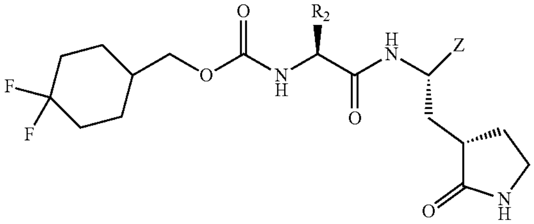

, or

-continued

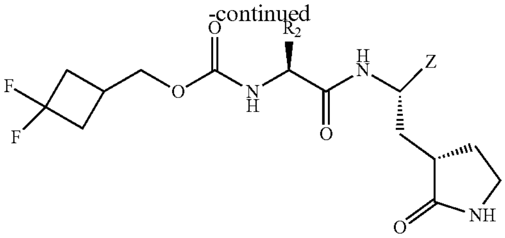

, or a pharmaceutically acceptable salt thereof, where Z is $CH(OH)SO_3Na$ or CHO, and $R_2$ is leucine (Leu) or cyclohexylalanine (Cha).

9. An antiviral composition comprising a first compound according to claim 1 and a pharmaceutically-acceptable carrier.

10. A method of treating a viral infection in a subject, said method comprising administering to said subject a therapeutically-effective amount of a first compound according to claim 1.

11. The method of claim 10, wherein the viral infection is a coronavirus, calicivirus, or picornavirus infection.

12. A method of inhibiting replication of a virus in a cell, said method comprising contacting said cell with a compound according to claim 1.

* * * * *